United States Patent [19]

Takashi et al.

[11] Patent Number: 5,066,812
[45] Date of Patent: Nov. 19, 1991

[54] 3-PROPENYLCEPHEM DERIVATIVE

[75] Inventors: Kamiya Takashi; Naito Toshihiko; Negi Shigeto; Komatu Yuuki; Kai Yasunobu; Nakamura Takaharu; Sugiyama Isao; Machida Yoshimasa; Nomoto Seiichiro; Kitoh Kyosuke; Katsu Kanemasa; Yamauchi Hiroshi, all of Ibaraki, Japan

[73] Assignee: Eisai Co., Ltd., Tokyo, Japan

[21] Appl. No.: 463,514

[22] Filed: Jan. 11, 1990

Related U.S. Application Data

[62] Division of Ser. No. 107,631, Oct. 13, 1987, Pat. No. 4,921,850.

[30] Foreign Application Priority Data

| Oct. 13, 1986 | [JP] | Japan | 61-241480 |
| Nov. 6, 1986 | [JP] | Japan | 61-262799 |
| Dec. 10, 1986 | [JP] | Japan | 61-292574 |
| Feb. 3, 1987 | [JP] | Japan | 62-21866 |
| Sep. 3, 1987 | [JP] | Japan | 62-219230 |
| Sep. 7, 1987 | [JP] | Japan | 62-222147 |

[51] Int. Cl.[5] ............................. C07D 285/08
[52] U.S. Cl. ........................................... 548/128
[58] Field of Search .............................. 548/128

[56] References Cited

U.S. PATENT DOCUMENTS

| 4,408,515 | 8/1984 | Teragi | 518/128 |
| 4,486,586 | 12/1984 | Narita et al. | 544/22 |
| 4,751,295 | 6/1988 | Oka et al. | 540/222 |
| 4,761,410 | 8/1988 | Takaya et al. | 514/206 |

FOREIGN PATENT DOCUMENTS

| 58-174387 | 10/1983 | Japan . |
| 58-198490 | 11/1983 | Japan . |
| 59-130295 | 7/1984 | Japan . |
| 59-172493 | 9/1984 | Japan . |
| 59-219292 | 12/1984 | Japan . |
| 60-97983 | 5/1985 | Japan . |
| 60-197693 | 10/1985 | Japan . |
| 62-6085 | 1/1986 | Japan . |
| 2177691 | 1/1987 | United Kingdom ............... 540/227 |

Primary Examiner—Robert Gerstl
Attorney, Agent, or Firm—Wenderoth, Lind & Ponack

[57] ABSTRACT

A 3-propenylcephem derivative of the following formula:

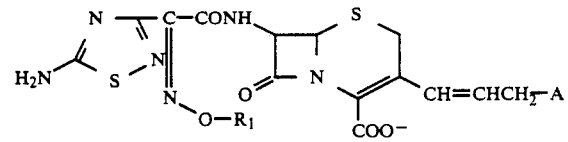

wherein $R_1$ represents a fluoro-substituted lower alkyl group or a cyano-substituted lower alkyl group, and A represents a cyclic or an acylic ammonio group, or a pharmaceutically acceptable salt thereof, exhibiting excellent anti-bacterial activities against both Gram-positive bacteria and Gram-negative bacteria; Process for the preparation thereof; Anti-bacterial composition; intermediate for the 3-propenylcephem derivative; and Process for the preparation of the intermediate.

5 Claims, No Drawings

3-PROPENYLCEPHEM DERIVATIVE

This application is a division of application Ser. No. 107,631, filed Oct. 13, 1987, now U.S. Pat. No. 4,921,850.

BACKGROUND OF THE INVENTION

1. Field of the Invention:

The present invention relates to novel cephem derivatives useful for anti-bacterial agents. More particularly, the present invention relates to 3-propenylcephem derivatives. The present invention also provides process for the preparation of the 3-propenylcephem derivatives, anti-bacterial agents, intermediates for the 3-propenylcephem derivatives, and process for the preparation of the intermediates.

2. Description of the Prior Art:

Cephem derivatives having ammonio group have been conventionally known from Japanese Patent Application Laid-open Nos. 174,387/83; 198,490/83; 130,295/84; 172,493/84; 219,292/84; 97,983/85; 197,693/85, 5,084/86, etc.

Particularly, cephem derivative having an ammoniopropenyl group at the 3-position thereof, similar to the compound of the present invention, have been disclosed in Japanese Patent Application Laid-open Nos. 172,493/84 and 5,084/86.

SUMMARY OF THE INVENTION

The present inventors have found that cephem derivatives having an ammoniopropenyl group at the 3-position thereof and a fluoro-substituted lower alkoxyimino group or a cyano-substituted lower alkoxyimino group in a side chain at the 7-position thereof have excellent anti-bacterial activities, leading to completion of the present invention.

An object of the present invention is therefore to provide novel cephem compounds useful as anti-bacterial agents; a process for the preparation thereof; pharmaceutical composition containing the same; intermediates for the derivatives; and a process for the preparation of the intermediates.

DETAILED DESCRIPTION OF THE INVENTION AND PREFERRED EMBODIMENTS

The present invention relates to 3-propenylcephem derivatives of the following formula (I):

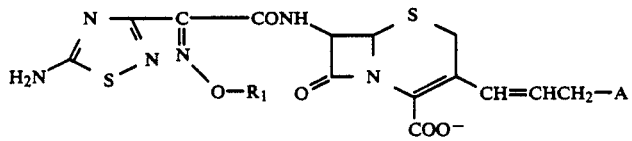

(I)

wherein $R_1$ represents a fluoro-substituted lower alkyl group or a cyano-substituted lower alkyl group, and A represents a cyclic or acyclic ammonio group, and a pharmaceutically acceptable salt thereof.

As illustrative examples of the fluoro-substituted lower alkyl group represented by $R_1$ in the formula (I), may be mentioned fluoromethyl, difluoromethyl, 2-fluoroethyl, 2,2-difluoroethyl, 2,2,2-trifluoroethyl, 1-fluoroethyl, 2-fluoropropyl, 1-(fluoromethyl)-2-fluoroethyl, 3-fluoropropyl and the like with fluoromethyl being particularly preferred.

Regarding the cyano-substituted lower alkyl group represented by $R_1$ in the formula (I), there may be enumerated cyanomethyl, 2-cyanoethyl, 3-cyanopropyl, and the like.

As illustrative examples of the acyclic ammonio group represented by A in the formula (I) may be mentioned a group of the following formula:

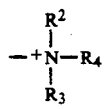

in which $R_2$, $R_3$ and $R_4$ are the same or different and mean individually a group selected from the group consisting of lower alkyl, hydroxyl-substituted lower alkyl, carbamoyl-substituted lower alkyl, cyano-substituted lower alkyl, amino, (lower alkyl)carbonylamino-substituted lower alkyl, aminosulfonylaminocarbonyl-substituted lower alkyl, (lower alkyl)sulfonylaminocarbonyl-substituted lower alkyl, (lower alkyl)amino-carbonyl-substituted lower alkyl, hydroxyl-and carbamoyl-substituted lower alkyl, hydroxyl- and hydroxy(lower alkyl)amino-carbonyl-substituted lower alkyl, (lower alkyloxy)aminocarbonyl-substituted lower alkyl, hydroxyaminocarbonyl-substituted lower alkyl, carbamoyl (lower alkyl)aminocarbonyl-substituted lower alkyl, hydroxy(lower alkyl)aminocarbonyl-substituted lower alkyl, (lower alkyl)amino-substituted lower alkyl, carboxylate(-lower alkyl)di(lower alkyl)ammonio-substituted lower alkyl, (lower alkyl)amino-substituted lower alkyl, di(lower alkyl)amino- and hydroxyl-substituted lower alkyl, ureido, hydroxyl, carboxyl-substituted lower alkyl, hydroxyl- and carbamoyl-substituted lower alkyl, lower alkyloxy-substituted lower alkyl, di(lower alkyl)amino-carbonyl-substituted lower alkyl, dicarbamoyl-substituted lower alkyl, bis[hydroxy(lower alkyl)]aminocarbonyl-substituted lower alkyl, dihydroxyl-substituted lower alkyl, trihydroxyl-substituted lower alkyl, bis[hydroxy(lower alkyl)amino-substituted lower alkyl, amino-substituted lower alkyl, oxo-substituted lower alkyl, di-lower alkyl-amino substituted lower alkyl, 5-membered heterocycle-substituted lower alkyl wherein said heterocycle stands for pyrazolyl, imidazolyl, oxadiazolyl or tetrazolyl.

Further, illustrative of a cyclic ammonio group represented by A in the formula (I) may include, for example, a group of the following formulae:

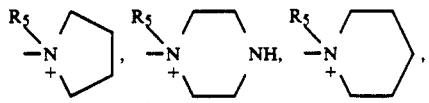

-continued

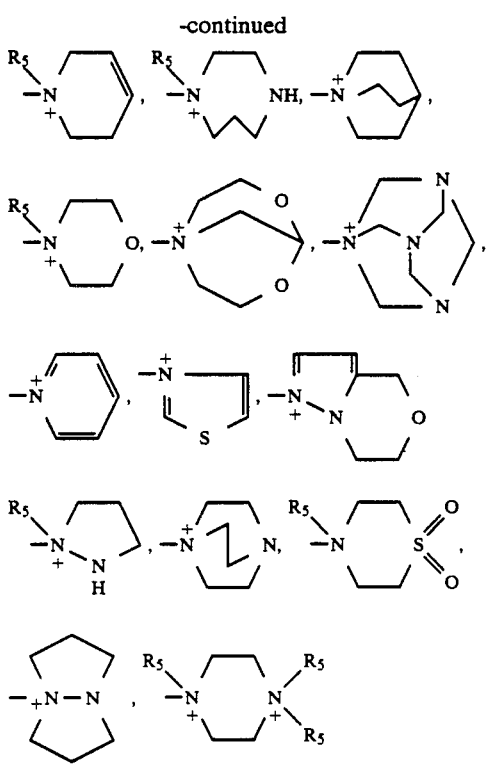

in which R$_5$ means a group selected from lower alkyl, carbamoyl-substituted lower alkyl, amino-substituted lower alkyl, hydroxyl-substituted lower alkyl, carboxyl-substituted lower alkyl, cyano-substituted lower alkyl, dihydroxyl-substituted lower alkyl and ureido-substituted lower alkyl groups, said cyclic ammonio group optionally containing on the ring thereof one or more substituents selected from hydroxyl-substituted lower alkyl, hydroxyl, formyl, sulfonic, carboxyl-substituted lower alkyl, carbamoyl, sulfamoyl, carboxyl, hydroxyimino-substituted lower alkyl, imino-substituted lower alkyl, bis[hydroxy(lower alkyl)]aminocarbonyl, hydroxy(lower alkyl)amino-carbonyl, amino, morpholinocarbonyl, carboxy(lower alkyloxy)-substituted lower alkyl, carboxy(lower alkyl-thio and lower alkyl-O-groups.

Illustrative of the lower alkyl group in the definition for A (R$_2$-R$_5$) in the formula (I) may include alkyl groups having 1-4 carbon atoms, such as methyl, ethyl, n-propyl, i-propyl, n-butyl, i-butyl, sec-butyl and t-butyl.

As non-toxic salts of the compounds of the formula (I), may be mentioned their pharmaceutically acceptable salts, for example, alkali metal salts such as sodium salts and potassium salts; ammonium salts; quaternary ammonium such as tetraethyl-ammonium salts and betaine salts; alkaline earth metal salts such as calcium salts and magnesium salts; inorganic acid salts such as hydrochlorides, hydrobromides, hydroiodides, sulfates, carbonates and bicarbonates; organic carboxylates such as acetates, maleates, lactates and tartrates; organic sulfonates such as methanesulfonates, hydroxymethanesulfonates, hydroxyethanesulfonates, taurine salts, benzenesulfonates and toluenesulfonates; amino acid salts such as arginine salts, lysine salts, serine salts, aspartates and glutamates; amine salts such as trimethylamine salts, triethylamine salts, pyridine salts, procaine salts, picoline salts, dicyclohexylamine salts, N,N'-dibenzyle- thylenediamine salts, N-methyl-glucamine salts, diethanolamine salts, triethanolamine salts, tris(hydroxymethylamino)methane salts and phenethylbenzylamine salts; etc.

Each of the compounds of the formula (I), which pertain to the present invention, has its syn-isomer (Z) and anti-isomer (E) with respect to its stereoscopic configuration at the following moiety:

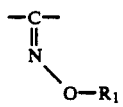

Although both isomers are included in the present invention, the syn-isomers are desired owing to their antibacterial activities.

The compounds of this invention can be produced by the following process.

Namely, the compounds of the formula (I) and their pharmaceutically acceptable salts can individually be obtained by reacting a compound, which is represented by the formula (II):

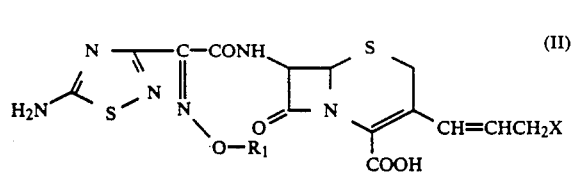

wherein R$_1$ means a fluoro-substituted lower alkyl group or a cyano-substituted lower alkyl group, and X denotes a halogen atom, a compound wherein the amino and/or carboxyl groups are protected with protecting group(s), or a salt thereof with a compound represented by the formula (III):

wherein A' means an amine corresponding to A, a compound wherein the functional group(s) are protected with protecting group(s), or a salt thereof; followed by optionally removing the protecting group(s).

As halogen atoms represented by X in the above formula (II), may be mentioned iodine atom, bromine atom and chlorine atom.

The above reaction may be carried out at a reaction temperature of −10° C.-60° C., preferably, 0° C.-40° C. As a reaction solvent, an anhydrous organic solvent is desired. As usable organic solvents, may be mentioned lower alkylnitriles such as acetonitrile and propionitrile; halogenated lower alkanes such as chloromethane, dichloromethane and chloroform; ethers such as tetrahydrofuran, dioxane and ethyl ether; amides such as dimethylformamide; esters such as ethyl acetate; ketones such as acetone; hydrocarbons such as benzene; alcohols such as methanol and ethanol; and sulfoxides such as dimethylsulfoxide; as well as mixed solvents thereof.

The removal of the protecting group(s) may be carried out by a method known per se in the art in accordance with the kind(s) of the protecting group(s) used, such as hydrolysis or reduction.

As the salts of the compounds of the formulae (II) and (III) and the protecting groups for the compounds, those employed routinely may also be used so long as they do not impair the above reaction.

Exemplary protecting groups for the amino group may include formyl group, acetyl group, chloroacetyl group, dichloroacetyl group, phenylacetyl group, thienylacetyl group, t-butoxycarbonyl group, benzyloxycarbonyl group, trityl group, p-methoxybenzyl group, diphenylmethyl group, benzylidene group, p-nitro-benzylidene group and m-chlorobenzylidene group. As illustrative protecting groups for the carboxyl group, may be mentioned p-methoxybenzyl group, p-nitrobenzyl group, t-butyl group, methyl group, 2,2,2-trichloroethyl group, diphenylmethyl group and pivaloyloxymethyl group. Here, use of a silylating agent such as N,O-bis(trimethylsilyl)acetamide, N-methyl-N-(trimethylsilyl)acetamide, N-methyl-N-(trimethylsilyl)trifluoroacetamide or N-(trimethylsilyl)acetamide is convenient because such a silylating agent can protect both amino and carboxyl groups at the same time.

As salts of the compounds of the formulae (II) and (III), suitable selection may be made from their salts such as alkali metal salts such as sodium salts and potassium salts; alkaline earth metal salts such as calcium salts and magnesium salts; ammonium salts; quaternary ammonium salts such as triethylammonium salts and betaine salts; inorganic acid salts such as hydrochlorides, hydrobromides, sulfates, carbonates, hydroiodides and bicarbonates; organic carboxylates such as acetates, trifluoroacetates, maleates, lactates and tartrates; organic sulfonates such as methanesulfonates, hydroxymethanesulfonates, hydroxyethanesulfonates, taurine salts, benzenesulfonates and toluenesulfonates; amine salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts and phenethylbenzylamine salts; amino acid salts such as arginine salts, aspartates, lysine salts, glutamates, serine salts and glycine salts; etc.

The compounds of this invention show strong antibacterial activities against both gram-positive and gram-negative bacteria and are hence useful as anti-bacterial agents. The compounds are used for treating a disease caused by bacteria.

When using the compounds of this invention as injections, they may be administered generally at a daily dose of 100 mg-10 g in 1-4 portions either intravenously or intramuscularly. Needless to say, the dose may be increased or decreased depending on the age and conditions of disease.

Their injections may be produced by a method known per se in the art. For example, each compound of this invention may be formulated into an injection by dissolving same in distilled water, if necessary, in the presence of an isotonic agent, solubilizer and/or the like. They may each be filled as powder in a vial or the like, thereby providing injections which require dissolution before use. These injections are hence dissolved in distilled water for injection, physiological saline, glucose injection, amino acid infusion or the like upon administration.

A compound of the above-mentioned formula (II) i.e. an intermediate; a compound wherein the amino and/or carboxyl group(s) are protected with a protective group; or salts of these compounds are all novel compounds. These compounds can be prepared by the following process. That is to say, the compounds can be prepared by reacting a compound of the formula:

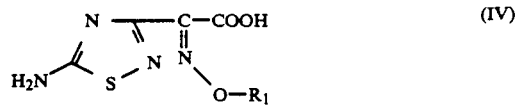

wherein $R_1$ has the same meanings as mentioned above, a reactive acid derivative thereof, a compound wherein an amino group is protected with a protective group, or a salt of the compound with a compound of the formula:

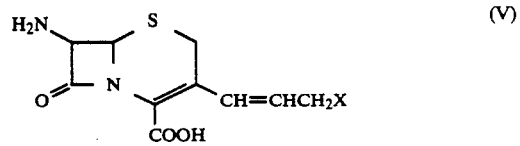

wherein X has the same meanings as defined above, a compound wherein a carboxyl group is protected with a protective group, or a salt thereof, followed by optionally removing the protective group, and/or converting a halogen atom represented by the symbol X into the other halogen atom.

The above-mentioned reaction can be conducted in accordance with a conventional reaction condition for an N-acylation. For example, the reaction can be carried out at a temperature from $-50°$ C. to $50°$ C. in an inert solvent such for example as tetrahydrofuran, ethyl acetate, acetone, N,N-dimethyl formamide, acetnitrile, dioxane or a mixed solvent thereof.

As for a reactive acid derivative of the compound of the formula (IV), there may be exemplified an acid halide such as acid chloride, acid bromide, etc. symmetrical acid anhydride, a mixed acid anhydride, an active ester, an active acid amide, and the like.

When a free carboxylic acid of the formula (IV) or a salt thereof is used in the reaction, it is preferable to conduct the reaction in the presence of a conventional condensing agent such as N,N'-dicyclohexylcarbodiimide, p-tuluene sulfonic acid, and the like, for example.

The conversion of a halogen atom represented by X into the other halogen atom is carried out in a conventional manner. For example, there can be prepared a compound of the formula (II) wherein X represents iodine atom, when a compound of the formula (II) wherein X represents chlorine atom is reacted with an alkali metal iodide.

Further, the intermediates of the under-mentioned formula (VI) are also novel compounds, such as a compound of the formula:

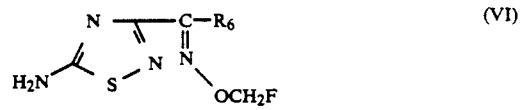

wherein $R_6$ represents carboxyl group, a halogenocarbonyl group, carbamoyl group, or cyano group, a compound wherein amino and/or carboxyl group(s) are protected with a protective group, or a salt thereof.

Illustrative of protective groups for the amino group and the carboxyl group may include a similar group as exemplified in the compound of the formula (II).

The above-mentioned compounds can be prepared by the following exemplary process.

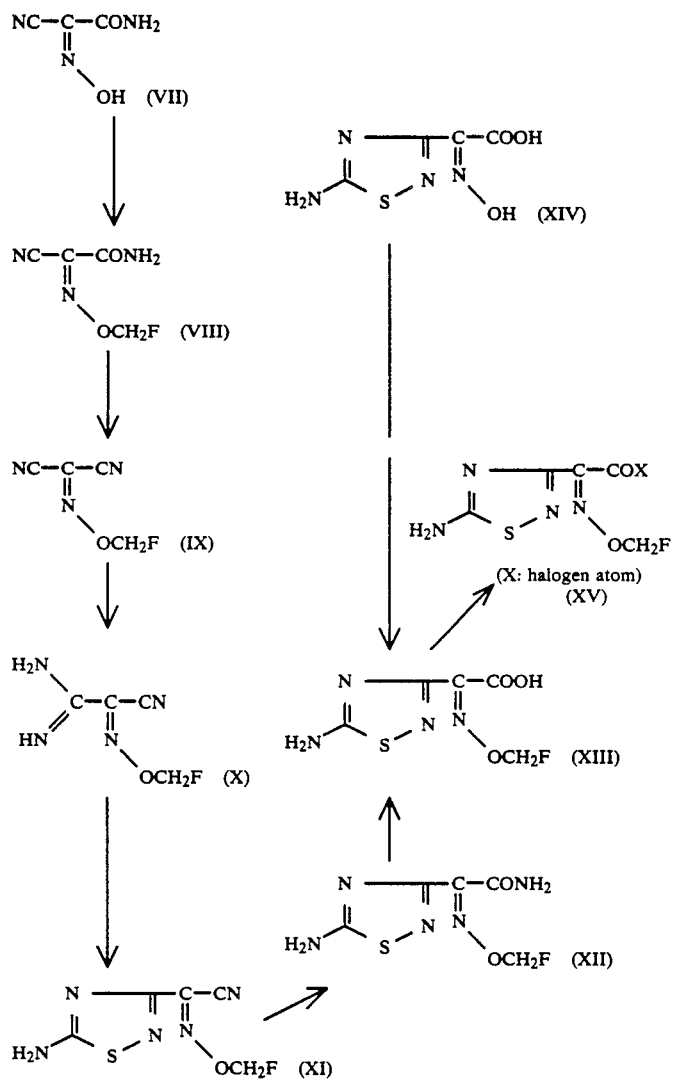

The compound of the formula (VIII) can be prepared by reacting a compound of the formula (VII) with a halogeno fluoromethane in an inert solvent.

As the halogeno fluoromethane, there may be exemplified bromo fluoromethane, iodo fluoromethane, and the like.

The reaction is carried out at a temperature ranging from −30° C. to 100° C.

The compound of the formula (IX) can be prepared by reacting a compound of the formula (VIII) with a dehydrating agent in an inert solvent. As the reaction temperature, it is preferable to use room temperature or above. A dehydrating agent may include oxyphosphorus chloride, thionyl chloride, etc.

The compound of the formula (X) can be prepared by reacting the compound of the formula (IX) with ammonia and/or ammonium salt in an inert solvent such as water, a lower alcohol, acetone, chloroform, etc. Suitable reaction temperature may range from −20° C. to room temperature. Ammonium salt may include ammonium chloride, ammonium acetate, ammonium sulfate, and the like.

The compound of the formula (XI) can be prepared by reacting the compound of the formula (X) with a halogenating agent such as gaseous bromine, gaseous chlorine, etc. to effect the halogenation, followed by reacting it with an alkali metal thiocyanate, preferably in the presence of a base. Suitable reaction temperature may range from −20° C. to room temperature. As an alkali metal thiocyanate, there may be used potassium thiocyanate, sodium thiocyanate, and the like.

A compound of the formula (XII), a compound wherein amino group is protected with a protective group, or a salt thereof can be prepared by hydrolyzing a compound of the formula (XI), a compound wherein amino group is protected with a protective group, or a salt thereof in the presence of an oxydizing agent and a base, followed by optionally removing the protective group.

The reaction can be carried out at a reaction temperature of from 0° C. to 70° C. in water, a buffer solution or a mixed solvent of the former with a lower alcohol.

There may be used hydrogen peroxide, oxygen, etc. as an oxydizing agent; and sodium hydroxide, potassium hydroxide, etc. as base.

A compound of the formula (XIII), a compound wherein amino group is protected with a protective group, or a salt thereof can be prepared by hydrolyzing a compound of the formula (XII), a compound wherein amino group is protected with a protective group, or a salt thereof in the presence of a base, followed by optionally removing the protective group.

The types of the base, solvents, the reaction temperatures, etc. may be the same as those described in the reaction sequence from the compound of the formula (XI) to that of the formula (XII).

Furthermore, a compound of the formula (XIII), a compound wherein amino group is protected with a protective group, or a salt thereof can be also prepared by reacting a compound of the formula (XIV) wherein amino and/or carboxyl group(s) are protected by a protected group, with a halogeno fluoromethane, followed by optionally removing the protective group.

The halogeno fluoromethane may include bromo fluoromethane, iodo fluoromethane, chloro fluoromethane.

The reaction can be carried out in an inert solvent at a reaction temperature ranging from $-30°$ C. to $100°$ C.

Illustrative examples of the inert solvent to be used may include sulfoxides such as dimethyl sulfoxide, etc., amides such as N,N-dimethylacetamide, formamide, hexamethylphosphoryl triamide, etc., ketones such as acetone, etc., or a mixed solvent thereof.

A compound of the formula (XV), a compound wherein amino group is protected with a protective group, or a salt thereof can be prepared by reacting a compound of the formula (XIII), a compound wherein amino group is protected with a protective group, or a salt thereof with a halogenating agent.

Illustrative examples of the halogenating agent may include phosphorus pentaoxide, thionyl chloride, thionyl bromide, oxyphosphorus chloride, and the like.

The above reaction can be carried out in an inert solvent such for example as dichloromethane, tetrahydrofuran, ethyl acetate, chloroform or a mixed solvent thereof at a reaction temperature of from $-50°$ C. to $50°$ C.

The present invention will next be described in further detail by the following Experiments and Examples.

EXPERIMENT 1

Synthesis of the raw material compound

Ethyl 2-(5-tritylamino-1,2,4-thiadiazol-3-yl)-(Z)-2-fluoromethoxyimino acetate

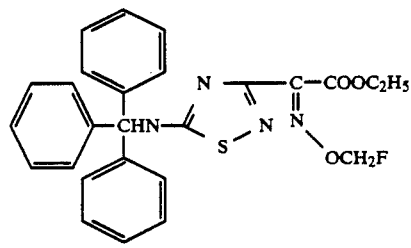

Ethyl 2-(5-tritylamino-1,2,4-thiadiazol-3-yl)-(Z)-2-hydroxyimino acetate (60.4 g) was dissolved in dimethyl sulfoxide (210 ml), and then potassium carbonate (96.48 g) was added thereto under ice-cooling. The solution was stirred for 10 minutes. Thereafter, bromofluoromethane (19 g) was added thereto, and the solution was stirred for 3 hours at room temperature. Ethyl acetate (1 liter) was added to the reaction solution and the solution was washed with water and then with a saturated brine, followed by drying with addition of anhydrous magnesium sulfate. The solvent was distilled off, and ethanol (120 ml) was added to the residue. Crystals deposited were collected by filtration, and washed with ethanol to obtain the object product (58.2 g).

EXPERIMENT 2

Synthesis of the raw material compound 2-(5-Tritylamino-1,2,4-thiadiazol-3-yl)-(Z)-2-fluoromethoxyimino acetic acid

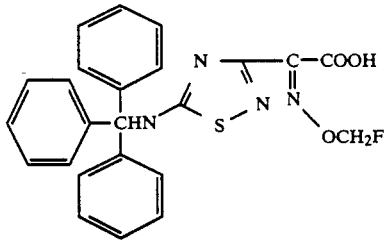

Into a mixed solution containing sodium hydroxide (2.04 g), ethanol (146 ml) and water (29 ml) was added the compound (17.87 g) prepared in Experiment 1, and the solution was stirred for 20 minutes under reflux. After the solution was concentrated under reduced pressure, ethyl acetate (200 ml) and 1N hydrochloric acid (77 ml) were added thereto. The ethyl acetate layer was separated to collect and washed with a saturated brine, followed by drying with addition of anhydrous magnesium sulfate. The solvent was distilled off to obtain crystals. The crystals were crushed with addition of petroleum ether, and then recovered by filtration to obtain the object product (16.55 g).

EXPERIMENT 3

Synthesis of the raw material compound p-Methoxybenzyl 7β-[2-(5-tritylamino-1,2,4-thiadiazol-3-yl)-(Z)-2-fluoromethoxyiminoacetamido]-3-[(Z)-3-chloro-1-propen-1-yl]-3-cephem-4-carboxylate

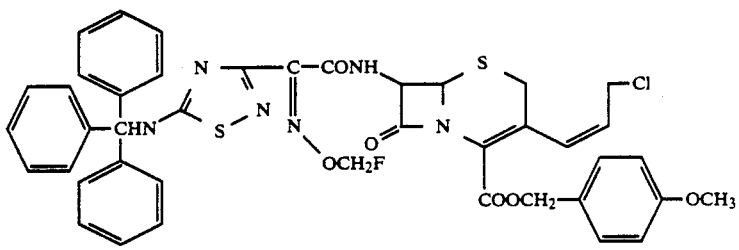

Dimethylformamide (348 μl) and tetrahydrofuran (4.1 ml) were cooled to −10° C., and phosphorus oxychloride (418 μl) was added thereto, and stirred for 90 minutes under ice-cooling. To this solution was added a solution of the compound (1.73 g) prepared in Experiment 2 in tetrahydrofuran (5.5 ml) with cooling to −10° C., and the resulting solution was stirred for 90 minutes under ice-cooling. The reaction solution was cooled to −20° C., and a mixed solution containing p-methoxybenzyl 7β-amino-3-[(Z)-3-chloro-1-propen-1-yl]-3-cephem-4-carboxylate hydrochloride (1.78 g), N-(trimethylsilyl)acetamide (2.95 g), ethyl acetate (18 ml) and tetrahydrofuran (5.5 ml) was added thereto, and the resulting solution was stirred for one hour at −10° C. To the reaction solution was added ethyl acetate (100 ml), and the resulting solution was washed successively with water, a saturated aqueous sodium hydrogencarbonate and a saturated brine, followed by drying with addition of anhydrous magnesium sulfate. The solvent was distilled off, and the residue was purified by silica gel column chromatography to obtain the object product (2.65 g).

EXPERIMENT 4

Synthesis of the raw material compound p-Methoxybenzyl 7β-[2-(5-tritylamino-1,2,4-thiadiazol-3-yl)-(Z)-2-fluoromethoxyiminoacetamido]-3-[(E)-3-iodo-1-propen-1-yl]-3-cephem-4-carboxylate sulting solution was stirred for 15 minutes under ice-cooling and for additional 90 minutes at a room temperature. The solvent was distilled off, and the residue was extracted with ethyl acetate (500 ml). The extract was washed with a saturated aqueous sodium thiosulfate solution and with a saturated brine, followed by drying with addition of anhydrous magnesium sulfate. The dried extract was concentrated under reduced pressure and n-hexane was added thereto. The resulting precipitates were collected by filtration to obtain the object product (10.92 g).

EXPERIMENT 5

Synthesis of the raw material compound p-Methoxybenzyl 7β-[2-(5-tritylamino-1,2,4-thiadiazol-3-yl)-(Z)-difluoromethoxyiminoacetamido]-3-[(Z)-3-chloro-1-propen-1-yl]-3-cephem-4-carboxylate

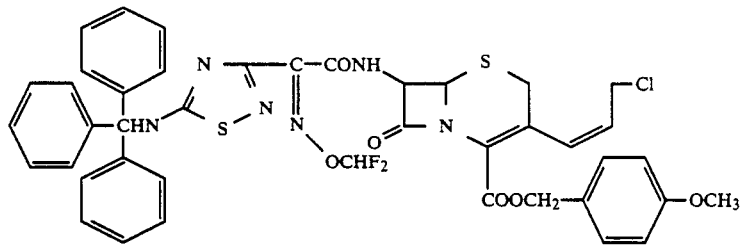

In the same manner as described in Experiment 3, 2-(5-tritylamino-1,2,4-thiadiazol-3-yl)-(Z)-2-difluoromethoxyiminoacetic acid (2.00 g) was reacted with p-methoxybenzyl 7β-amino-3-[(Z)-3-chloro-1-propen-1-yl]-3-cephem-4-carboxylate hydrochloride (1.795 g) to obtain the object product (3.17 g).

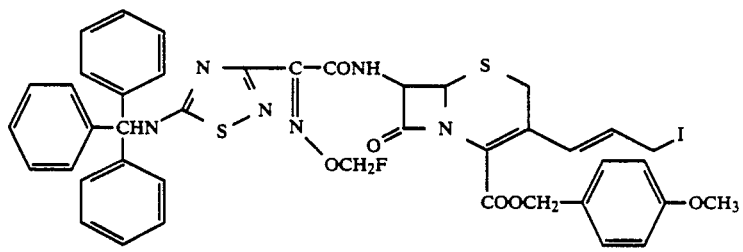

The compound (10.11 g) prepared in Experiment 3 was dissolved in acetone (212 ml), and sodium iodide (9.03 g) was added thereto under ice-cooling. The re-

EXPERIMENT 6

Synthesis of the raw material compound p-Methoxybenzyl 7β-[2-(5-tritylamino-1,2,4-thiadiazol-3-yl)-(Z)-2-difluoromethoxyiminoacetamido]-3-[(E)-3-iodo-1-propen-1-yl]-3-cephem-4-carboxylate

EXAMPLE 2

7β-[2-(5-Amino-1,2,4-thiadiazol-3-yl)-(Z)-2-fluoromethoxyiminoacetamido]-3-[(E)-3-[1-(2-hydroxyethyl)-4-carbamoyl-1-piperidinio]-1-propen-1-yl]-3-cephem-4-carboxylate

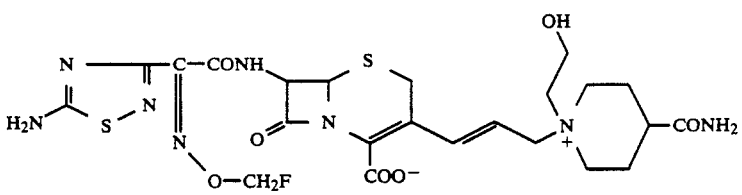

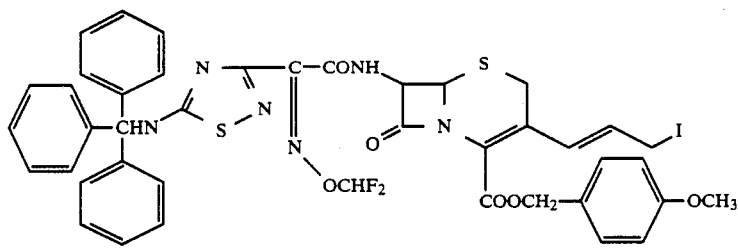

In the same manner as described in Experiment 4, the compound (3.00 g) prepared in Experiment 5 was reacted with sodium iodide (2.62 g) to obtain the object product (2.92 g).

EXAMPLE 1

7β-[2-(5-Amino-1,2,4-thiadiazol-3-yl)-(Z)-2-fluoromethoxyiminoacetamido]-3-[(E)-3-(carbamoylmethylethylmethylammonio)-1-propen-1-yl]-3-cephem-4-carboxylate

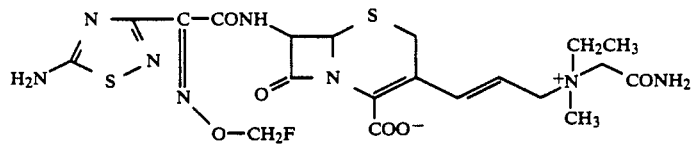

The compound (550 mg) prepared in Experiment 4 was dissolved in a mixed solution containing ethyl acetate (20 ml) and ethyl ether (10 ml), and then ethylmethylaminoacetamide (117 mg) was added thereto. The resulting solution was stirred at room temperature for 4 hours and 30 minutes. Isopropyl ether was added to the reaction solution, and the resulting precipitates were collected by filtration and dried to obtain the yellowish brown powder (400 mg).

The powder was stirred in a mixed solution of trifluoroacetic acid (4.5 ml)-anisole (4 ml) for one hour under ice-cooling, and ethyl ether was added thereto. The resulting precipitates were collected by filtration and washed with ethyl ether. The precipitates were suspended in water (5 ml). The suspension was adjusted to pH 5.5–6.5 with sodium acetate. Insolubles were removed by filtration, and the filtrate was purified by reversed phase chromatography to obtain the object product (49 mg).

The compound (700 mg) prepared in the Experiment 4 was dissolved in dimethylformamide (3 ml), and a solution of 1-(2-hydroxyethyl)isonipecotamide (194 mg) in dimethylformamide (0.5 ml) was added thereto. The solution was stirred overnight. The reaction solution was added to ethyl ether (120 ml), and the resulting precipitates were collected by filtration to obtain yellow powder (680 mg).

To this powder was added anisole (4.5 ml), and trifluoroacetic acid (5.3 ml) was added drop by drop over 30 minutes with stirring under ice-cooling. After the dropping was completed, the mixture was stirred for additional one hour and 30 minutes. To the reaction solution was added isopropyl ether (50 ml), and the resulting precipitates were collected by filtration. The precipitates were suspended in water (30 ml), and the suspension was adjusted to pH 7.0 with sodium acetate. The resulting insolubles were removed by filtration, and the filtrate was purified by reversed phase silica gel column chromatography to obtain the following two types of isomers of the subject compound:

Isomer (2-1) 21 mg.
Isomer (2-2) 20 mg.
1:1 Mixture of the two isomers 50 mg.

EXAMPLE 3

7β-[2-(5-Amino-1,2,4-thiadiazol-3-yl)-(Z)-2-fluoromethoxyiminoacetamido]-3-[(E)-3-[1S-carbamoylethyl)-dimethylammonio]-1-propen-1-yl]-3-cephem-4-carboxylate (3-1)

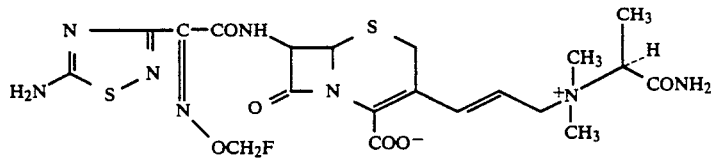

7β-[2-(5-Amino-1,2,4-thiadiazol-3-yl)-(Z)-2-fluoromethoxyiminoacetamido]-3-[(E)-3-[(1R-carbamoylethyl)-dimethylammonio]-1-propen-1-yl]-3-cephem-4-carboxylate (3-2)

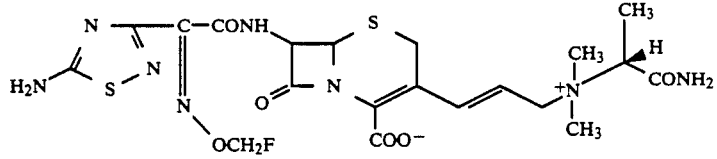

The compound (600 mg) prepared in Experiment 4 was dissolved in a mixed solution containing ethyl acetate (20 ml) and ethyl ether (10 ml), and then 2-dimethylaminopropylamide (150 mg) was added thereto. The resulting solution was stirred for 3 hours at room temperature. Isopropyl ether was added to the reaction solution, and the resulting precipitates were collected by filtration, followed by drying to obtain yellowish brown powder (50 mg).

This powder was stirred in a mixed solution containing trifluoroacetic acid (5.5 ml) and anisole (5 ml) for one hour under ice-cooling and, thereafter, ethyl ether was added thereto. The resulting precipitates were collected by filtration and washed with ethyl ether. The precipitates were suspended in water (5 ml), and the suspension was adjusted to pH 5.5–6.5 with sodium acetate. The insolubles were removed by filtration, and the filtrate was purified by reversed phase silica gel column chromatography to obtain the object products of 8 mg of the (3-1), 7 mg of the (3-2), and 4 mg of the mixture (1:1) of the (3-1) and the (3-2).

EXAMPLE 4

7β-[2-(5-Amino-1,2,4-thiadiazol-3-yl)-(Z)-2-fluoromethoxyiminoacetamido]-3-[(E)-3-[(2-hydroxypropyl)-dimethylammonio]-1-propen-1-yl]-3-cephem-4-carboxylate

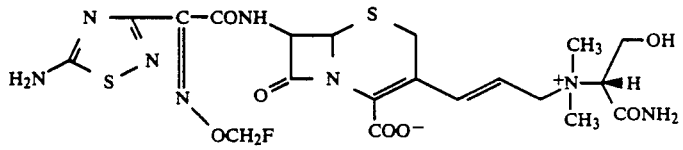

The compound (550 mg) prepared in Experiment 4 was dissolved in a mixed solution containing ethyl acetate (20 ml) and ethyl ether (10 ml), and then 3-dimethylamino-2-propanol (0.124 ml) was added thereto. The resulting solution was stirred at room temperature for one hour and 30 minutes. Isopropanol was added to the reaction solution. The resulting precipitates were collected by filtration and dried to obtain yellowish brown powder (530 mg).

This powder was stirred in a mixed solution containing trifluoroacetic acid (5.5 ml) and anisole (5 ml) for one hour under ice-cooling. Thereafter, ethyl ether was added thereto. The resulting precipitates were collected by filtration and washed with ethyl ether. The precipitates were suspended in water (5 ml). The suspension was adjusted to pH 5.5–6.5 with sodium acetate. Insolubles were removed by filtration and the filtrate was purified by reversed phase silica gel column chromatography to obtain the object product (70 mg).

EXAMPLE 5

7β-[2-(5-Amino-1,2,4-thiadiazol-3-yl)-(Z)-2-fluoromethoxyiminoacetamido]-3-[(E)-3-[(1R-carbamoyl-2-hydroxyethyl)dimethylammonio]-1-propen-1-yl]-3-cephem-4-carboxylate The compound (1.00 g) prepared in Experiment 4 was dissolved in dimethylformaide (2 ml). A solution of N,N-dimethyl-D-serinamide was prepared by dissolving N,N-dimethyl-D-serinamide trifluoroacetate (590 mg) in methanol (5 ml), adding 1N-aqueous sodium hydroxide solution (2.4 ml) thereto, followed by distilling off the solvent under reduced pressure, and extracting the residue with acetonitrile (2 ml). The N,N-dimethyl-D-serinamide solution was added to the solution of the compound prepared in Experiment 4 in dimethylformamide under ice-cooling. The resulting solution was stirred for 30 minutes. The reaction solution was added to ethyl ether, and the resulting precipitates were collected by filtration to obtain yellow powder (1.1 g).

To this powder was added anisole (8 ml), and trifluoroacetic acid (9 ml) was dropped over 30 minutes with stirring under ice-cooling, followed by stirring for additional one hour and 30 minutes. Ethyl ether was added to the reaction solution, and the resulting precipitates were collected by filtration. The precipitates were suspended in water (10 ml). The suspension was then adjusted to pH 7 with sodium acetate. The isolubles were removed by filtration, and the filtrate was purified by reversed phase silica gel column chromatography to obtain the object product (30 mg).

EXAMPLE 6

7β-[2-(5-Amino-1,2,4-thiadiazol-3-yl)-(Z)-2-fluoromethoxyiminoacetamido]-3-[(E)-3-(4R-hydroxy-2R-hydroxymethyl-1-methyl-1-pyrrolidinio)-1-propen-1-yl]-3-cephem-4-carboxylate were suspended in water (30 ml), and the suspension was adjusted to pH 7 with sodium acetate. The insolubles were removed by filtration, and the filtrate was purified by reversed phase silica gel column chromatography to obtain the following two types of isomers (relating to a nitrogen atom of pyrrolidine):
Isomer (6-1) 27 mg.
Isomer (6-2) 100 mg.

EXAMPLE 7

7β-[2-(5-Amino-1,2,4-thiadiazol-3-yl)-(Z)-2-fluoromethoxyiminoacetamido]-3-[(E)-3-[4R-hydroxy-1-(2-hydroxyethyl)-2S-hydroxymethyl-1-pyrrolidinio]-1-propen-1-yl]-3-cephem-4-carboxylate

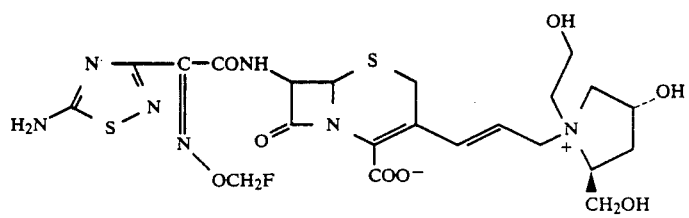

The compound (2.0 g) prepared in Experiment 4 was added to a solution containing (R)-4-hydroxy-1-(2-hydroxyethyl)-(S)-2-hydroxymethylpyrrolidine (450 mg) in dimethylformamide (5 ml). The resulting solution was stirred overnight. The reaction solution was added to ethyl acetate. The resulting precipitates were collected by filtration to obtain yellow powder (1.65 g).

To the powder was added anisole (10 ml), and then trifluoroacetic acid (11.7 ml) was dropped over 30 minutes with stirring under ice-cooling, and further stirred for additional one hour and 30 minutes. Isopropyl ether was added to the reaction solution, and the resulting precipitates were collected by filtration. The precipitates were suspended in water (4.5 ml), and the suspen-

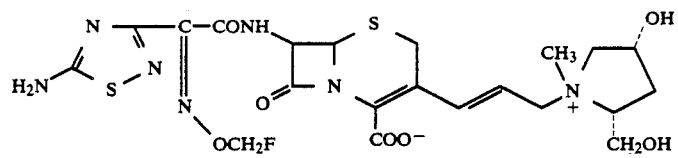

The compound (700 mg) prepared in Experiment 4 was dissolved in acetone (4 ml), and a solution of N-methyl-cis-4-hydroxy-D-prolinol (89 mg) in acetone (2 ml) was added thereto. The resulting solution was stirred overnight. The reaction solution was added to ethyl ether (100 ml), and the resulting precipitates were collected by filtration to obtain yellow powder (700 mg).

To this powder was added anisole (4.5 ml), and trifluoroacetic acid (5.3 ml) was dropped over 30 minutes with stirring under ice-cooling, and stirred for additional one hour and 30 minutes. To the reaction solution was added isopropyl ether (50 ml). The resulting precipitates were collected by filtration. The precipitates sion was adjusted to pH 7 with sodium acetate. The insolubles were removed by filtration, and the filtrate was purified by reversed phase silica gel column chromatography to obtain two types of the isomers (relating to a nitrogen atom of pyrrolidine) of the subject compound as follows:
Isomer (7-1) 96 mg.
Isomer (7-2) 207 mg.

EXAMPLE 8

7β-[2-(5-Amino-1,2,4-thiadiazol-3-yl)-(Z)-2-fluoromethoxyiminoacetamido]-3-[(E)-3-(4R-hydroxy-2S-hydroxymethyl-1-methyl-1-pyrrolidinio)-1-propen-1-yl]-3-cephem-4-carboxylate

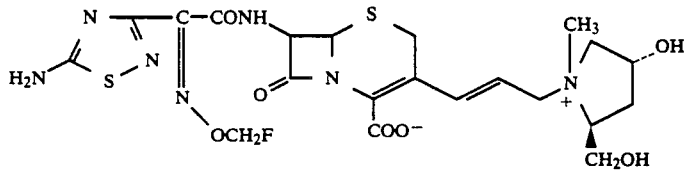

The compound (700 mg) prepared in Experiment 4 was dissolved in acetone (4 ml), and a solution of N-methyl-trans-4-hydroxy-L-prolinol (89 mg) in acetone (2 ml) was added thereto, and the resulting solution was stirred overnight. The reaction solution was added to ethyl ether (100 ml), and the resulting precipitates were collected by filtration to obtain yellow powder (700 mg).

To the powder was added anisole (4.5 ml), and trifluoroacetic acid (5.3 ml) was dropped with stirring under ice-cooling over 30 minutes, and then the mixture was stirred for additional one hour and 30 minutes. To the reaction solution was added isopropyl ether (50 ml), and the resulting precipitates were collected by filtration. The precipitates were then suspended in water (30 ml). The suspension was adjusted to pH 7 with sodium acetate. The insolubles were removed by filtration, and the filtrate was purified by reversed phase silica gel column chromatography to obtain the object compound (92 mg).

EXAMPLE 9

7β-[2-(5-Amino-1,2,4-thiadiazol-3-yl)-(Z)-2-fluoromethoxyiminoacetamido]-3-[(E)-3-(1-carbamoylmethyl-3-hydroxy-1-pyrrolidinio)-1-propen-1-yl]-3-cephem-4-carboxylate

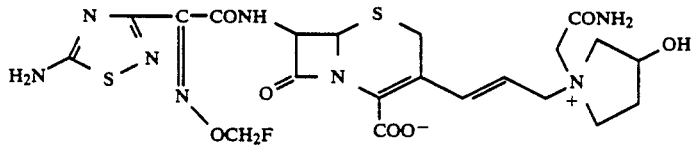

The compound (1.0 g) prepared in Experiment 4 was dissolved in dimethylformamide (4 ml), and a solution of N-carbamoylmethyl-3-hydroxypyrrolidine (186 mg) in dimethylformamide (2 ml) was added thereto. The resulting solution was stirred overnight. The reaction solution was added to ethyl ether (200 ml). The resulting precipitates were collected by filtration to obtain yellow powder (970 mg).

To the powder was added anisole (9.0 ml), and then trifulooroacetic acid (10.6 ml) was dropped over 30 minutes with stirring under ice-cooling. The mixture was further stirred for additional one hour and 30 minutes. To the reaction solution was added isopropyl ether (80 ml), and the resulting precipitates were collected by filtration. The precipitates were suspended in water (50 ml). The suspension was adjusted to pH 7 with sodium acetate. The insolubles were removed by filtration, and the filtrate was purified by reversed phase silica gel column chromatography to obtain the respective types of isomers (relating to a nitrogen atom, and carbon atom on the 3-position of pyrrolidine, and there are four types on high pressure liquid chromatography) of the subject compound as follows:

Isomer (9-1) 71 mg (mixture of two types).
Isomer (9-2) 70 mg (single material).
Isomer (9-3) 54 mg (single material).

EXAMPLE 10

7β-[2-(5-Amino-1,2,4-thiadiazol-3-yl)-(Z)-2-fluoromethoxyiminoacetamido]-3-[(E)-3-(1-methyl-4-sulfo-1-piperazinio)-1-propen-1-yl]-3-cephem-4-carboxylate

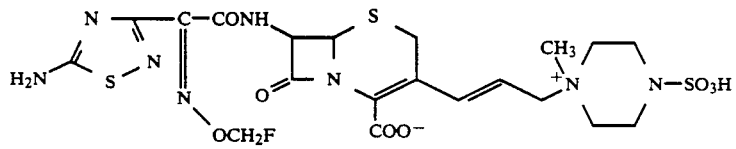

The compound (2.0 g) prepared in Experiment 4 was added to a mixed solution containing 4-methylpiperazinosulfonic acid sulfate (718 mg), N-methyl-N-(trimethylsilyl) trifluoroacetamide (2 ml) and dimethylformamide (6 ml), and the resulting solution was stirred overnight. To the reaction solution was added methanol (2 ml), and the insolubles were removed by filtration. The filtrate was added to a mixed solution containing ethyl acetate (50 ml) and ethyl ether (50 ml), and the resulting precipitates were collected by filtration to obtain yellow powder (1.79 g).

To this powder was added anisole (10.9 ml), and trifluoroacetic acid (12.7 ml) was dropped over 30 minutes with stirring under ice-cooling. The resulting solution was further stirred for additional one hour and 30 minutes. To the reaction solution was added isopropyl ether (100 ml), and the resulting precipitates were collected by filtration. The precipitates were suspended in water (4.5 ml), and the suspension was adjusted to pH 7 with sodium acetate. Insolubles were removed by filtration and the filtrate was purified by reversed phase silica gel column chromatography to obtain the object product (50 mg).

EXAMPLE 11

7β-[2-(5-Amino-1,2,4-thiadiazol-3-yl)-(Z)-2-fluoromethoxyiminoacetamido]-3-[(E)-3-(1-carbamoylmethyl-4-hydroxy-1-piperidinio)-1-propen-1-yl]-3-cephem-4-carboxylate

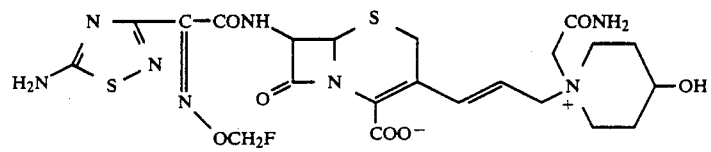

The compound (1.0 g) prepared in Experiment 4 was dissolved in acetone (9 ml), and N-carbamoylmethyl-4-hydroxypiperidine (206 mg) was added thereto. The solution was stirred overnight. The reaction solution was added to a mixed solution (100 ml) containing ethyl ether and isopropyl ether (2:1), and the resulting precipitates were collected by filtration to obtain yellow powder (1.0 g).

To this powder was added anisole (9.0 ml), and trifluoroacetic acid (10.6 ml) was dropped over 30 minutes with stirring under ice-cooling, and the resulting solution was further stirred for additional one hour and 30 minutes. To the reaction solution was added isopropyl ether (80 ml), and the resulting precipitates were collected by filtration. The precipitates were suspended in water (5 ml), and the suspension was adjusted to pH 7.0 with sodium acetate. Insolubles were removed by filtration, and the filtrate was purified by reversed phase silica gel column chromatography to obtain the object product (166 mg).

EXAMPLE 12

7β-[2-(5-Amino-1,2,4-thiadiazol-3-yl)-(Z)-2-fluoromethoxyiminoacetamido]-3-[(E)-3-(5-aza-1-methyl-2,8-dioxabicyclo[3.3.1]nona-5-io)-1-propen-1-yl]-3-cephem-4-carboxylate

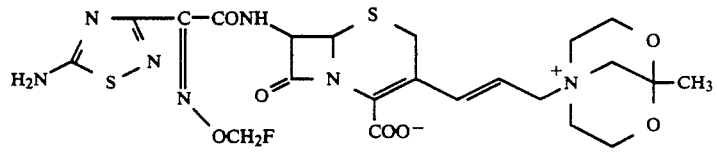

The compound prepared in Experiment 4 was dissolved in dimethylformamide (10 ml), 5-aza-1-methyl-2,8-dioxabicyclo [3.3.1]nonane (800 mg) was added thereto at room temperature. The resulting solution was stirred for 20 minutes. The reaction solution was diluted with ethyl acetate (25 ml) and the solution was added to ethyl ether to obtain brown precipitates (3.85 g).

The precipitates were dissolved in anisole (23 ml), and trifluoroacetic acid (26 ml) was added thereto under ice-cooling. The solution was stirred for 30 minutes at the same temperature. Ethyl ether was added to the reaction solution, and resulting precipitates were collected by filtration. The precipitates were suspended in water (40 ml), and the suspension was adjusted to pH 7.0 with sodium acetate. Insolubles were removed by filtration, and the filtrate was purified by reversed phase silica gel column chromatography to obtain the object product (408 mg).

In the same manner as described in the Examples 1–12, the following compounds in Examples 13–113 were preapred:

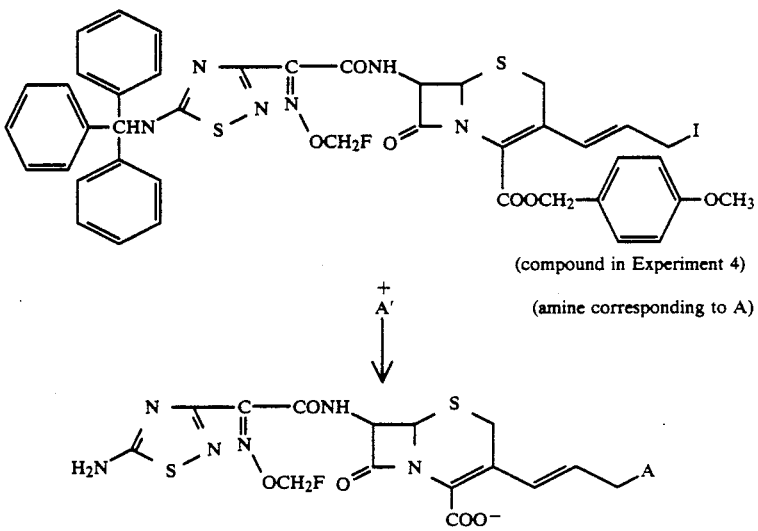

(compound in Experiment 4)

+
A′ (amine corresponding to A)

Plural isomers may be formed due to the portion of ammonio group on A. When these isomers were separated, the respective yields were shown for the respective isomers individually.

The following abbreviations were used:

Boc: t-butoxy carbonyl group
tBu: t-butyl group
Bh: benzhydryl group
Tr: trityl group.

| Example No. | A | Use amount of the starting compound | | Yield of the objective product |
|---|---|---|---|---|
| | | A' (amine) | Compound of Experiment 4 | |
| 13 | CH₃, CONH₂ on pyrrolidinium | 183 mg | 800 mg | Isomer (13-1) 29 mg<br>Isomer (13-2) 33 mg<br>Mixture of both isomers 14 mg |
| 14 | CN on pyrrolidinium | 107 mg | 600 mg | 8 mg |
| 15 | OH, OH on pyrrolidinium | 169 mg | 1.0 g | Isomer (15-1) 23 mg<br>Isomer (15-2) 35 mg |
| 16 | OH, CH₂OH on pyrrolidinium | 187 mg | 1.0 g | 114 mg |
| 17 | CH₂OH, CONH₂ on pyrrolidinium | 203 mg | | 33 mg |
| 18 | CH₂OH, COOH on pyrrolidinium | (CONH₂, CH₂OH on pyrrolidine) | 1.0 g | 23 mg (As by-product of Example 17) |
| 19 | CONH₂ on pyrrolidinium | 247 mg | 600 mg | 85 mg |
| 20 | OH on pyrrolidinium | 100 mg | 500 mg | 90 mg |
| 21 | CH₃, OH on pyrrolidinium | 136 mg | 1.0 g | 64 mg |
| 22 | NH₂ on pyrrolidinium | 345 mg (BOC—HN on pyrrolidine) | 1.0 g | 40 mg |

-continued

| Example No. | A | Use amount of the starting compound | | Yield of the objective product |
|---|---|---|---|---|
| | | A' (amine) | Compound of Experiment 4 | |
| 23 | HOCH$_2$-CH(OH)-N$^+$(pyrrolidine) | 131 mg | 700 mg | Isomer (23-1) 13 mg<br>Isomer (23-2) 13 mg |
| 24 | CH$_3$-N$^+$(piperazine)N-CHO | 544 mg | 2.0 g | 226 mg |
| 25 | CH$_3$-N$^+$(piperazine)N-CH$_2$CH$_2$SO$_3$Na | 344 mg | 1.0 g | 17 mg |
| 26 | CH$_3$-N$^+$(piperazine)N-C(=NH)CH$_3$ · HCl | 229 mg (Hydrochloride) | 1.0 g | 112 mg |
| 27 | HOCH$_2$CH$_2$-N$^+$(piperazine)N-CH$_2$CH$_2$OH | 288 mg | 730 mg | 105 mg |
| 28 | HOCH$_2$CH$_2$-N$^+$(piperazine)N-CONH$_2$ | 250 mg | 1 g | 6 mg |
| 29 | HOCH$_2$CH$_2$-N$^+$(piperazine)N-SO$_2$NH$_2$ | 200 mg | 1 g | 17 mg |
| 30 | HOCH$_2$-CH(OH)-N$^+$(piperazine)N-CONH$_2$ | 220 mg | 1 g | 10 mg |
| 31 | H$_2$NCO-CH$_2$-N$^+$(piperazine)N-CONH$_2$ | 200 mg | 1 g | 30 mg |
| 32 | H$_2$NCONH-CH$_2$-N$^+$(piperazine)N-CONH$_2$ | 200 mg | 1 g | 22 mg |
| 33 | CH$_3$-N$^+$(piperazine)N-CH$_2$COOH<br>(CH$_3$-N(piperazine)N-CH$_2$COO-$^t$Bu) | 260 mg | 750 mg | 90 mg |

-continued

| Example No. | A | Use amount of the starting compound | | Yield of the objective product |
|---|---|---|---|---|
| | | A' (amine) | Compound of Experiment 4 | |
| 34 | [structure: N-methylpiperazine-N'-propanoic acid, N-methyl quaternary] | 410 mg | 750 mg ([structure: CH₃—N piperazine N—CH₂CH₂—COO—BH]) | 50 mg |
| 35 | [structure: morpholinium with CH₂CH₂CONH₂ substituent] | 230 mg | 1 g | 56 mg |
| 36 | [structure: morpholinium with CH₂CH₂NHCONH₂ substituent] | 200 mg | 1 g | 22 mg |
| 37 | [structure: morpholinium with CH₂CH₂OH substituent] | 150 mg | 500 mg | 22 mg |
| 38 | [structure: morpholinium with CH₂CH(OH)CH₂OH substituent] | 180 mg | 1 g | 20 mg |
| 39 | [structure: morpholinium with CH₂CH(OH)CH₃ substituent] | 160 mg | 1 g | 35 mg |
| 40 | [structure: 4-carbamoylpiperidinium with CH₂CH₂CONH₂ on N] | 298 mg | 1 g | 218 mg |
| 41 | [structure: quinuclidinium with C(CH₃)=N—OH substituent] | 159 mg | 800 mg | 20 mg |
| 42 | [structure: tetrahydropyridinium with N—CH₂CH₂OH and 4-CH=N—OH] | 260 mg | 800 mg | 6 mg |
| 43 | [structure: tetrahydropyridinium with N—CH₂CH₂OH and 4-CONH₂] | 274 mg | 1 g | 80 mg |
| 44 | [structure: (CH₃)₂N⁺(CH₂CH₂OH) dimethylethanolammonium] | 100 mg | 550 mg | 89 mg |

-continued

| Example No. | A | Use amount of the starting compound A' (amine) | Compound of Experiment 4 | Yield of the objective product |
|---|---|---|---|---|
| 45 | −N⁺(CH₃)(CH₂CH₃)CH₂CN | 160 mg | 550 mg | 16 mg |
| 46 | −N⁺(CH₃)(CH₂CH₂OH)CH₂CONH₂ | 220 mg | | 26 mg |
| 47 | −N⁺(CH₃)(CH₂CH₂OH)CH₂COOH | [CH₃−N(CH₂CH₂OH)(CH₂CONH₂)] | 1 g | 19 mg (As by-product of Example 46) |
| 48 | −N⁺(CH₃)(CH₂CONH₂)CH₂CONH₂ | 608 mg | 3 g | 145 mg |
| 49 | −N⁺(CH(OH)CH₂CONH₂)(CH₂CH₂OH) | 913 mg (Hydrochloride) | 2 g | 3 mg |
| 50 | −N⁺(CH₂OH)(CH(OH)CH(OH)CH₃) | 200 mg | 1 g | 23 mg |
| 51 | −N⁺(CH₂OH)(CH₂CH₂OH)CH₂NHCOCH₃ | 200 mg | 1 g | 13 mg |
| 52 | −N⁺(CH₂OH)(CH₂CH₂OH)−N(CH₂CH₂OH)(CH₂CH₂OH) | 194 mg | 500 mg | 46 mg |
| 53 | −N⁺(CH₃)(CH₃)NHCONH₂ | 166 mg | 1 g | 8 mg |
| 54 | −N⁺(CH₃)(CH₃)OH | 2.5 ml | 1 g | 15 mg |
| 55 | −N⁺(CH₃)(CH₃)CH₂CONHCH₃ | 381 mg | 2 g | 250 mg |
| 56 | −N⁺(CH₃)(CH₃)(CH₃)CH₂CON(CH₃)(CH₃) | 111 mg | 500 mg | 87 mg |

-continued

| Example No. | A | A' (amine) | Compound of Experiment 4 | Yield of the objective product |
|---|---|---|---|---|
| 57 | $-\overset{CH_3}{\underset{CH_3}{\overset{|}{\underset{|}{N}}}}-\overset{CH_3}{\underset{CONH_2}{\overset{|}{C}}}-CH_3$ | 250 mg | 800 mg | 63 mg |
| 58 | $-\overset{CH_3}{\underset{CH_3}{\overset{|}{\underset{|}{N}}}}-\overset{CH_3}{\underset{CONHCH_3}{\overset{H}{C}}}$ (wedge) | 157 mg | 750 mg | 52 mg |
| 59 | $-\overset{CH_3}{\underset{CH_3}{\overset{|}{\underset{|}{N}}}}-\overset{CH_3}{\underset{CONHCH_3}{\overset{H}{C}}}$ (dash) | 157 mg | 750 mg | 41 mg |
| 60 | $-\overset{CH_3}{\underset{CH_3}{\overset{|}{\underset{|}{N}}}}-\overset{CONH_2}{\underset{CONH_2}{\overset{H}{C}}}$ (dash) | 445 mg | 2 g | 75 mg |
| 61 | $-\overset{CH_3}{\underset{CH_3}{\overset{|}{\underset{|}{N}}}}-\overset{CONH_2}{\underset{CONH_2}{\overset{H}{C}}}$ (wedge) | 445 mg | 2 g | 268 mg |
| 62 | $-\overset{CH_3}{\underset{CH_3}{\overset{|}{\underset{|}{N}}}}-\overset{OH}{\underset{CONH_2}{\overset{H}{C}}}$ | 3.39 g | 23.8 g | 1.42 g |
| 63 | $-\overset{CH_3}{\underset{CH_3}{\overset{|}{\underset{|}{N}}}}-\overset{OH}{\underset{CONHCH_2OH}{\overset{H}{C}}}$ | 200 mg | 500 mg | 14 mg |
| 64 | $-\overset{CH_3}{\underset{CH_3}{\overset{|}{\underset{|}{N}}}}-CH_2CH_2OH$ | 81 μl | 500 mg | 101 mg |
| 65 | $-\overset{CH_3}{\underset{CH_3}{\overset{|}{\underset{|}{N}}}}-CH_2-\overset{H}{\underset{OH}{\overset{|}{C}}}-CH_3$ | 150 mg | 750 mg | 127 mg |
| 66 | $-\overset{CH_3}{\underset{CH_3}{\overset{|}{\underset{|}{N}}}}-CH_2-\overset{H}{\underset{OH}{\overset{|}{C}}}-CH_3$ | 150 mg | 750 mg | 120 mg |
| 67 | $-\overset{CH_3}{\underset{CH_3}{\overset{|}{\underset{|}{N}}}}-\overset{CH_3}{\underset{CH_2OH}{\overset{H}{C}}}$ | 300 mg | 1 g | 126 mg |
| 68 | $-\overset{CH_3}{\underset{CH_3}{\overset{|}{\underset{|}{N}}}}-\overset{CH_3}{\underset{CH_2OH}{\overset{H}{C}}}$ | 300 mg | 1 g | 126 mg |

-continued

| Example No. | A | Use amount of the starting compound | | Yield of the objective product |
|---|---|---|---|---|
| | | A' (amine) | Compound of Experiment 4 | |
| 69 | −N⁺(CH₃)₃−C(CH₃)₂−OH (trimethylammonio with C(CH₃)₂OH substituent) | 400 mg | 1 g | 35 mg |
| 70 | −N⁺(CH₃)₂−C(CH₂OH)₃ type | 361 mg | 1.5 g | 15 mg |
| 71 | −N⁺(CH₃)₂−CH₂CONHOCH₃ | 71 mg | 500 mg | 6 mg |
| 72 | −N⁺(CH₃)₂−CH₂CONHOH | 301 mg | 800 mg | 25 mg |
| | | [(CH₃)₂N−CH₂CONHO−Tr] | | |
| 73 | −N⁺(CH₃)₂−CH₂CONHCH₂CONH₂ | 150 mg | 800 mg | 52 mg |
| 74 | −N⁺(CH₃)₂−CH₂CON(CH₂CH₂OH)₂ | 110 mg | 500 mg | 74 mg |
| 75 | −N⁺(CH₃)₂−CH₂CONHCH₂CH₂OH | 260 mg | 500 mg | 48 mg |
| 76 | −N⁺(CH₃)₂−CH₂CH₂−N⁺(CH₃)₂−CH₂COO⁻ | 373 mg | 730 mg | 16 mg |
| | | [(CH₃)₂N−CH₂CH₂−N⁺(CH₃)₂−CH₂COO−ᵗBu · Br⁻] | | |
| 77 | −N⁺(CH₃)₂−CH₂CH₂CH₂−N(CH₃)₂ | 158 mg | 800 mg | 88 mg |
| 78 | −N⁺(CH₃)₂−CH₂CH(OH)CH₂−N(CH₃)₂ | 138 mg | 800 mg | 36 mg |
| 79 | DABCO (1,4-diazabicyclo[2.2.2]octane, N⁺-substituted) | 115 mg | 500 mg | 92 mg |

-continued
| Example No. | A | A' (amine) Use amount of the starting compound | Compound of Experiment 4 | Yield of the objective product |
|---|---|---|---|---|
| 80 | 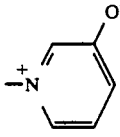 | 70 mg | 500 mg | 4 mg |
| 81 | 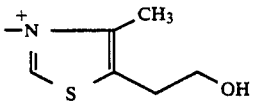 | 131 mg | 500 mg | 30 mg |
| 82 | 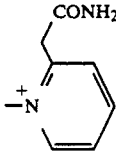 | 270 mg | 750 mg | 70 mg |
| 83 | 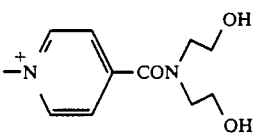 | 335 mg | 750 mg | 67 mg |
| 84 | 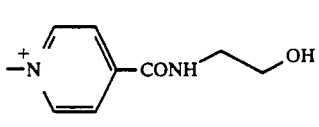 | 268 mg | 750 mg | 65 mg |
| 85 | 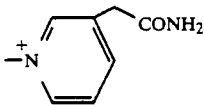 | 220 mg | 750 mg | 32 mg |
| 86 | 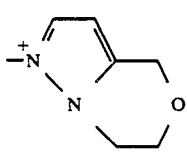 | 300 mg | 1.5 g | 97 mg |
| 87 | 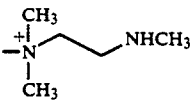 | 326 mg | 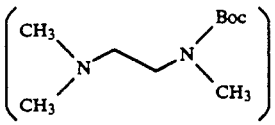 | 1 g | 130 mg |
| 88 | 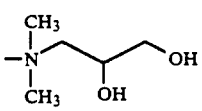 | 192 mg | 1 g | 36 mg |
| 89 | 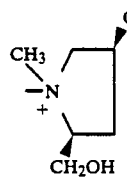 | 250 mg | 1.5 mg | Isomer (89-1) 28 mg<br>Isomer (89-2) 62 mg |
| 90 | 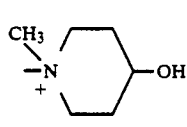 | 156 mg | 1.05 g | 107 mg |

-continued

| Example No. | A | Use amount of the starting compound | | Yield of the objective product |
|---|---|---|---|---|
| | | A' (amine) | Compound of Experiment 4 | |
| 91 | [structure: N-piperidine with 2-hydroxyethyl and 4-OH] | 187 mg | 1 g | 56 mg |
| 92 | [structure: –N+(CH3)2–CH2CONHCH2OH] | 350 mg | 1.2 g | 67 mg |
| 93 | [structure: –N+(CH3)2–CH2CH2CONH2] | 150 mg | 1 g | 97 mg |
| 94 | [structure: N-methylpiperazine with N'-CONH2] | 203 mg | 100 mg | 25 mg |
| 95 | [structure: –N+(CH3)2–CH(CH2OH)2] | 180 mg | 1.2 g | 50 mg |
| 96 | [structure: –N+(CH3)(C2H5)–CH2CONH2 variant] | 420 mg | 2 g | 98 mg |
| 97 | [structure: –N+(CH3)2–CH2CH2CONHCH3] | 90 mg | 600 mg | 7 mg |
| 98 | [structure: –N+(CH3)2–CH2CH2CON(CH3)2] | 90 mg | 600 mg | 7 mg |
| 99 | [structure: –N+(CH3)2–CH2CH2OCH3] | 132 mg | 1 g | 19 mg |
| 100 | [structure: –N+(CH3)2–CH(CH3)–CH(OH)–CH2CONH2 with stereochemistry] | 470 mg | 2 g | 40 mg |
| 101 | [structure: piperidine N+ with 2-hydroxyethyl and N-CONH2] | 391 mg | 1 g | 62 mg |
| 102 | [structure: –N+(CH3)2–CH2-pyrazolyl] | 130 mg | 500 mg | 35 mg |

-continued

| Example No. | A | A' (amine) Use amount | Compound of Experiment 4 | Yield of the objective product |
|---|---|---|---|---|
| 103 | 3-aminopyridinium (−N⁺ pyridine with NH₂) | 150 mg | 500 mg | 30 mg |
| 104 | (CH₃)₂N⁺(−)CH₂CONHSO₂NH₂ | 300 mg | 1 g | 12 mg |
| 105 | (CH₃)₂N⁺(−)CH₂CONHSO₂CH₃ | 150 mg | 500 mg | 12 mg |
| 106 | (CH₃)₂N⁺(−)CH₂-(1H-imidazol-4-yl) | 120 mg | 500 mg | 30 mg |
| 107 | −N⁺(CH₂CH₂OH)₂−NH₂ | 200 mg | 1 g | 15 mg |
| 108 | 3-(morpholinocarbonyl)pyridinium (−N⁺ pyridine-CO-N-morpholine) | 400 mg | 800 mg | 21 mg |
| 109 | 4-(carboxymethoxymethyl)pyridinium (−N⁺ pyridine-CH₂-O-CH₂-COOH) | 720 mg | 1 g | 43 mg |
| 110 | 4-(carboxymethylthio)pyridinium (−N⁺ pyridine-S-CH₂-COOH) | 545 mg | 1 g | 33 mg |
| 111 | 4-(2-carboxyethyl)pyridinium (−N⁺ pyridine-CH₂CH₂-COOH) | 670 mg (pyridine-CH₂CH₂-COO-ᵗBu) | 1 g | 6 mg |
| 112 | 1-(carboxymethyl)pyrrolidinium (−N⁺ pyrrolidine-CH₂-COOH) | 133 mg (Hydrochloride) | 500 mg | 31 mg |
| 113 | 3-(carboxymethyl)pyridinium (−N⁺ pyridine-CH₂-COOH) | 280 mg (Hydrochloride) | 500 mg | 28 mg |

EXAMPLE 114

7β-[2-(5-Amino-1,2,4-thiadiazol-3-yl)-(Z)-2-difluoromethoxyiminoacetamido]-3-[(E)-3-(dimethylcarbamoylmethylammonio)-1-propen-1-yl]-3-cephem-4-carboxylate

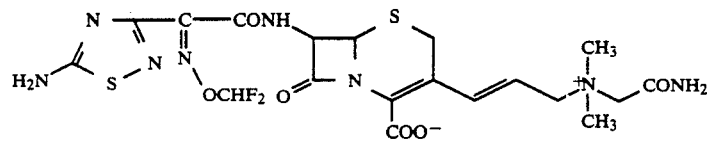

The compound (500 mg) of Experiment 6 was dissolved in a mixed solution of ethyl acetate (10 ml) and ethyl ether (10 ml). To the solution was added dimethylglycine amide (160 mg), followed by stirring for 30 minutes at a room temperature. To the reaction solution was added iso-propyl ether. The resulting precipitate was recovered by filtration, and dried to obtain yellowish brown powder (400 mg).

This powder was stirred under an ice-cooling in a mixed solution of trifluoroacetic acid (5 ml) and anisole (4.5 ml) for one hour. To the reaction solution was added ethyl ether, and the resulting precipitate was recovered by filtration, followed by washing with ethyl ether. This precipitate was suspended in water (5 ml), followed by adjusting its pH to 5.5–6.5 with sodium acetate. The insolubles were removed by filtration, and the filtrate was purified through a reversed phase silica gel chromatography to obtain the object product (55 mg).

In the same manner as described in Example 114, there were produced the compounds of the following Examples 115–117.

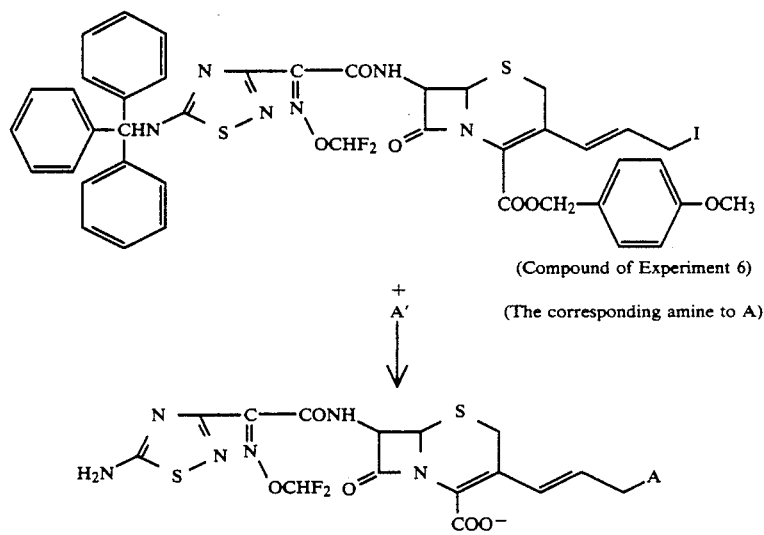

| Example No. | A | Use amount of the starting compound | | Yield of the objective product |
|---|---|---|---|---|
| | | A' (amine) | Compound of Experiment 4 | |
| 115 | —⁺N⃝—COOH | 389 mg | 1 g | 4 mg |
| 116 | —⁺N⌒N | 120 mg | 600 mg | 78 mg |
| 117 | —⁺N(CH₂CH₂OH)₃ | 220 mg | 700 mg | 30 mg |

List of physical data

| | Infrared absorption spectrum (cm$^{-1}$, Nujol) | NMR Spectrum ($\delta$) |
|---|---|---|
| Experiment No. | | |
| 1 | 1735, 1530 | (DMSO-d$_6$) 1.19(3H, t, J=7Hz), 4.21(2H, q, J=7Hz), 5.79(2H, d, J=55Hz), 7.30(15H, s), 10.03(1H, s) |
| 2 | 1720, 1585 | (DMSO-d$_6$) 5.78(2H, d, J=55Hz), 7.31(15H, s), 10.06(1H, s) |
| 3 | 1765, 1725, 1680, 1610 | (DMSO-d$_6$) 3.45(1H, d, J=18Hz), 3.63(1H, d, J=18Hz), 3.75(3H, s), 3.95(1H, dd, J=8Hz, 12Hz), 4.12(1H, dd, J=8Hz, 12Hz), 5.07(1H, d, J=12Hz), 5.14(1H, d, J=12Hz), 5.24(1H, d, J=5Hz), 5.70(1H, m), 5.78(2H, d, J=55Hz), 5.85(1H, m), 6.26(1H, d, J=12Hz), 6.92(2H, d, J=9Hz), 7.25~7.4(17H, m), 9.74(1H, d, J=8Hz), 10.08(1H, s) |
| 4 | 1770, 1715, 1685, 1610 | (CDCl$_3$) 3.51(1H, d, J=18Hz), 3.60(1H, d, J=18Hz), 3.81(3H, s), 3.98(2H, d, J=8Hz), 5.04(1H, d, J=5Hz), 5.19(1H, d, J=12Hz), 5.24(1H, d, J=12Hz), 5.82(2H, d, J=55Hz), 5.90(1H, m), 6.14(1H, dt, J=8Hz, 16Hz), 6.77(1H, d, J=9Hz), 6.90(2H, d, J=9Hz), 7.00(1H, d, J=16Hz), 7.2~7.4(17H, m), 7.83(1H, s) |
| 5 | 1775, 1725, 1690, 1610 | (CDCl$_3$) 3.34(1H, d, J=18.5Hz), 3.52(1H, d, J=18.5Hz), 3.75(1H, dd, J=12.1Hz, 8.5Hz), 3.80(3H, s), 3.93(1H, dd, J=8.5Hz, 12.1Hz), 5.10(1H, d, J=5.0Hz), 5.14(2H, s), 5.74(1H, dt, J=8.5Hz, 11.0Hz), 5.92(1H, dd, J=5.0Hz, 8.8Hz), 6.25(1H, dd, J=11.0Hz), 6.79(1H, d, J=8.8Hz), 6.81(1H, t, J=71.2Hz), 6.87(2H, d, J=8.7Hz), 7.15~7.25(6H, m), 7.29(2H, d, J=8.7Hz), 7.25~7.40(9H, m), 7.67(1H, brs) |
| 6 | 1780, 1720, 1690, 1610 | (CDCl$_3$) 3.51(1H, d, J=17.6Hz), 3.61(1H, d, J=17.6Hz), 3.81(3H, s), 3.98(2H, d, J=8.0Hz), 5.05(1H, d, J=5.0Hz), 5.21(2H, brs), 5.89(1H, dd, J=4.8Hz, 8.8Hz), 6.14(1H, dt, J=8.0Hz, 16.0Hz), 6.78(1H, d, J=8.8Hz); 6.81(1H, t, J=71.2Hz), 6.90(2H, d, J=8.8Hz), 7.00(1H, d, J=16.0Hz), 7.15~7.45(17H, m), 7.63(1H, brs) |
| Example No. | | |
| 1 | 1760, 1675, 1590, 1520 | (DMSO-d$_6$) 1.26(3H, t, J=7.2Hz), 3.08 and 3.09(total 3H, s), 3.4~3.6(2H, m), 3.47(1H, d, J=16.8Hz), 3.65(1H, d, J=16.8Hz), 4.01(2H, s), 4.05~4.2(2H, m), 5.06(1H, d, J=4.8Hz), 5.6~5.75(2H, m), 5.79(2H, brd, J=55.3Hz), 7.17(1H, d, J=15.8Hz), 7.66(1H, s), 8.23(2H, s), 8.33(1H, s), 9.71(1H, d, J=8.4Hz) |
| 2-1 | 1750, 1650, 1590, 1520 | (D$_2$O) 2.18~2.30(4H, m), 2.78~2.83(1H, m), 3.48~3.54(4H, m), 3.73~3.84(4H, m), 4.15~4.18(2H, m), 4.32(2H, m), 5.38(1H, d, J=5.1Hz), 5.94~6.00(1H, m), 5.96(2H, d, J=54.2Hz), 5.97(1H, d, J=5.1Hz), 7.07(1H, d, J=16.8Hz) |
| 2-2 | 1750, 1650, 1590, 1520 | (D$_2$O) 2.19~2.26(4H, m), 2.76~2.81(1H, m), 3.42~3.54(2H, m), 3.65~3.66(2H, m), 3.73~3.83(4H, m), 4.14~4.16(2H, m), 4.24~4.27(2H, m), 5.39(1H, d, J=5.1Hz), 5.96(2H, d, J=54.6Hz), 5.97(1H, d, J=5.1Hz), 5.99~6.07(1H, m), 7.02(1H, d, J=15.8Hz) |
| 3-1 | 1760, 1670, 1590, 1515 | (DMSO-d$_6$) 1.48(3H, d, J=7.0Hz), 3.05(3H, s), 3.08(3H, s), 3.48(1H, d, J=16.7Hz), 3.65(1H, d, J=16.7Hz), 3.97~4.15(3H, m), 5.07(1H, d, J=5.0Hz), 5.66(1H, dd, J=5.0Hz, 8.4Hz), 5.65~5.75(1H, m), 5.78(2H, brd, J=55.5Hz), 7.15(1H, d, J=15.8Hz), 7.70(1H, s), 8.12(2H, s), 8.26(1H, s), 9.70(1H, d, J=8.4Hz) |
| 3-2 | 1760, 1670, 1590, 1520 | (DMSO-d$_6$) 1.46(3H, d, J=7.0Hz), 3.04(3H, s), 3.06(3H, s), 3.49(1H, d, J=17.2Hz), 3.64(1H, d, J=17.2Hz), 4.05(1H, m), 4.15~4.30(2H, m), 5.09(1H, d, J=5.0Hz), 5.67(1H, dd, J=5.0Hz, 8.0Hz), 5.5~5.8(1H, m), 5.79(2H, brd, J=55.5Hz), 7.18(1H, d, J=15.4Hz), 7.67(1H, s), 8.21(2H, s), 8.64(1H, s), 9.70(1H, d, J=8.0Hz) |
| 4 | 1765, 1660, 1600, 1525 | (DMSO-d$_6$) 1.11(3H, d, J=6.2Hz), 3.01(3H, s), 3.04(3H, s), 3.22(2H, brd, J=7.0Hz), 3.46(1H, d, J=17.0Hz), 3.63 and 3.65(total 1H, d, J=17.0Hz), 4.06(2H, brd, J=6.2Hz), 4.26(1H, brs), 5.06(1H, d, J=5.0Hz), 5.6~5.75(2H, m), 5.79(2H, brd, J=55.3Hz), 7.16(1H, d, J=15.8Hz), 8.27(2H, s), 9.71(1H, d, J=8.1Hz) |
| 5 | 1765, 1670, 1600, 1530 | (DMSO-d$_6$) 3.08(3H, s), 3.14(3H, s), 3.49(1H, d, J=17.2Hz), 3.62(1H, d, J=17.2Hz), 3.87(1H, dd, J=5.5Hz, 12.5Hz), 4.06(1H, dd, J=5.5Hz, 12.5Hz), 4.1~4.2(1H, m), 4.19(2H, d, J=7.3Hz), 5.08(1H, d, J=5.0Hz), 5.67(1H, dd, J=4.8Hz, 8.4Hz), 5.70~5.85(1H, m), 5.79(2H, d, J=55.0Hz), 7.11(1H, d, J=15.4Hz), 7.76(1H, s), 8.22(2H, s), 8.52(1H, s), 9.73(1H, d, J=8.4Hz) |
| 6-1 | 1750, 1650, 1590, 1510 | (DMSO-d$_6$) 1.73~1.78(1H, m), 2.54~2.60(1H, m), 3.04(3H, s), 3.44~3.86(5H, m), 3.46(1H, d, J=17.2Hz), 3.62(1H, d, J=17.2Hz), 4.00~4.23(2H, m), 4.43(1H, m), 5.06(1H, d, J=5.1Hz), 5.65(1H, dd, J=5.1Hz, 8.4Hz), 5.71~5.86(3H, m), 7.13(1H, d, J=15.4Hz), 8.22(2H, s), 9.70(1H, d, J=8.4Hz) |
| 6-2 | 1750, 1650, 1590, 1510 | (DMSO-d$_6$) 1.77~1.83(1H, m), 2.53~2.59(1H, m), 3.04(3H, s), 3.32~3.94(5H, m), 3.46(1H, d, J=16.9Hz), 3.65~3.71(1H, m), 3.91~4.19(2H, m), 4.45(1H, m), 5.07(1H, d, J=5.1Hz), 5.64(1H, dd, J=5.1Hz, 8.4Hz), 5.71~5.86(3H, m), 7.14(1H, d, J=15.7Hz), 8.24(2H, s), 9.70(1H, d, J=8.4Hz) |
| 7-1 | 1760, 1665, 1590, 1525 | (DMSO-d$_6$) 2.05(1H, m), 2.31(1H, m), 3.4~3.9(11H, m), 4.01(1H, m), 4.13(1H, m), 4.31(1H, brs), 4.42(1H, brs), 5.07(1H, d, J=4.8Hz), 5.65(1H, dd, J=4.8Hz, 8.4Hz), 5.76(1H, m), 5.78(2H, d, J=56.6Hz), 7.14(1H, d, J=15.4Hz), 8.22(2H, s), 9.70(1H, d, J=8.4Hz) |
| 7-2 | 1760, 1665, | (DMSO-d$_6$) 2.05(1H, m), 2.29(1H, m), 3.4~3.9(11H, m), 3.90~4.35(3H, m), |

-continued

List of physical data

| | Infrared absorption spectrum (cm$^{-1}$, Nujol) | NMR Spectrum ($\delta$) |
|---|---|---|
| | 1590, 1530 | 4.44(1H, brs), 5.07(1H, d, J=4.8Hz), 5.65(1H, dd, J=4.8Hz, 8.1Hz), 5.78(2H, d, J=55.6Hz), 5.79(1H, m), 7.11(1H, d, J=15.4Hz), 8.21(2H, s), 9.71(1H, d, J=8.1Hz) |
| 8 | 1750, 1660, 1590, 1510 | (DMSO-d$_6$) 1.95~2.07(1H, m), 2.17~2.35(1H, m), 2.92 and 3.14(total 3H, s), 3.22~4.03(5H, m), 3.45~3.66(2H, m), 4.03~4.22(2H, m), 4.42(1H, m), 5.07(1H, d, J=4.8Hz), 5.65(1H, dd, J=4.8Hz, 8.1Hz), 5.71~5.86(3H, m), 7.11~7.18(1H, m), 8.22(2H, s), 9.70(1H, d, J=8.1Hz) |
| 9-1 | 1750, 1660, 1590, 1510 | (DMSO-d$_6$) 1.95~1.98(1H, m), 2.30~2.36(1H, m), 3.45(1H, d, J=16.9Hz), 3.59~3.82(5H, m), 4.19(1H, s), 4.24(2H, m), 4.50(1H, m), 5.06(1H, d, J=4.8Hz), 5.65(1H, dd, J=8.1Hz, 4.8Hz), 5.69~5.75(1H, m), 5.79(2H, d, J=55.0Hz), 7.10(1H, d, J=15.8Hz), 7.66(1H, s), 8.10 and 8.12(total 1H, s), 8.22(2H, s), 9.70(1H, d, J=8.1Hz) |
| 9-2 | 1750, 1660, 1590, 1510 | (DMSO-d$_6$) 1.97~1.99(1H, m), 2.40~2.42(1H, m), 3.45(1H, d, J=16.9Hz), 3.60~3.85(5H, m), 4.06(2H, s), 4.18~4.32(2H, m), 4.51(1H, m), 5.06(1H, d, J=4.8Hz), 5.65(1H, dd, J=8.1Hz, 4.8Hz), 5.70~5.85(1H, m), 5.79(2H, d, J=55.3Hz), 7.10(1H, d, J=15.4Hz), 7.66(1H, s), 8.15(1H, s), 8.22(2H, s), 9.70(1H, d, J=8.1Hz) |
| 9-3 | 1750, 1660, 1590, 1510 | (DMSO-d$_6$) 1.95~1.98(1H, m), 2.37~2.42(1H, m), 3.46(1H, d, J=16.9Hz), 3.60~3.83(5H, m), 4.06(2H, s), 4.26(2H, m), 4.52(1H, m), 5.06(1H, d, J=4.8Hz), 5.65(1H, dd, J=8.1Hz, 4.8Hz), 5.72~5.84(1H, m), 5.79(2H, d, J=55.0Hz), 7.10(1H, d, J=15.8Hz), 7.65(1H, s), 8.18(1H, s), 8.22(2H, s), 9.70(1H, d, J=8.1Hz) |
| 10 | 1765, 1670, 1595, 1525 | (DMSO-d$_6$) 2.95(2H, s), 3.0~3.5(8H, m), 3.52(1H, d, J=16.9Hz), 3.76(1H, d, J=16.9Hz), 4.08(2H, m), 5.12(1H, d, J=4.8Hz), 5.71~5.85(3H, m), 7.14(1H, d, J=15.8Hz), 7.16(1H, brs), 8.21(1H, s), 9.74(1H, d, J=8.1Hz) |
| 11 | 1760, 1650, 1590, 1530 | (DMSO-d$_6$) 1.74(2H, brs), 2.01(2H, brs), 3.2~3.8(6H, m), 3.81(1H, s), 4.02(2H, s), 4.28(2H, s), 5.05 and 5.06(total 1H, d, J=5.1Hz), 5.6~5.8(1H, m), 5.64(1H, dd, J=5.1Hz, 8.1Hz), 5.78(2H, d, J=55.3Hz), 7.14(1H, d, J=15.8Hz), 7.71(1H, s), 8.22(3H, s), 9.69(1H, d, J=8.1Hz) |
| 12 | 1750, 1660, 1610, 1590 | (DMSO-d$_6$) 1.35(3H, s), 3.1~4.0(12H, m), 4.1~4.3(1H, m), 4.50(2H, d, J=3.6Hz), 5.07(1H, d, J=4.8Hz), 5.6~5.8(2H, m), 5.76(2H, d, J=52.0Hz), 7.15(1H, d, J=15.7Hz), 8.22(2H, s), 9.70(1H, d, J=8.0Hz) |
| 13-1 | 1760, 1670, 1590, 1520 | (DMSO-d$_6$) 1.50(3H, d, J=6.6Hz), 2.00(4H, brs), 3.47(1H, d, J=17.0Hz), 3.45~3.70(3H, m), 3.63(1H, d, J=17.0Hz), 3.85~3.95(1H, m), 4.07(2H, m), 4.15~4.25(1H, m), 5.07(1H, d, J=4.8Hz), 5.65(1H, dd, J=4.8Hz, 8.0Hz), 5.7~5.8(1H, m), 5.78(2H, d, J=55.0Hz), 7.16(1H, d, J=15.8Hz), 7.69(1H, s), 8.23(2H, s), 8.36(1H, s), 9.71(1H, d, J=8.0Hz) |
| 13-2 | 1765, 1680, 1600, 1525 | (DMSO-d$_6$) 1.49(3H, d, J=6.6Hz), 2.00(4H, brs), 3.47(1H, d, J=17.0Hz), 3.5~3.70(3H, m), 3.59(1H, d, J=17.0Hz), 3.8~3.9(1H, m), 4.07(2H, m), 4.25~4.35(1H, m), 5.07(1H, d, J=5.0Hz), 5.66(1H, dd, J=5.0Hz, 8.4Hz), 5.70~5.85(1H, m), 5.78(2H, d, J=55.0Hz), 7.16(1H, d, J=15.4Hz), 7.69(1H, s), 8.22(2H, s), 8.50(1H, s), 9.70(1H, d, J=8.4Hz) |
| 14 | 1765, 1665, 1595, 1520 | (D$_2$O) 2.35~2.45(2H, m), 3.75~4.0(6H, m), 4.3~4.4(2H, m), 4.73(2H, s), 5.40(1H, d, J=4.8Hz), 5.96(2H, d, J=54.5Hz), 5.98(1H, d, J=4.8Hz), 6.09(1H, dt, J=8.0Hz, 15.8Hz), 7.15(1H, d, J=15.8Hz) |
| 15-1 | 1750, 1650, 1590, 1510 | (DMSO-d$_6$) 1.91~1.96(1H, m), 2.32~2.41(1H, m), 3.31~3.99(10H, m), 3.99~4.24(2H, m), 4.50(1H, m), 5.06(1H, d, J=4.8Hz), 5.65(1H, dd, J=4.8Hz, 8.1Hz), 5.66~5.72(1H, m), 5.79(2H, d, J=55.3Hz), 7.16(1H, d, J=15.8Hz), 8.21(2H, s), 9.70(1H, d, J=8.1Hz) |
| 15-2 | 1750, 1650, 1590, 1510 | (DMSO-d$_6$) 1.93~1.97(1H, m), 2.35~2.42(1H, m), 3.34~3.82(10H, m), 4.09~4.23(2H, m), 4.51(1H, m), 5.07(1H, d, J=4.8Hz), 5.65(1H, dd, J=4.8Hz, 8.1Hz), 5.72~5.82(1H, m), 5.79(2H, d, J=53.9Hz), 7.15(1H, d, J=15.8Hz), 8.21(2H, s), 9.70(1H, d, J=8.1Hz) |
| 16 | 1740, 1640, 1580 | (DMSO-d$_6$) 1.8~2.3(4H, m), 3.4~4.2(11H, m), 3.97~4.13(2H, m), 5.07(1H, d, J=5.1Hz), 5.64(1H, dd, J=5.1Hz, 8.4Hz), 5.71~5.78(1H, m), 5.79(2H, d, J=55.3Hz), 7.15 and 7.16(total 1H, d, J=15.8Hz), 8.22(2H, s), 9.70(1H, d, J=8.4Hz) |
| 17 | 1750, 1660, 1590 | (DMSO-d$_6$) 1.8~2.3(4H, m), 3.3~4.4(9H, m), 4.01~4.29(2H, m), 5.07(1H, d, J=4.8Hz), 5.66(1H, dd, J=4.8Hz, 8.1Hz), 5.76(1H, m), 5.78(1H, d, J=57.5Hz), 7.14(1H, d, J=15.4Hz), 7.61(1H, s), 8.21(1H, s), 8.24(2H, s), 9.72(1H, d, J=8.1Hz) |
| 18 | 1760, 1650, 1600, 1520 | (DMSO-d$_6$) 1.92~2.20(4H, m), 3.40~3.75(4H, m), 3.43~3.75(2H, m), 3.86(1H, m), 4.08(1H, m), 4.66(1H, m), 5.05(1H, d, J=4.8Hz), 5.63(1H, dd, J=8.4Hz, 4.8Hz), 5.68~5.76(1H, m), 5.79(2H, d, J=55.3Hz), 7.12(1H, d, J=15.8Hz), 8.22(2H, s), 9.71(1H, d, J=8.4Hz) |
| 19 | — | (DMSO-d$_6$) 2.06(4H, brs), 3.45(1H, d, J=17.2Hz), 3.5~3.7(5H, m), 4.05(2H, s), 4.13(2H, brs), 5.06(1H, d, J=4.8Hz), 5.65(1H, dd, J=4.8Hz, 8.0Hz), 5.65~5.8(1H, m), 5.78(2H, brd, J=55.0Hz), 7.12(1H, d, J=16.2Hz), 7.66(1H, s), 8.23(3H, s), 9.70(1H, d, J=8.0Hz) |
| 20 | — | (DMSO-d$_6$) 2.05(4H, brs), 3.44(1H, d, J=16.8Hz), 3.50(6H, brs), 3.63(1H, d, J=16.8Hz), 4.8~4.9(2H, m), 4.01(2H, d, J=7.3Hz), 5.06(1H, d, J=5.0Hz), 5.64(1H, dd, J=5.0Hz, 8.0Hz), 5.7~5.8(1H, m), 5.78(2H, brd, J=56.0Hz), 7.17(1H, d, J=15.8Hz), 8.23(2H, s), 9.70(1H, d, J=8.0Hz) |
| 21 | — | (DMSO-d$_6$) 1.75~2.25(4H, m), 2.88(1H, s), 3.06(2H, s), 3.2~4.3(9H, m), 3.45(1H, d, J=16.9Hz), 3.68(1H, d, J=16.9Hz), 5.05(1H, d, J=4.8Hz), 5.6~5.8(1H, m), 5.63(1H, dd, J=4.8Hz, 8.4Hz), 5.78(2H, d, J=58.6Hz), |

-continued

List of physical data

| | Infrared absorption spectrum (cm$^{-1}$, Nujol) | NMR Spectrum ($\delta$) |
|---|---|---|
| | | 7.15 and 7.18(total 1H, d, J=15.4Hz), 8.23(2H, s), 9.69(1H, d, J=8.4Hz) |
| 22 | — | (D$_2$O) 2.34(4H, s), 3.5~3.9(10H, m), 4.17(2H, d, J=7.7Hz), 5.39(1H, d, J=4.8Hz), 5.97(1H, d, J=4.8Hz), 5.97(2H, d, J=54.6Hz), 6.00~6.15(1H, m), 7.07(1H, d, J=15.8Hz) |
| 23-1 | 1750, 1650, 1580 | (DMSO-d$_6$) 2.06~2.08(3H, m), 3.21~3.63(12H, m), 4.02~4.08(2H, m), 5.08(1H, d, J=5.1Hz), 5.66(1H, dd, J=5.1Hz, 8.1Hz), 5.71~5.76(1H, m), 5.79(2H, d, J=55.3Hz), 7.13(1H, d, J=15.8Hz), 8.21(2H, s), 9.71(1H, d, J=8.1Hz) |
| 23-2 | 1750, 1650, 1580 | (DMSO-d$_6$) 2.08(3H, m), 2.98~3.07(2H, m), 3.36~3.80(9H, m), 3.98~4.02(1H, m), 4.07~4.12(2H, m), 5.06(1H, d, J=4.8Hz), 5.66(1H, dd, J=4.8Hz, 8.1Hz), 5.71~5.85(3H, m), 7.06(1H, d, J=15.8Hz), 8.20(2H, s), 9.75(1H, d, J=8.1Hz) |
| 24 | 1765, 1650, 1595, 1525 | (DMSO-d$_6$) 3.06(3H, s), 3.3~3.5(4H, m), 3.46(1H, d, J=16.9Hz), 3.5~4.0(4H, m), 3.64(1H, d, J=16.9Hz), 4.15(2H, m), 5.06(1H, d, J=4.8Hz), 5.6~5.8(1H, m), 5.64(1H, dd, J=4.8Hz, 8.4Hz), 5.79(2H, d, J=57.2Hz), 7.22(1H, d, J=15.8Hz), 8.08(1H, s), 8.23(2H, s), 9.70(1H, d, J=8.4Hz) |
| 25 | 1750, 1650, 1620, 1580 | (DMSO-d$_6$) 2.55~2.90(10H, m), 2.97(3H, s), 3.1~3.5(2H, m), 3.48(1H, d, J=17.6Hz), 3.75(1H, d, J=17.6Hz), 4.0~4.2(2H, m), 5.12(1H, d, J=5.1Hz), 5.65~5.80(1H, m), 5.80~5.90(1H, m), 5.79(2H, d, J=55.3Hz), 7.11(1H, d, J=15.8Hz), 8.21(2H, s), 9.73(1H, d, J=8.1Hz) |
| 26 | 1765, 1670, 1590, 1530 | (DMSO-d$_6$) 2.28(3H, s), 3.10(3H, s), 3.46(1H, d, J=16.9Hz), 3.6~4.1(8H, m), 3.64(1H, d, J=16.9Hz), 4.16(2H, m), 5.07(1H, d, J=4.8Hz), 5.6~5.8(1H, m), 5.79(2H, d, J=57.2Hz), 5.66(1H, dd, J=4.8Hz, 7.7Hz), 7.22(1H, d, J=15.4Hz), 8,23(2H, s), 9.70(1H, d, J=7.7Hz) |
| 27 | 1760, 1660, 1590, 1520 | (DMSO-d$_6$) 2.49~3.85(16H, m), 3.42~3.51(1H, m), 3.66(1H, d, J=17.2Hz), 4.17(2H, d, J=6.6Hz), 5.06(1H, d, J=4.8Hz), 5.6~5.9(1H, m), 5.64(1H, dd, J=4.8Hz, 8.1Hz), 5.79(2H, d, J=55.3Hz), 7.17(1H, d, J=15.8Hz), 8.24(2H, s), 9.70(1H, d, J=8.1Hz) |
| 28 | 1750, 1650, 1580 | (D$_2$O) 3.6~3.85(8H, m), 3.85~3.97(4H, m), 4.19(2H, t, J=4.8Hz), 4.39(2H, m), 5.39(1H, d, J=4.8Hz), 5.96(2H, d, J=54.2Hz), 5.97(1H, d, J=4.8Hz), 6.0~6.08(1H, m), 7.06(1H, d, J=15.7Hz) |
| 29 | 1750, 1660, 1580 | (DMSO-d$_6$) 3.2~3.7(12H, m), 3.8(2H, m), 4.22(2H, d, J=7.3Hz), 5.08(1H, d, J=5.1Hz), 5.6~5.8(2H, m), 5.79(2H, d, J=55.7Hz), 7.13(2H, s), 7.18(1H, d, J=15.8Hz), 8.22(2H, s), 9.70(1H, d, J=8.0Hz) |
| 30 | — | (D$_2$O) 3.5~4.0(14H, m), 4.35~4.55(3H, m), 5.38(1H, d, J=4.7Hz), 5.95(2H, d, J=54.2Hz), 5.97(1H, d, J=4.7Hz), 6.0~6.5(1H, m), 7.06(1H, d, J=15.4Hz) |
| 31 | 1750, 1650, 1580 | (D$_2$O) 3.75~4.00(10H, m), 4.23(1H, d, J=16.4Hz), 4.30(1H, d, J=16.4Hz), 4.53(2H, d, J=8.1Hz), 5.39(1H, d, J=4.8Hz), 5.95(2H, d, J=54.2Hz), 5.97(1H, d, J=4.8Hz), 6.0~6.05(1H, m), 7.05(1H, d, J=15.8Hz) |
| 32 | 1750, 1640, 1580 | (D$_2$O) 3.55~4.0(14H, m), 4.25~4.40(2H, m), 5.39(1H, d, J=4.7Hz), 5.97(1H, d, J=4.7Hz), 5.98(2H, d, J=53.4Hz), 6.04(1H, m), 7.08(1H, d, J=15.7Hz) |
| 33 | 1750, 1660, 1620, 1580 | (DMSO-d$_6$) 2.8~3.4(10H, m), 2.97(3H, s), 3.46(1H, d, J=17.2Hz), 3.63(1H, d, J=17.2Hz), 4.07(2H, m), 5.06(1H, d, J=5.1Hz), 5.6~5.9(4H, m), 7.20(1H, d, J=15.8Hz), 8.24(2H, s), 9.70(1H, brs) |
| 34 | 1750, 1660, 1620, 1580 | (DMSO-d$_6$) 2.3~3.4(12H, m), 2.97(3H, s), 3.44(1H, d, J=17.2Hz), 3.62(1H, d, J=17.2Hz), 4.07(2H, brs), 5.05(1H, d, J=4.8Hz), 5.63(2H, m), 5.78(2H, d, J=55.5Hz), 7.20(1H, d, J=15.4Hz), 8.21(2H, s), 9.69(1H, d, J=8.8Hz) |
| 35 | 1750, 1660, 1620, 1590 | (DMSO-d$_6$) 3.4~3.8(6H, m), 3.9~4.05(4H, m), 4.15(1H, d, J=16.1Hz), 4.20(1H, d, J=16.1Hz), 4.37(1H, d, J=7.3Hz), 5.08(1H, d, J=4.7Hz), 5.65~5.8(2H, m), 5.79(2H, d, J=55.3Hz), 7.13(1H, d, J=15.7Hz), 8.21(3H, s), 8.24(1H, s), 9.70(1H, d, J=8.1Hz) |
| 36 | 1750, 1650, 1610, 1590 | (DMSO-d$_6$) 3.2~3.6(10H, m), 3.8~4.0(4H, m), 4.1~4.3(2H, m), 5.11(1H, d, J=4.7Hz), 5.80(2H, d, J=62.0Hz), 5.80~5.95(2H, m), 7.12(1H, d, J=16.0Hz), 8.21(2H, s) |
| 37 | — | (D$_2$O) 3.65~3.82(8H, m), 4.20~4.35(6H, m), 4.38~4.50(2H, m), 5.41(1H, d, J=4.8Hz), 5.98(2H, d, J=54.6Hz), 5.99(1H, d, J=4.8Hz), 6.00~6.10(1H, m), 7.08(1H, d, J=15.8Hz) |
| 38 | — | (D$_2$O) 3.55~3.90(10H, m), 4.14~4.24(4H, m), 4.35~4.55(3H, m), 5.38(1H, d, J=4.8Hz), 5.97(1H, d, J=4.8Hz), 5.96(2H, d, J=54.22Hz), 5.95~6.05(1H, m), 7.07(1H, d, J=15.3Hz) |
| 39 | — | (DMSO-d$_6$) 1.14 and 1.16(total 3H, d, J=6.6Hz), 3.2~3.7(8H, m), 3.85~4.00(4H, m), 4.2~4.45(3H, m), 5.05 and 5.06(total 1H, d, J=4.8Hz), 5.6~5.7(2H, m), 5.75(2H, d, J=55.3Hz), 7.18 and 7.20(total 1H, d, J=15.8Hz), 8.23(2H, s), 9.67(1H, d, J=8.4Hz) |
| 40 | 1760, 1660, 1590, 1520 | (DMSO-d$_6$) 1.95~2.03(4H, m), 2.40(1H, m), 3.4~4.8(4H, m), 4.00~4.05(2H, m), 4.25(2H, m), 5.05(1H, d, J=4.8Hz), 5.6~5.8(2H, m), 5.79(2H, d, J=55.3Hz), 6.99~8.29(4H, m), 7.14(1H, d, J=16.0Hz), 8.22(2H, s), 9.70(1H, d, J=8.1Hz) |
| 41 | 1750, 1660, 1580 | (DMSO-d$_6$) 1.73(3H, s), 1.95(6H, m), 3.41(6H, m), 3.47(1H, d, J=16.9Hz), 3.64(1H, d, J=16.9Hz), 3.89(2H, brs), 5.08(1H, d, J=4.8Hz), 5.66(1H, dd, J=4.8Hz, 8.4Hz), 5.70(1H, m), 5.79(2H, d, J=55.1Hz), 7.14(1H, d, J=15.8Hz), 8.21(2H, s), 9.70(1H, d, J=8.4Hz), 10.73(1H, s) |
| 42 | 1750, 1650, | (DMSO-d$_6$) 2.61(2H, brs), 3.2~3.65(4H, m), 3.47(1H, d, J=17.2Hz), |

-continued
List of physical data

| | Infrared absorption spectrum (cm$^{-1}$, Nujol) | NMR Spectrum (δ) |
|---|---|---|
| | 1580 | 3.69(1H, d, J=17.2Hz), 3.87(2H, t, J=4.8Hz), 4.0~4.2(4H, m), 5.07(1H, d, J=5.1Hz), 5.60~5.85(1H, m), 5.66(1H, dd, J=5.1Hz, 8.1Hz), 5.79(2H, d, J=53.1Hz), 6.08(1H, s), 7.18(1H, d, J=15.8Hz), 7.85(1H, s), 8.21(2H, s), 9.70(1H, d, J=8.1Hz) |
| 43 | 1750, 1660, 1580 | (DMSO-d$_6$) 2.61(2H, s), 3.2~3.7(4H, m), 3.47(1H, d, J=17.6Hz), 3.67(1H, d, J=17.6Hz), 3.87(2H, m), 4.08(4H, m), 5.06(1H, d, J=5.1Hz), 5.40~5.90(2H, m), 5.66(1H, dd, J=5.1Hz, 8.1Hz), 5.79(2H, d, J=58.6Hz), 6.48(1H, s), 7.19(1H, d, J=18.0Hz), 7.21(1H, s), 7.61 and 7.67(total 1H, s), 8.22(2H, s), 9.69 and 9.71(total 1H, d, J=8.1Hz) |
| 44 | 1760, 1660, 1600, 1520 | (DMSO-d$_6$) 1.24(3H, t, J=7.2Hz), 2.94(3H, s), 3.29(4H, brs), 3.45(1H, d, J=16.9Hz), 3.65(1H, d, J=16.9Hz), 3.83(2H, brs), 4.00(2H, brs), 5.06(1H, d, J=4.8Hz), 5.6~5.75(2H, m), 5.78(2H, brd, J=55.5Hz), 7.17(1H, d, J=15.8Hz), 8.24(2H, s), 9.70(1H, d, J=8.0Hz) |
| 45 | 1760, 1660, 1600, 1520 | (D$_2$O) 1.55(3H, t, J=7.3Hz), 3.32(3H, s), 3.71(2H, q, J=7.3Hz), 3.78(1H, d, J=17.2Hz), 3.83(1H, d, J=17.2Hz), 4.32(2H, brd, J=7.3Hz), 4.72(2H, s), 5.41(1H, d, J=4.8Hz), 5.97(2H, d, J=54.5Hz), 5.99(1H, d, J=4.8Hz), 6.0~6.1(1H, m), 7.14(1H, d, J=15.4Hz) |
| 46 | 1750, 1660, 1590, 1520 | (DMSO-d$_6$) 3.10~3.87(4H, m), 3.17(3H, s), 3.49(1H, d, J=17.2Hz), 3.68(1H, d, J=17.2Hz), 4.09(2H, s), 4.26(2H, d, J=7.0Hz), 5.08(1H, d, J=4.8Hz), 5.6~5.9(3H, m), 5.67(1H, dd, J=4.8Hz, 8.4Hz), 7.14(1H, d, J=15.3Hz), 7.62(1H, s), 8.17(1H, s), 8.22(2H, s), 9.72(1H, d, J=8.4Hz) |
| 47 | 1750, 1650, 1600, 1510 | (DMSO-d$_6$) 3.10 and 3.12(total 3H, s), 3.53~3.92(8H, m), 4.33(2H, m), 5.18(1H, d, J=4.8Hz), 5.79(2H, d, J=57.2Hz), 5.80(1H, dd, J=4.8Hz, 8.4Hz), 6.03(1H, m), 7.01(1H, d, J=15.8Hz), 8.22(2H, s), 9.79(1H, d, J=8.4Hz) |
| 48 | 1765, 1680, 1595, 1525 | (DMSO-d$_6$) 3.27(3H, s), 3.50(1H, d, J=17.6Hz), 3.69(1H, d, J=17.6Hz), 4.28(4H, s), 4.37(2H, m), 5.09(1H, d, J=4.8Hz), 5.68(1H, dd, J=4.8Hz, 8.4Hz), 5.74(1H, m), 5.79(2H, d, J=55.3Hz), 7.14(1H, d, J=15.4Hz), 7.66(2H, s), 8.11(1H, s), 8.14(2H, s), 9.72(1H, d, J=8.4Hz) |
| 49 | 1765, 1670, 1595, 1510 | (DMSO-d$_6$) 2.63(2H, m), 3.2~3.7(4H, m), 3.73(1H, d, J=16.9Hz), 3.84(4H, s), 4.07(2H, m), 5.07(1H, d, J=4.8Hz), 5.43(1H, m), 5.60(1H, dd, J=4.8Hz, 8.1Hz), 5.73(1H, m), 5.80(2H, d, J=54.6Hz), 7.06(1H, s), 7.20(1H, d, J=15.8Hz), 7.89(1H, s), 8.21(2H, s), 9.52(1H, d, J=8.1Hz) |
| 50 | 1750, 1650, 1610, 1580 | (D$_2$O) 1.33 and 1.35(total 3H, d, J=6.2Hz), 3.50~3.65(2H, m), 3.65~3.85(6H, m), 4.1~4.2(4H, m), 4.3~4.55(2H, m), 4.55(1H, m), 5.38(1H, d, J=4.7Hz), 5.95(2H, d, J=54.1Hz), 5.97(1H, d, J=4.7Hz), 6.02(1H, m), 7.02(1H, d, J=15.8Hz) |
| 51 | — | (D$_2$O) 2.09(3H, s), 3.55~3.85(10H, m), 4.15(4H, brs), 4.32(2H, d, J=7.7Hz), 5.38(1H, d, J=4.7Hz), 5.95(2H, d, J=55.0Hz), 5.97(1H, d, J=4.7Hz), 6.05(1H, m), 7.05(1H, d, J=15.7Hz) |
| 52 | 1750, 1720, 1650, 1580 | (DMSO-d$_6$) 2.5~3.5(21H, m), 3.64(1H, d, J=16.9Hz), 4.11(2H, d, J=6.6Hz), 5.07(1H, d, J=5.1Hz), 5.6~5.9(3H, m), 5.65(1H, dd, J=5.1Hz, 8.4Hz), 7.16(1H, d, J=15.8Hz), 8.21(2H, s), 9.74(1H, d, J=8.4Hz) |
| 53 | 1750, 1660, 1610, 1580 | (D$_2$O) 3.46(3H, s), 3.50(3H, s), 3.63(2H, s), 4.2~4.6(2H, m), 5.21(1H, d, J=6.0Hz), 5.78(1H, d, J=6.0Hz), 5.78(2H, d, J=60.0Hz), 5.80(1H, m), 6.85(1H, d, J=17.0Hz) |
| 54 | — | (DMSO-d$_6$) 3.32(6H, s), 3.54(1H, d, J=17.5Hz), 3.75(1H, d, J=17.5Hz), 4.44(2H, m), 5.15(1H, d, J=4.6Hz), 5.7~6.0(3H, m), 7.16(1H, d, J=15.4Hz), 8.21(2H, s), 9.76(1H, d, J=8.8Hz) |
| 55 | 1760, 1670, 1640, 1590, 1520 | (DMSO-d$_6$) 2.64(3H, d, J=4.4Hz), 3.13(3H, s), 3.16(3H, s), 3.48(1H, d, J=17.2Hz), 3.65(1H, d, J=17.2Hz), 4.03~4.18(4H, m), 5.07(1H, d, J=4.8Hz), 5.64~5.84(1H, m), 5.66(1H, dd, J=4.8Hz, 8.4Hz), 5.78(2H, d, J=56.4Hz), 7.17(1H, d, J=15.4Hz), 8.23(2H, s), 9.19(1H, d, J=4.4Hz), 9.71(1H, d, J=8.4Hz) |
| 56 | 1760, 1650, 1600, 1520 | (DMSO-d$_6$) 2.88(3H, s), 2.94(3H, s), 3.15(6H, s), 3.45(1H, d, J=16.9Hz), 3.63(1H, d, J=16.9Hz), 4.20(2H, d, J=7.7Hz), 4.34(2H, s), 5.05(1H, d, J=5.1Hz), 5.6~5.7(1H, m), 5.63(1H, dd, J=5.1Hz, 8.1Hz), 5.71~5.85(2H, m), 7.14(1H, d, J=15.8Hz), 8.24(2H, s), 9.70(1H, d, J=8.1Hz) |
| 57 | 1765, 1670, 1600, 1520 | (D$_2$O) 1.87(6H, s), 3.18(6H, s), 3.78(1H, d, J=17.5Hz), 3.84(1H, d, J=17.5Hz), 4.26(2H, d, J=7.3Hz), 5.40(1H, d, J=4.8Hz), 5.97(2H, d, J=54.2Hz), 5.98(1H, d, J=4.8Hz), 6.08(1H, dd, J=15.8Hz, 7.3Hz), 7.03(1H, d, J=15.8Hz) |
| 58 | 1765, 1665, 1600, 1525 | (DMSO-d$_6$) 1.46(3H, d, J=6.6Hz), 2.64(3H, d, J=4.8Hz), 3.04(3H, s), 3.08(3H, s), 3.50(1H, d, J=17.0Hz), 3.65(1H, d, J=17.0Hz), 4.0~4.2(2H, m), 4.25~4.35(1H, m), 5.08(1H, d, J=5.0Hz), 5.66(1H, dd, J=5.0Hz, 8.0Hz), 5.7~5.8(1H, m), 5.78(2H, d, J=55.0Hz), 7.17(1H, d, J=15.4Hz), 8.22(2H, s), 9.13(1H, brs), 9.73(1H, d, J=8.0Hz) |
| 59 | 1765, 1670, 1600, 1525 | (DMSO-d$_6$) 1.44(3H, d, J=7.0Hz), 2.65(3H, d, J=4.5Hz), 3.00(3H, s), 3.06(3H, s), 3.50(1H, d, J=17.0Hz), 3.68(1H, d, J=17.0Hz), 3.9~4.0(1H, m), 4.3~4.5(2H, m), 5.11(1H, d, J=4.8Hz), 5.65~5.80(2H, m), 5.78(2H, d, J=55.0Hz), 7.26(1H, d, J=15.4Hz), 8.21(2H, s), 9.71(1H, d, J=8.0Hz), 9.79(1H, brs) |
| 60 | 1760, 1670, 1595, 1515 | (DMSO-d$_6$) 2.77(2H, m), 3.03(6H, s), 3.48(1H, d, J=16.9Hz), 3.66(1H, d, J=16.9Hz), 4.10(2H, m), 4.26(1H, d, J=7.7Hz), 5.08(1H, d, J=4.8Hz), 5.66(1H, dd, J=4.8Hz, 8.4Hz), 5.76(1H, m), 5.79(2H, d, J=55.0Hz), 7.14(1H, s), 7.20(1H, d, J=15.8Hz), 7.82(2H, s), 8.22(2H, s), 8.27(1H, s), 9.72(1H, d, J=8.4Hz) |

|   | Infrared absorption spectrum (cm$^{-1}$, Nujol) | NMR Spectrum (δ) |
|---|---|---|
| 61 | 1765, 1675, 1595, 1525 | (DMSO-d$_6$) 2.77(2H, m), 3.02(3H, s), 3.03(3H, s), 3.49(1H, d, J=16.9Hz), 3.62(1H, d, J=16.9Hz), 4.10(2H, m), 4.32(1H, d, J=7.7Hz), 5.09(1H, d, J=5.1Hz), 5.66(1H, dd, J=5.1Hz, 8.1Hz), 5.75(1H, m), 5.79(2H, d, J=56.8Hz), 7.16(1H, d, J=15.0Hz), 7.18(1H, s), 7.71(1H, s), 7.83(1H, s), 8.22(2H, s), 8.33(1H, s), 9.72(1H, d, J=8.1Hz) |
| 62 | 1765, 1680, 1590, 1525 | (DMSO-d$_6$) 3.07(3H, s), 3.14(3H, s), 3.47(1H, d, J=16.9Hz), 3.67(1H, d, J=16.9Hz), 3.86(1H, dd, J=5.9Hz, 12.1Hz), 4.01(1H, t, J=5.9Hz), 4.08(1H, dd, J=5.9Hz, 12.1Hz), 4.18(2H, m), 5.07(1H, d, J=5.1Hz), 5.67(1H, dd, J=5.1Hz, 8.1Hz), 5.76(1H, m), 5.78(2H, d, J=55.2Hz), 7.13(1H, d, J=15.8Hz), 7.76(1H, s), 8.22(2H, s), 8.33(1H, s), 9.70(1H, d, J=8.1Hz) |
| 63 | — | (DMSO-d$_6$) 3.17(3H, s), 3.18(3H, s), 3.47(1H, d, J=17.0Hz), 3.67(1H, d, J=17.0Hz), 3.85~3.95(1H, m), 3.95~4.10(2H, m), 4.10~4.25(2H, m), 4.35~4.45(1H, m), 4.75~4.85(1H, m), 5.08(1H, d, J=4.8Hz), 5.67(1H, dd, J=4.8Hz, 8.0Hz), 5.70~5.85(1H, m), 5.79(2H, d, J=55Hz), 7.05(1H, d, J=15.4Hz), 8.21(2H, s), 9.31(1H, brs), 9.71(1H, d, J=8.0Hz) |
| 64 | — | (DMSO-d$_6$) 3.01(6H, s), 3.2~3.5(2H, m), 3.46(1H, d, J=16.9Hz), 3.64(1H, d, J=16.9Hz), 3.84(2H, brs), 4.03(2H, d, J=7.3Hz), 5.06(1H, d, J=4.8Hz), 5.50~5.75(1H, m), 5.64(1H, dd, J=4.8Hz, 8.1Hz), 5.78(2H, d, J=55.1Hz), 7.16(1H, d, J=15.8Hz), 8.24(2H, s), 9.71(1H, d, J=8.1Hz) |
| 65 | 1765, 1660, 1600, 1525 | (DMSO-d$_6$) 1.11(3H, d, J=6.2Hz), 3.01(3H, s), 3.04(3H, s), 3.22(2H, brd, J=7.0Hz), 3.46(1H, d, J=17.0Hz), 3.65(1H, d, J=17.0Hz), 4.06(2H, brd, J=6.2Hz), 4.26(1H, brs), 5.06(1H, d, J=5.0Hz), 5.6~5.75(2H, m), 5.79(2H, brd, J=55.3Hz), 7.16(1H, d, J=15.8Hz), 8.27(2H, s), 9.71(1H, d, J=8.1Hz) |
| 66 | 1765, 1660, 1600, 1525 | (DMSO-d$_6$) 1.11(3H, d, J=6.2Hz), 3.01(3H, s), 3.04(3H, s), 3.22(2H, brd, J=7.0Hz), 3.46(1H, d, J=17.0Hz), 3.63(1H, d, J=17.0Hz), 4.06(2H, brd, J=6.2Hz), 4.26(1H, brs), 5.06(1H, d, J=5.0Hz), 5.6~5.75(2H, m), 5.79(2H, brd, J=55.3Hz), 7.16(1H, d, J=15.8Hz), 8.27(2H, s), 9.71(1H, d, J=8.1Hz) |
| 67 | 1765, 1670, 1600, 1530 | (DMSO-d$_6$) 1.32(3H, d, J=6.6Hz), 2.93(3H, s), 2.98(3H, s), 3.4~3.5(1H, m), 3.46(1H, d, J=17.0Hz), 3.64(1H, d, J=17.0Hz), 3.65~3.85(2H, m), 4.04(2H, d, J=7.3Hz), 5.06(1H, d, J=5.0Hz), 5.6~5.8(2H, m), 5.79(2H, d, J=55.0Hz), 7.18(1H, d, J=15.8Hz), 8.23(2H, s), 9.70(1H, d, J=8.0Hz) |
| 68 | 1765, 1670, 1600, 1525 | (DMSO-d$_6$) 1.32(3H, d, J=6.6Hz), 2.93(3H, s), 2.96(3H, s), 3.4~3.5(1H, m), 3.45(1H, d, J=17.2Hz), 3.65(1H, d, J=17.2Hz), 3.7~3.8(2H, m), 4.07(2H, m), 5.06(1H, d, J=5.0Hz), 5.6~5.75(2H, m), 5.78(2H, d, J=55.0Hz), 7.16(1H, d, J=15.8Hz), 8.24(2H, s), 9.70(1H, d, J=8.4Hz) |
| 69 | 1760, 1660, 1595, 1520 | (DMSO-d$_6$) 1.36(6H, s), 2.88(6H, s), 3.47(1H, d, J=17.0Hz), 3.63(1H, d, J=17.0Hz), 3.70(2H, s), 4.00(2H, d, J=7.3Hz), 5.06(1H, d, J=5.0Hz), 5.64(1H, dd, J=5.0Hz, 8.4Hz), 5.65~5.75(1H, m), 5.79(2H, brd, J=55.0Hz), 7.14(1H, d, J=15.4Hz), 8.22(2H, s), 9.70(1H, d, J=8.4Hz) |
| 70 | 1760, 1670, 1595, 1525 | (DMSO-d$_6$) 3.12(6H, s), 3.91(6H, s), 3.49(1H, d, J=17.2Hz), 3.67(1H, d, J=17.2Hz), 4.35(2H, m), 5.08(1H, d, J=5.1Hz), 5.66(1H, dd, J=5.1Hz, 8.4Hz), 5.7~6.0(1H, m), 5.79(2H, d, J=55.5Hz), 7.09(1H, d, J=15.8Hz), 8.21(2H, s), 9.71(1H, d, J=8.4Hz) |
| 71 | 1750, 1660, 1590 | (D$_2$O) 3.16(6H, s), 3.62(2H, s), 3.68(3H, s), 3.81(2H, s), 4.15(2H, m), 5.19(1H, d, J=5.5Hz), 5.76(2H, d, J=60.0Hz), 5.78(1H, d, J=5.5Hz), 5.90(1H, m), 6.84(1H, d, J=17.0Hz) |
| 72 | 1750, 1660, 1580 | (DMSO-d$_6$) 3.15(3H, s), 3.21(3H, s), 3.47(1H, d, J=17.2Hz), 3.68(1H, d, J=17.2Hz), 3.77(1H, d, J=14.3Hz), 3.93(1H, d, J=14.3Hz), 4.12(2H, m), 5.08(1H, d, J=4.8Hz), 5.68(1H, dd, J=4.8Hz, 8.1Hz), 5.75(1H, m), 5.79(2H, d, J=55.3Hz), 7.03(1H, d, J=15.8Hz), 8.21(2H, s), 9.72(1H, d, J=8.4Hz), 11.4(1H, brs) |
| 73 | 1750, 1650, 1580 | (DMSO-d$_6$) 3.14(3H, s), 3.15(3H, s), 3.48(1H, d, J=16.9Hz), 3.66(1H, d, J=16.9Hz), 3.71(2H, d, J=5.9Hz), 4.08(2H, m), 4.15(2H, m), 5.07(1H, d, J=5.1Hz), 5.67(1H, dd, J=5.1Hz, 8.1Hz), 5.70(1H, m), 5.78(2H, d, J=53.8Hz), 7.07(1H, s), 7.15(1H, d, J=15.8Hz), 7.54(1H, s), 8.21(2H, s), 9.15(1H, brs), 9.71(1H, d, J=8.1Hz) |
| 74 | 1760, 1650, 1620, 1590, 1520 | (DMSO-d$_6$) 3.10(3H, s), 3.1~3.7(8H, m), 3.22(3H, s), 3.41(1H, d, J=17.2Hz), 3.67(1H, d, J=17.2Hz), 4.06(2H, m), 4.35(2H, d, J=6.2Hz), 5.05(1H, d, J=5.1Hz), 5.6~5.9(1H, m), 5.66(1H, dd, J=5.1Hz, 8.4Hz), 5.78(2H, d, J=55.3Hz), 6.92(1H, d, J=15.8Hz), 8.20(2H, s), 9.78(1H, d, J=8.4Hz) |
| 75 | 1750, 1650, 1580, 1520 | (DMSO-d$_6$) 3.13(3H, s), 3.13~3.50(4H, m), 3.16(3H, s), 3.48(1H, d, J=16.9Hz), 3.64(1H, d, J=16.9Hz), 4.00(2H, s), 4.13(2H, d, J=7.3Hz), 5.06(1H, d, J=5.1Hz), 5.6~5.9(1H, m), 5.66(1H, dd, J=5.1Hz, 8.1Hz), 5.78(2H, d, J=55.3Hz), 7.10(1H, d, J=15.4Hz), 8.22(2H, s), 8.96(1H, d, J=5.1Hz), 9.71(1H, d, J=8.1Hz) |
| 76 | 1750, 1650, 1590, 1510 | (DMSO-d$_6$) 3.06(6H, s), 3.14~3.48(2H, m), 3.19(3H, s), 3.22(3H, s), 3.66~3.75(4H, m), 4.09(2H, m), 4.11~4.30(2H, m), 5.07(1H, d, J=4.8Hz), 5.67(1H, dd, J=4.8Hz, 8.1Hz), 5.71~5.77(1H, m), 5.79(2H, d, J=55.0Hz), 7.19(1H, d, J=15.4Hz), 8.23(2H, s), 9.73(1H, d, J=8.1Hz) |

-continued

List of physical data

| | Infrared absorption spectrum (cm$^{-1}$, Nujol) | NMR Spectrum (δ) |
|---|---|---|
| 77 | 1750, 1660, 1580 | (DMSO-d$_6$) 1.98(2H, brs), 2.67(6H, s), 2.72(2H, brs), 3.00(3H, s), 3.11(3H, s), 3.20(2H, m), 3.54(1H, d, J=17.6Hz), 3.82(1H, d, J=17.6Hz), 4.03(2H, m), 5.15(1H, d, J=4.8Hz), 5.78(1H, dd, J=4.8Hz, 8.1Hz), 5.79(2H, d, J=54.9Hz), 5.91(1H, m), 7.09(1H, d, J=15.4Hz), 8.22(2H, s), 9.72(1H, d, J=8.1Hz) |
| 78 | 1750, 1660, 1580 | (DMSO-d$_6$) 2.48(6H, s), 2.60(2H, m), 3.07(3H, s), 3.08(3H, s), 3.24(2H, m), 3.54 and 3.59(total 1H, d, J=17.6Hz), 3.82 and 3.88(total 1H, d, J=17.6Hz), 4.15(2H, m), 4.38(1H, m), 5.17 and 5.18(total 1H, d, J=4.8Hz), 5.79(1H, m), 5.79(2H, d, J=57.1Hz), 6.00(1H, m), 7.03 and 7.07(total 1H, d, J=15.8Hz), 8.22(2H, s), 9.74 and 9.77(total 1H, d, J=8.4Hz) |
| 79 | 1750, 1650, 1580, 1510 | (DMSO-d$_6$) 3.50(1H, d, J=16.9Hz), 3.68(1H, d, J=16.9Hz), 4.45~5.11(14H, m), 5.07(1H, d, J=5.1Hz), 5.63~5.71(1H, m), 5.65(1H, dd, J=5.1Hz, 8.1Hz), 5.78(2H, d, J=58.3Hz), 7.17(1H, d, J=15.8Hz), 8.27(2H, s), 9.72(1H, d, J=8.1Hz) |
| 80 | — | (D$_2$O) 3.69~3.74(2H, m), 5.13(2H, d, J=4.8Hz), 5.37(1H, d, J=4.8Hz), 5.96(1H, d, J=4.8Hz), 5.96(2H, d, J=54.2Hz), 6.18(1H, m), 6.92(1H, d, J=15.8Hz), 7.54~7.56(1H, m), 7.63~7.66(1H, m), 7.87~7.89(2H, m) |
| 81 | 1750, 1650, 1580, 1510 | (DMSO-d$_6$) 2.41(3H, s), 3.02(2H, t, J=5.5Hz), 3.42(1H, d, J=17Hz), 3.52(1H, d, J=17Hz), 3.62~3.66(2H, m), 5.03(1H, d, J=4.8Hz), 5.21(2H, d, J=5.1Hz), 5.63(1H, dd, J=4.8Hz, 8.4Hz), 5.71~5.84(1H, m), 6.67(1H, d, J=16.1Hz), 8.24(2H, s), 9.68(1H, d, J=8.4Hz), 10.1(1H, s) |
| 82 | — | (DMSO-d$_6$) 3.39(1H, d, J=16.9Hz), 3.49(1H, d, J=16.9Hz), 4.2~4.35(2H, m), 5.04(1H, d, J=5.0Hz), 5.15~5.40(2H, m), 5.65(1H, dd, J=5.0Hz, 8.2Hz), 5.75~5.90(1H, m), 5.77(2H, d, J=56.4Hz), 7.11(1H, d, J=15.8Hz), 7.45(1H, s), 8.0~8.15(2H, m), 8.22(2H, s), 8.30(1H, s), 8.54(1H, m), 9.03(1H, d, J=5.5Hz), 9.68(1H, d, J=8.2Hz) |
| 83 | 1760, 1670, 1620, 1520 | (DMSO-d$_6$) 3.2~3.7(10H, m), 5.01(1H, d, J=4.8Hz), 5.37(2H, d, J=4.5Hz), 5.62(1H, dd, J=4.8Hz, 8.2Hz), 5.78(2H, d, J=56.4Hz), 5.98(1H, dt, J=4.5Hz, 16.5Hz), 6.29(1H, d, J=16.5Hz), 8.17(2H, d, J=7.0Hz), 8.21(2H, s), 9.06(2H, d, J=7.0Hz), 9.69(1H, d, J=8.2Hz) |
| 84 | 1765, 1660, 1600, 1520 | (DMSO-d$_6$) 3.30~3.60(8H, m), 5.04(1H, d, J=4.8Hz), 5.35(2H, d, J=6.6Hz), 5.64(1H, dd, J=4.8Hz, 8.4Hz), 5.78(2H, d, J=56.0Hz), 5.80~5.95(1H, m), 7.20(1H, d, J=15.8Hz), 8.23(2H, s), 8.46(2H, d, J=6.6Hz), 9.18(2H, d, J=6.6Hz), 9.56(1H, t, J=5.0Hz), 9.71(1H, d, J=8.4Hz) |
| 85 | 1760, 1665, 1590, 1520 | (DMSO-d$_6$) 3.41(1H, d, J=17.0Hz), 3.48(1H, d, J=17.0Hz), 3.74(2H, s), 5.04(1H, d, J=5.0Hz), 5.30(2H, d, J=7.3Hz), 5.63(1H, dd, J=5.0Hz, 8.4Hz), 5.77(2H, d, J=54.2Hz), 5.80~5.90(1H, m), 7.19(1H, s), 7.24(1H, d, J=15.8Hz), 7.82(1H, s), 8.09(1H, dd, J=6.2Hz, 8.0Hz), 8.23(2H, s), 8.46(1H, d, J=8.0Hz), 8.93(1H, d, J=6.2Hz), 8.98(1H, s), 9.71(1H, d, J=8.4Hz) |
| 86 | 1765, 1670, 1595, 1525 | (DMSO-d$_6$) 3.42(1H, d, J=16.9Hz), 3.56(1H, d, J=16.9Hz), 4.19(2H, m), 4.41(2H, m), 4.98(2H, s), 5.04(1H, d, J=4.8Hz), 5.18(2H, d, J=6.6Hz), 5.63(1H, dd, J=4.8Hz, 8.4Hz), 5.77(1H, m), 5.78(2H, d, J=52.0Hz), 6.77(1H, d, J=2.9Hz), 7.06(1H, d, J=15.8Hz), 8.21(2H, s), 8.48(1H, d, J=2.9Hz), 9.69(1H, d, J=8.4Hz) |
| 87 | — | (D$_2$O) 2.93(3H, s), 3.26(6H, s), 3.6~3.9(6H, m), 4.22(2H, d, J=7.3Hz), 5.40(1H, d, J=4.8Hz), 5.97(2H, d, J=54.2Hz), 5.98(1H, d, J=4.8Hz), 6.00~6.15(1H, m), 7.07(1H, d, J=15.4Hz) |
| 88 | 1750, 1650, 1590, 1525 | (DMSO-d$_6$) 3.02, 3.04, 3.06 and 3.08(total 6H, s), 3.20~3.50(6H, m), 3.61 and 3.70(total 1H, d, J=16.9Hz), 4.06~4.13(3H, m), 5.05~5.75(1H, m), 5.06 and 5.07(total 1H, d, J=4.8Hz), 5.65(1H, dd, J=4.8Hz, 8.1Hz), 5.78(2H, d, J=55.3Hz), 7.09 and 7.14(total 1H, d, J=15.8Hz), 8.21(2H, s), 9.71 and 9.74(total 1H, d, J=8.4Hz) |
| 89-1 | 1755, 1650, 1590, 1525 | (DMSO-d$_6$) 1.75(1H, m), 2.51(1H, m), 3.04(3H, s), 3.2~3.9(7H), 4.03(1H, m), 4.19(1H, m), 4.46(1H, s), 5.05(1H, d, J=4.8Hz), 5.6~5.8(1H, m), 5.63(1H, dd, J=4.8Hz, 8.1Hz), 5.78(2H, d, J=58.6Hz), 7.15(1H, d, J=15.8Hz), 8.21(2H, s), 9.69(1H, d, J=8.1Hz) |
| 89-2 | 1755, 1650, 1590, 1525 | (DMSO-d$_6$) 1.80(1H, m), 2.60(1H, m), 3.03(3H, s), 3.48(1H, d, J=16.9Hz), 3.62(1H, d, J=16.9Hz), 3.65~4.00(6H, m), 4.16(1H, m), 4.46(1H, s), 5.07(1H, d, J=5.1Hz), 5.6~5.8(1H, m), 5.65(1H, dd, J=5.1Hz, 8.1Hz), 5.78(2H, d, J=57.5Hz), 7.17(1H, d, J=15.8Hz), 8.22(2H, s), 9.70(1H, d, J=8.1Hz) |
| 90 | 1760, 1650, 1590, 1530 | (DMSO-d$_6$) 1.71(2H, brs), 1.97(2H, brs), 2.94 and 2.96(total 3H, s), 3.1~3.5(6H, m), 3.61 and 3.62(total 1H, d, J=17.2Hz), 3.77(1H, brs), 4.02(2H, m), 5.04 and 5.05(total 1H, d, J=17.2Hz), 5.6~5.8(1H, m), 5.63(1H, dd, J=5.1Hz, 8.4Hz), 5.79(1H, d, J=58.6Hz), 7.19 and 7.20(total 1H, d, J=15.4Hz), 8.24(2H, s), 9.69(1H, d, J=8.4Hz) |
| 91 | 1760, 1650, 1590, 1530 | (DMSO-d$_6$) 1.72(2H, brs), 1.99(2H, brs), 3.2~3.8(8H, m), 3.84(3H, m), 4.10(2H, m), 5.05 and 5.06(total 1H, d, J=4.8Hz), 5.6~5.8(1H, m), 5.64(1H, dd, J=4.8Hz, 8.1Hz), 5.78(2H, d, J=55.1Hz), 7.18(1H, d, J=14.3Hz), 8.21(2H, s), 9.69(1H, d, J=8.1Hz) |
| 92 | 1760, 1665, 1590, 1520 | (DMSO-d$_6$) 3.15(3H, s), 3.20(3H, s), 3.47(1H, d, J=16.9Hz), 3.66(1H, d, J=16.9Hz), 4.05~4.25(4H, m), 4.45~4.55(1H, m), 4.60~4.70(1H, m), 5.06(1H, d, J=4.8Hz), 5.66(1H, dd, J=4.8Hz, 8.1Hz), 5.7~5.8(1H, m), 5.78(2H, d, J=54.0Hz), 7.09(1H, d, J=15.4Hz), 8.22(2H, s), |

|     | Infrared absorption spectrum (cm$^{-1}$, Nujol) | NMR Spectrum ($\delta$) |
|-----|---|---|
|     |   | 9.20(1H, brs), 9.71(1H, d, J=8.1Hz) |
| 93  | 1760, 1660, 1595 | (DMSO-d$_6$) 2.61(2H, m), 2.96(3H, s), 2.97(3H, s), 3.3~3.6(2H, m), 3.45(1H, d, J=16.9Hz), 3.68(1H, d, J=16.9Hz), 3.96(2H, d, J=7.3Hz), 5.07(1H, d, J=4.8Hz), 5.6~5.8(1H, m), 5.65(1H, dd, J=4.8Hz, 8.1Hz), 5.78(2H, d, J=58.3Hz), 7.08(1H, s), 7.18(1H, d, J=15.8Hz), 7.82(1H, s), 8.21(2H, s), 9.70(1H, d, J=8.1Hz) |
| 94  | 1760, 1660, 1590, 1520 | (DMSO-d$_6$) 2.08(2H, s), 2.98(3H, s), 3.2~3.8(10H, m), 4.09(2H, m), 5.07(1H, d, J=4.8Hz), 5.6~5.9(1H, m), 5.65(1H, dd, J=4.8Hz, 8.1Hz), 5.79(2H, d, J=55.3Hz), 6.05(2H, s), 7.19(1H, d, J=15.8Hz), 8.21(2H, s), 9.70(1H, d, J=8.1Hz) |
| 95  | 1760, 1660, 1595, 1520 | (DMSO-d$_6$) 3.02(3H, s), 3.04(3H, s), 3.45(1H, d, J=17.2Hz), 3.67(1H, d, J=17.2Hz), 3.7~4.0(4H, m), 4.15(2H, m), 5.07(1H, d, J=5.1Hz), 5.65~5.80(1H, m), 5.66(1H, dd, J=5.1Hz, 8.1Hz), 5.79(2H, d, J=55.0Hz), 7.15(1H, d, J=15.8Hz), 8.21(2H, s), 9.70(1H, d, J=8.4Hz) |
| 96  | 1760, 1665, 1595, 1520 | (DMSO-d$_6$) 1.24(6H, t, J=7.0Hz), 3.2~3.6(6H, m), 3.68(1H, d, J=17.2Hz), 3.90(2H, s), 4.09(2H, m), 5.07(1H, d, J=4.8Hz), 5.6~5.8(2H, m), 5.79(2H, d, J=58.6Hz), 7.16(1H, d, J=16.0Hz), 7.69(1H, s), 8.08(1H, s), 8.21(2H, s), 9.70(2H, d, J=8.1Hz) |
| 97  | 1760, 1660, 1600 | (DMSO-d$_6$) 2.5~2.7(2H, m), 2.57(3H, d, J=4.4Hz), 2.97(3H, s), 2.98(3H, s), 3.2~3.6(2H, m), 3.45(1H, d, J=16.5Hz), 3.71(1H, d, J=16.5Hz), 3.97(2H, s), 5.08(1H, d, J=5.1Hz), 5.65~5.80(2H, m), 5.78(2H, d, J=55.0Hz), 7.19(1H, d, J=15.4Hz), 8.21(2H, s), 8.42(1H, brs), 9.72(1H, d, J=8.4Hz) |
| 98  | 1760, 1660, 1600 | (DMSO-d$_6$) 2.84(3H, s), 2.87(2H, m), 2.97(6H, s), 3.02(3H, s), 3.46(2H, m), 3.46(1H, d, J=17.2Hz), 3.65(1H, d, J=17.2Hz), 3.99(2H, d, J=7.3Hz), 5.07(1H, d, J=4.8Hz), 5.6~5.8(1H, m), 5.64(1H, dd, J=4.8Hz, 8.4Hz), 5.78(2H, d, J=58.6Hz), 7.19(1H, d, J=15.4Hz), 8.21(2H, s), 9.70(1H, d, J=8.4Hz) |
| 99  | 1760, 1660, 1595, 1525 | (DMSO-d$_6$) 2.99(6H, s), 3.32(3H, s), 3.47(2H, brs), 3.48(1H, d, J=17.2Hz), 3.65(1H, d, J=17.2Hz), 3.76(2H, brs), 4.02(2H, d, J=7.0Hz), 5.07(1H, d, J=5.1Hz), 5.6~5.7(1H, m), 5.65(1H, dd, J=5.1Hz, 8.4Hz), 5.79(2H, d, J=55.7Hz), 7.17(1H, d, J=15.4Hz), 8.21(2H, s), 9.71(1H, d, J=8.4Hz) |
| 100 | 1760, 1670, 1590, 1520 | (DMSO-d$_6$) 1.20(3H, d, J=6.2Hz), 3.06(3H, s), 3.22(3H, s), 3.48(1H, d, J=17.0Hz), 3.61(1H, d, J=17.0Hz), 3.95(1H, d, J=9.2Hz), 4.15~4.45(3H, m), 5.07(1H, d, J=4.8Hz), 5.66(1H, dd, J=4.8Hz, 8.4Hz), 5.79(2H, d, J=55.0Hz), 5.8~5.9(1H, m), 7.01(1H, d, J=15.4Hz), 7.83(1H, s), 8.21(2H, s), 8.71(1H, s), 9.71(1H, d, J=8.4Hz) |
| 101 | 1760, 1650, 1630, 1590 | (DMSO-d$_6$) 2.10(2H, s), 3.30~3.90(14H, m), 4.10~4.25(2H, m), 5.06(1H, d, J=5.1Hz), 5.6~5.8(1H, m), 5.65(1H, dd, J=5.1Hz, 8.1Hz), 5.78(2H, d, J=58.6Hz), 6.04(2H, s), 7.17(1H, d, J=15.8Hz), 8.22(2H, s), 9.70(1H, d, J=8.1Hz) |
| 102 | 1760, 1660, 1590 | (D$_2$O) 3.12(6H, s), 3.78(1H, d, J=15.5Hz), 3.85(1H, d, J=15.5Hz), 4.11(2H, d, J=7.6Hz), 4.60(2H, s), 5.40(1H, d, J=4.8Hz), 5.97(2H, d, J=54.6Hz), 5.98(1H, d, J=4.8Hz), 6.11(1H, dt, J=7.6Hz, 15.4Hz), 6.66(1H, d, J=2.8Hz), 7.04(1H, d, J=15.4Hz), 7.93(1H, d, J=2.8Hz) |
| 103 | 1750, 1660, 1620, 1590 | (DMSO-d$_6$) 3.4~3.6(2H, m), 5.03(1H, d, J=5.1Hz), 5.10(1H, d, J=7.0Hz), 5.64(1H, dd, J=5.1Hz, 8.0Hz), 5.77(2H, d, J=55.32Hz), 5.70~5.9(1H, m), 6.73(2H, s), 7.21(1H, d, J=15.7Hz), 7.57(1H, d, J=1.8Hz), 7.6~7.7(1H, m), 8.05~8.15(2H, m) |
| 104 | — | (D$_2$O) 3.30(3H, s), 3.31(3H, s), 3.77(1H, d, J=17.0Hz), 3.84(1H, d, J=17.0Hz), 3.94(2H, s), 4.34(2H, d, J=8.0Hz), 5.40(1H, d, J=4.8Hz), 6.01(2H, d, J=54.2Hz), 5.98(1H, d, J=4.8Hz), 6.0~6.1(1H, m), 7.03(1H, d, J=15.7Hz) |
| 105 | 1760, 1660, 1590 | (D$_2$O) 3.19(3H, s), 3.30(3H, s), 3.32(3H, s), 3.80(1H, d, J=17.2Hz), 3.86(1H, d, J=17.2Hz), 3.98(2H, s), 4.3~4.4(2H, m), 5.39(1H, d, J=5.1Hz), 5.97(2H, d, J=54.2Hz), 5.98(1H, d, J=5.1Hz), 6.0~6.1(1H, m), 7.04(1H, d, J=15.4Hz) |
| 106 | 1760, 1650, 1590 | (D$_2$O) 3.06(6H, s), 3.75(1H, d, J=17.2Hz), 3.83(1H, d, J=17.2Hz), 4.05(2H, d, J=7.3Hz), 4.47(2H, s), 5.38(1H, d, J=4.8Hz), 5.95(2H, d, J=62.2Hz), 5.95(1H, d, J=4.8Hz), 6.07(1H, dt, J=7.3Hz, 15.8Hz), 7.02(1H, d, J=15.8Hz), 7.55(1H, s), 7.92(1H, s) |
| 107 | — | (D$_2$O) 3.7~3.9(6H, m), 4.15~4.25(4H, m), 4.43(2H, d, J=7.3Hz), 5.38(1H, d, J=4.7Hz), 5.95(1H, d, J=54.2Hz), 5.97(1H, d, J=4.7Hz), 6.0~6.1(1H, m), 7.06(1H, d, J=15.7Hz) |
| 108 | 1765, 1670, 1630, 1525 | (DMSO-d$_6$) 3.27(2H, brs), 3.42(1H, d, J=17.0Hz), 3.48(1H, d, J=17.0Hz), 3.56(2H, brs), 3.65(2H, brs), 3.69(2H, brs), 5.04(1H, d, J=4.8Hz), 5.33(2H, d, J=7.0Hz), 5.63(1H, dd, J=8.4Hz, 4.8Hz), 5.78(2H, d, J=55.3Hz), 5.85~5.95(1H, m), 7.21(1H, d, J=15.8Hz), 8.20(2H, d, J=6.6 Hz), 8.22(2H, s), 9.14(2H, d, J=6.6Hz), 9.70(1H, d, J=8.4Hz) |
| 109 | 1760, 1660, 1610, 1575, 1520 | (D$_2$O) 3.75(2H, s), 4.20(2H, s), 5.01(2H, s), 5.35~5.45(3H, m), 5.96(2H, d, J=54.6Hz), 5.97(1H, d, J=4.8Hz), 6.20(1H, dt, J=15.8Hz, 7.5Hz), 7.03(1H, d, J=15.8Hz), 8.14(2H, d, J=6.2Hz), 8.88(2H, d, J=6.2Hz) |
| 110 | 1760, 1660, 1615, 1590 | (DMSO-d$_6$) 3.44(1H, d, J=16.9Hz), 3.53(1H, d, J=16.9Hz), 3.89(2H, s), 5.07(1H, d, J=4.8Hz), 5.12(2H, brd, J=6.0Hz), 5.68(1H, dd, J=4.8Hz, 8.4Hz), 5.78(2H, d, J=55.7Hz), 5.92(1H, dt, J=15.8Hz, 6.0Hz), 7.03(1H, d, J=15.8Hz), 7.35(1H, brs), 7.85(2H, d, J=7.0Hz), 8.22(2H, s), 8.60(2H, d, J=7.0Hz), 9.73(1H, d, J=8.4Hz) |
| 111 | — | (DMSO-d$_6$-D$_2$O) 2.66(2H, t, J=7.0Hz), 3.08(2H, t, J=7.0Hz), |

-continued

List of physical data

| | Infrared absorption spectrum (cm$^{-1}$, Nujol) | NMR Spectrum ($\delta$) |
|---|---|---|
| | | 3.40(1H, d, J=17.0Hz), 3.48(1H, d, J=17.0Hz), 5.00(1H, d, J=5.0Hz), 5.18(2H, d, J=7.0Hz), 5.63(1H, d, J=5.0Hz), 5.75(2H, d, J=55.7Hz), 5.88(1H, dd, J=7.0Hz, 16.0Hz), 7.10(1H, d, J=16.0Hz), 7.59(2H, d, J=6.6Hz), 8.81(2H, d, J=6.6Hz) |
| 112 | 1760, 1655, 1610, 1520 | (DMSO-d$_6$) 2.01(4H, brs), 3.1~3.9(8H, m), 4.25~4.4(2H, m), 5.10(1H, d, J=4.8Hz), 5.7~5.9(2H, m), 5.79(2H, d, J=55.0Hz), 7.04(1H, d, J=15.7Hz), 7.39(1H, brs), 8.22(2H, s), 9.74(1H, d, J=8.5Hz) |
| 113 | 1760, 1655, 1575 | (DMSO-d$_6$) 3.41(1H, d, J=16.9Hz), 3.48(1H, d, J=16.9Hz), 3.59(2H, s), 5.04(1H, d, J=5.1Hz), 5.28(2H, brs), 5.63(1H, brs), 5.78(2H, d, J=55.7Hz), 5.8~5.95(1H, m), 7.17(1H, d, J=16.0Hz), 8.02(1H, dd, J=6.2Hz, 7.7Hz), 8.22(2H, s), 8.42(1H, d, J=7.7Hz), 8.83(1H, d, J=6.2Hz), 8.96(1H, s), 9.72(1H, brs) |
| 114 | 1770, 1690, 1630, 1600 | (DMSO-d$_6$) 3.14(3H, s), 3.15(3H, s), 3.48(1H, d, J=16.8Hz), 3.66(1H, d, J=16.8Hz), 4.03(1H, d, J=15.5Hz), 4.06(1H, d, J=15.5Hz), 4.17(2H, brd, J=7.7Hz), 5.07(1H, d, J=4.8Hz), 5.65(1H, dd, J=4.8Hz, 8.0Hz), 5.70(1H, dt, J=7.7Hz, 15.4Hz), 7.17(1H, d, J=15.4Hz), 7.22(1H, t, J=70.5Hz), 7.64(1H, s), 8.29(3H, s), 9.83(1H, d, J=8.0Hz) |
| 115 | — | (D$_2$O) 3.75(2H, s), 5.39(1H, d, J=4.7Hz), 5.44(2H, d, J=8.0Hz), 5.97(1H, d, J=4.7Hz), 6.21(1H, dt, J=8.0Hz, 15.0Hz), 7.07(1H, d, J=15.0Hz), 7.09(1H, t, J=70.0Hz), 8.37(2H, d, J=6.7Hz), 9.01(2H, d, J=6.7Hz) |
| 116 | 1770, 1675, 1630, 1605 | (DMSO-d$_6$) 2.95~3.05(6H, m), 3.20~3.30(6H, m), 3.46(1H, d, J=17.0Hz), 3.62(1H, d, J=17.0Hz), 3.92(2H, d, J=7.3Hz), 5.07(1H, d, J=5.1Hz), 5.50~5.70(2H, m), 7.17(1H, d, J=15.8Hz), 7.22(1H, t, J=70.7Hz), 8.30(2H, s), 9.83(1H, d, J=7.9Hz) |
| 117 | 1770, 1675, 1605 | (DMSO-d$_6$) 3.40~3.50(7H, m), 3.70(1H, d, J=18.2Hz), 3.85(6H, brs), 4.10~4.25(2H, m), 5.08(1H, d, J=5.0Hz), 5.66(1H, dd, J=5.0Hz, 8.4Hz), 5.75(1H, dt, J=7.8Hz, 15.8Hz), 7.19(1H, d, J=15.8Hz), 7.22(1H, t, J=70.7Hz), 8.27(2H, s), 9.83(1H, d, J=8.4Hz) |

EXPERIMENT 7

Synthesis of Raw Material Compound p-methoxybenzyl 7$\beta$-[2-(5-tritylamino-1,2,4-thiadiazol-3-yl)-(Z)-2-(2,2,2-trifluoroethyl)oxyiminoacetamido]-3-[(Z)-3-chloro-1-propen-1-yl]3-cephem-4-carboxylate:

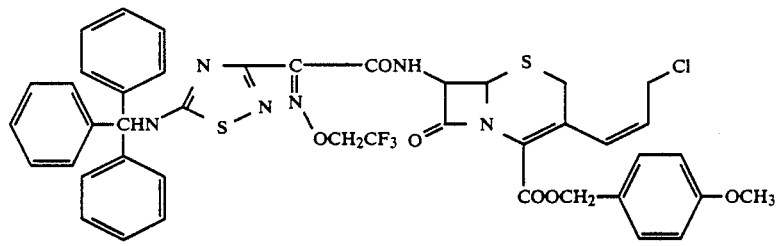

A mixture solution comprising dimethylformamide (0.247 ml) and tetrahydrofuran (3 ml) was cooled to −10° C., and phosphorus oxychloride (0.297 ml) was added thereto and stirred for 40 minutes with ice-cooling. To the resulting solution was added the tetrahydrofuran solution (4 ml) of 2-(5-tritylamino-1,2,4-thiadiazol-3-yl)-(Z)-2-(2,2,2-trifluoroethyl)oxyiminoacetic acid (1.36 g), followed by stirring for further one hour at the said temperature. The resulting reaction solution was added to a mixture solution comprising p-methoxybenzyl 7$\beta$-amino-3-[(Z)-3-chloro-1-propen-1-yl]-3-cephem-4-carboxylate hydrochloride (1.145 g), N-(trimethylsilyl)acetamide (2.09 g) and ethyl acetate (10 ml), with cooling at −20° C., followed by elevating the temperature up to 0° C. with stirring for one hour. After ethyl acetate was added to the reaction solution, this was washed with water and dried with anhydrous sodium sulfate. The solvent was evaporated out and the residue was purified by silicagel column chromatography to obtain the desired product (1.43 g).

EXAMPLE 118

7$\beta$-[2-(5-Amino-1,2,4-thiadiazol-3-yl)-(Z)-2-fluoromethoxyiminoacetamido]-3-[(E)-3-(carbamoylmethyldimethylammonio)-1-propen-1-yl]-3-cephem-4-carboxylate:

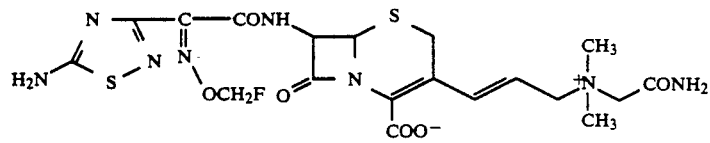

The compound (500 mg) obtained in Experiment 4 was dissolved in a mixture solution comprising methanol (3 ml) and dimethylformamide (1 ml), and N,N-dimethylglycinamide (71.3 mg) was added thereto with ice-cooling and then stirred overnight at room temperature. The resulting reaction solution was added to a mixture solution comprising ethyl acetate (50 ml) and ethyl ether (50 ml) and the precipitate formed was collected by filtration and dried to obtain an yellow powder (382 mg).

This powder was added to a mixture solution comprising trifluoroacetic acid (2.7 ml) and anisole (2.3 ml), followed by stirring for 2 hours with ice-cooling. The reaction solution was added to a mixture solution comprising ethyl ether (25 ml) and isopropyl ether (25 ml), and the precipitate formed was collected by filtration and washed with ethyl ether. The thus-obtained precipitate was suspended in water (4.5 ml), followed by adjusting the pH of the resulting suspension to the range of from 5.5 to 6.5 with sodium acetate, and the insoluble substances were removed by filtration. The filtrate was purified by reversed phase-silicagel column chromatography to obtain the desired product (94 mg).

EXAMPLE 119

7β-[2-(5-Amino-1,2,4-thiadiazol-3-yl)-(Z)-2-fluoromethoxyiminoacetamido]-3-[(E)-3-(1-methyl-4-sulfamoyl-1-piperazinio)-1-propen-1-yl]-3-cephem-4-carboxylate

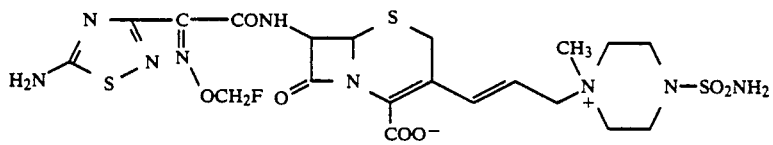

The compound (500 mg) obtained in Experiment 4 was dissolved in a mixture solution comprising methanol (3 ml) and dimethylformamide (1 ml), and N-sulfamoyl-N'-methylpiperazine (116 mg) was added thereto with ice-cooling and then stirred overnight at room temperature. The reaction solution was added to a mixture solution comprising ethyl acetate (50 ml) and ethyl ether (50 ml), and the precipitate formed was collected by filtration and dried to obtain an yellow powder (402 mg).

The powder was added to a mixture solution comprising trifluoroacetic acid (2.8 ml) and anisole (2.5 ml) and stirred for 2 hours with ice-cooling. The reaction solution was added to a mixture solution comprising ethyl ether (25 ml) and isopropyl ether (25 ml), and the precipitate formed was collected by filtration and washed with ethyl ether. The resulting precipitate was suspended in water (4.5 ml), followed by adjusting the pH of the resulting suspension to the range of from 5.5 to 6.5 with sodium acetate, and the insoluble substances were removed by filtration. The filtrate was purified by reversed phase-silicagel column chromatography to obtain the desired product (58 mg).

EXAMPLE 120

7β-[2-(5-Amino-1,2,4-thiadiazol-3-yl)-(Z)-2-fluoromethoxyiminoacetamido]-3-[(E)-3-[(1,3,4-oxadiazol-2-yl)methyldimethylammonio]-1-propen-1-yl]-3-cephem-4-carboxylate

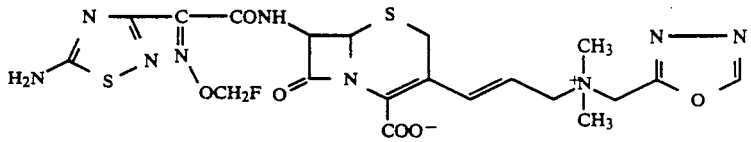

The compound (500 mg) obtained in Experiment 4 was dissolved in a mixture solution comprising methanol (1 ml) and ethyl acetate (4.8 ml), and the ethyl acetate solution (1 ml) of 2-dimethylaminomethyl-1,3,4-oxadiazole (88.8 mg) was added thereto with ice-cooling and then stirred overnight at room temperature. The resulting reaction solution was added to a mixture solution comprising ethyl acetate (50 ml) and ethyl ether (50 ml), and the precipitate formed was collected by filtration and dried to obtain an yellow powder (443 mg).

The powder was added to a mixture solution comprising trifluoroacetic acid (3.1 ml) and anisole (2.7 ml) and stirred for 2 hours with ice-cooling. The resulting reaction solution was added to a mixture solution comprising ethyl ether (25 ml) and isopropyl ether (25 ml), and the precipitate formed was collected by filtration and washed with ethyl ether. The thus-obtained precipitate was suspended in water (4.5 ml), followed by adjusting the pH of the resulting suspension to the range of from 5.5 to 6.5 with sodium acetate, and the insoluble substances were removed by filtration. The filtrate was purified by reversed phase-silicagel column chromatography to obtain the desired product (92 mg).

EXAMPLE 121

7β-[2-(5-Amino-1,2,4-thiadiazol-3-yl)-(Z)-2-fluoromethoxyiminoacetamido]-3-[(E)-3-(1-methyl-4-carbamoyl-1-piperazinio)-1-propen-1-yl]-3-cephem-4-carboxylate

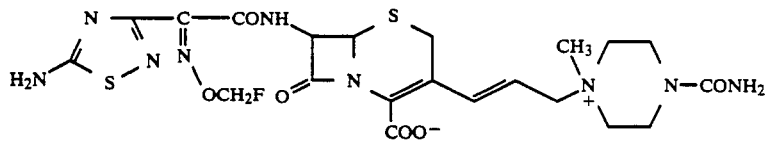

The compound (500 mg) obtained in Experiment 4 was dissolved in a mixture solution comprising methanol (3 ml) and dimethylformamide (1 ml), and N-methyl-N'-carbamoylpiperazine (100 mg) was added thereto with ice-cooling and then stirred overnight at room temperature. The reaction solution was added to a mixture solution comprising ethyl acetate (50 ml) and ethyl ether (30 ml), and the precipitate formed was collected by filtration and dried to obtain an yellow powder (425 mg).

The powder was added to a mixture solution comprising trifluoroacetic acid (3.0 ml) and anisole (2.6 ml) and stirred for 2 hours with ice-cooling. The reaction solution was added to a mixture solution comprising ethyl ether (25 ml) and isopropyl ether (25 ml), and the precipitate formed was collected by filtration and washed with ethyl ether. The precipitate was suspended in water (4.5 ml), followed by adjusting the pH of the resulting suspension to the range of from 5.5 to 6.5 with sodium acetate, and the insoluble substances were removed by filtration. The filtrate was purified by reversed phase-silicagel column chromatography to obtain the desired product (107 mg).

EXAMPLE 122

7β-[2-(5-Amino-1,2,4-thiadiazol-3-yl)-(Z)-2-fluoromethoxyiminoacetamido]-3-[(E)-3-(1,2-dimethyl-1-pyrazolidinio)-1-propen-1-yl]-3-cephem-4-carboxylate (Isomers: A and B)

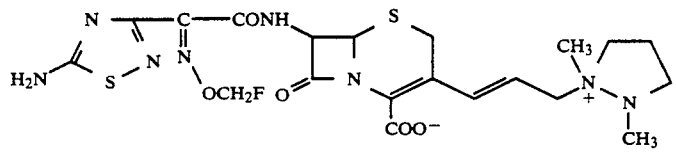

The compound (783 mg) obtained in Experiment 4 was dissolved in a mixture solution comprising methanol (1.5 ml) and ethyl acetate (7.1 ml), and the ethyl acetate solution (1.5 ml) of N,N'-dimethylpyrazolidine (103 mg) was added thereto with ice-cooling and then stirred overnight at room temperature. The reaction solution was added to a mixture solution comprising ethyl acetate (50 ml) and ethyl ether (50 ml), and the precipitate formed was collected by filtration and dried to obtain an yellow powder (631 mg).

The powder was added to a mixture solution comprising trifluoroacetic acid (4.5 ml) and anisole (3.8 ml) and stirred for 2 hours with ice-cooling. The reaction solution was added to a mixture solution comprising ethyl ether (25 ml) and isopropyl ether (25 ml), and the precipitate formed was collected by filtration and washed with ethyl ether. The precipitate was suspended in water (4.5 ml), followed by adjusting the pH of the resulting suspension to the range of from 5.5 to 6.5 with sodium acetate, and the insoluble substances were removed by filtration. The filtrate was purified by reversed phase-silicagel column chromatography to obtain the desired isomer A (37 mg) and isomer B (27 mg).

EXAMPLE 123

7β-[2-(5-Amino-1,2,4-thiadiazol-3-yl)-(Z)-2-fluoromethoxyiminoacetamido]-3-[(E)-3-(1-methyl-4-formimidoyl-1-piperazinio)-1-propen-1-yl]-3-cephem-4-carboxylate hydrochloride

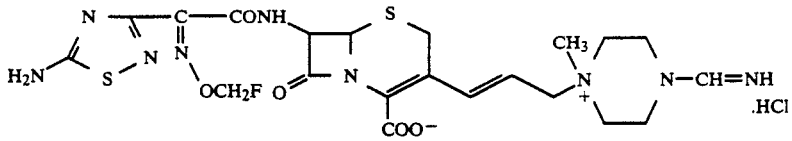

The compound (750 mg) obtained in Experiment 4 was dissolved in a mixture solution comprising methanol (4.5 ml) and dimethylformamide (1.5 ml), and N-methyl-N'-formimidoylpiperazine hydrochloride (158 mg) was added thereto with ice-cooling and then stirred overnight at room temperature. The reaction solution was added to a mixture solution comprising ethyl acetate (50 ml) and ethyl ether (30 ml), and the precipitate formed was collected by filtration and dried to obtain an yellow powder (485 mg).

The powder was added to a mixture solution comprising trifluoroacetic acid (3.4 ml) and anisole (3.0 ml) and stirred for 2 hours with ice-cooling. The reaction solution was added to a mixture solution comprising ethyl ether (25 ml) and isopropyl ether (25 ml), and the precipitate formed was collected by filtration and washed with ethyl ether. The precipitate was suspended in water (4.0 ml), and the insoluble substances were removed by filtration. The filtrate was purified by reversed phase-silicagel column chromatography to obtain the desired product (58 mg).

In the same manner as Examples 118 to 123, the compounds of the following Examples 124 to 140 were synthesized.

EXAMPLE 124

7β-[2-(5-Amino-1,2,4-thiadiazol-3-yl)-(Z)-2-fluoromethoxyiminoacetamido]-3-[(E)-3-(1-methyl-1-piperazinio)-1-propen-1-yl]-3-cephem-4-carboxylate

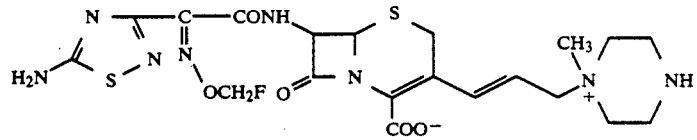

The compound (750 mg) obtained in Experiment 4 was reacted with N-methylpiperazine (116 μl), followed by removing the protective group, to obtain the desired product (16 mg).

EXAMPLE 125

7β-[2-(5-Amino-1,2,4-thiadiazol-3-yl)-(Z)-2-fluoromethoxyiminoacetamido]-3-[(E)-3-(4-carboxypyridinio)-1-propen-1-yl]-3-cephem-4-carboxylate

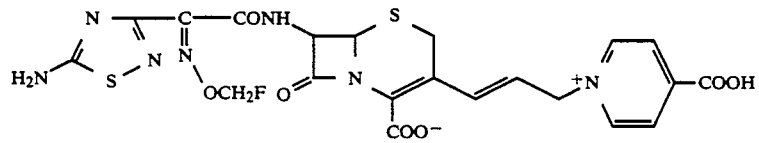

The compound (750 mg) obtained in Experiment 4 was reacted with isonicotinic acid (198 mg), followed by removing the protective group, to obtain the desired product (143 mg).

EXAMPLE 126

7β-[2-(5-Amino-1,2,4-thiadiazol-3-yl)-(Z)-2-fluoromethoxyiminoacetamido]-3-[(E)-3-(1-methylpyrrolidinio)-1-propen-1-yl]-3-cephem-4-carboxylate

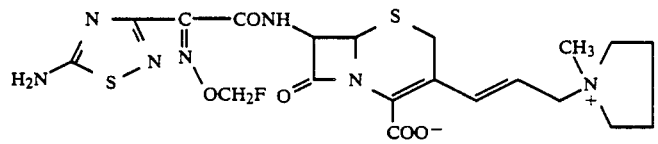

The compound (500 mg) obtained in Experiment 4 was reacted with N-methylpyrrolidine (55.8 μl), followed by removing the protective group, to obtain the desired product (21 mg).

EXAMPLE 127

7β-[2-(5-Amino-1,2,4-thiadiazol-3-yl)-(Z)-2-fluoromethoxyiminoacetamido]-3-[(E)-3-(4-carbamoylpyridinio)-1-propen-1-yl]-3-cephem-4-carboxylate

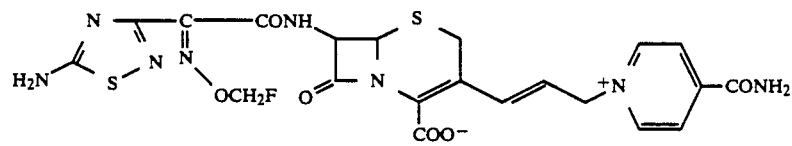

The compound (500 mg) obtained in Experiment 4 was reacted with 4-carbamoylpyridine (131 mg), followed by removing the protective group, to obtain the desired product (42 mg).

EXAMPLE 128

7β-[2-(5-Amino-1,2,4-thiadiazol-3-yl)-(Z)-2-fluoromethoxyiminoacetamido]-3-[(E)-3-(trimethylammonio)-1-propen-1-yl]-3-cephem-4-carboxylate

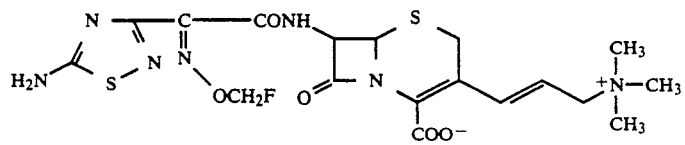

The compound (500 mg) obtained in Experiment 4 was reacted with trimethylamine (whereupon trimethylamine hydrochloride (57 mg), as neutralized, was used), followed by removing the protective group, to obtain the desired product (79 mg).

EXAMPLE 129

7β-[2-(5-Amino-1,2,4-thiadiazol-3-yl)-(Z)-2-fluoromethoxyiminoacetamido]-3-[(E)-3-(1,4-diazabicyclo[2,2,2]octan-1-io)-1-propen-1-yl]-3-cephem-4-carboxylate

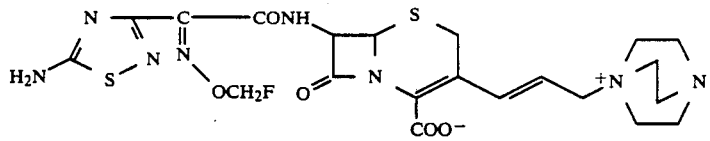

The compound (500 mg) obtained in Experiment 4 was reacted with 1,4-diazabicyclo[2,2,2]octane (72 mg), followed by removing the protective group, to obtain the desired product (61 mg).

EXAMPLE 130

7β-[2-(5-Amino-1,2,4-thiadiazol-3-yl)-(Z)-2-fluoromethoxyiminoacetamido]-3-[(E)-3-(1,5-diazabicyclo[3,3,0]octan-1-io)-1-propen-1-yl]-3-cephem-4-carboxylate

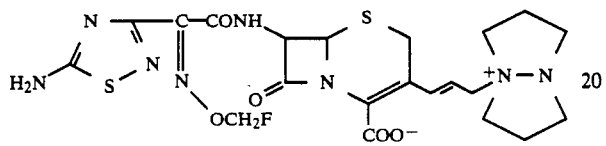

The compound (500 mg) obtained in Experiment 4 was reacted with 1,5-diazabicyclo[3,3,0]octane (120 mg), followed by removing the protective group, to obtain the desired product (32 mg).

EXAMPLE 131

7β-[2-(5-Amino-1,2,4-thiadiazol-3-yl)-(Z)-2-fluoromethoxyiminoacetamido]-3-[(E)-3-(4-methylthiomorpholine-1,1-dioxid-4-io)-1-propen-1-yl]-3-cephem-4-carboxylate

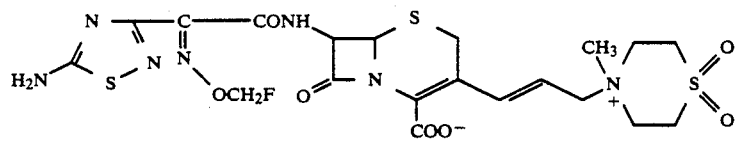

The compound (250 mg) obtained in Experiment 4 was reacted with 4-methylthiomorpholine-1,1-dioxide (52 mg), followed by removing the protective group, to obtain the desired product (17 mg).

EXAMPLE 132

7β-[2-(5-Amino-1,2,4-thiadiazol-3-yl)-(Z)-2-fluoromethoxyiminoacetamido]-3-[(E)-3-(1,4-dimethyl-1-piperazinio)-1-propen-1-yl]-3-cephem-4-carboxylate

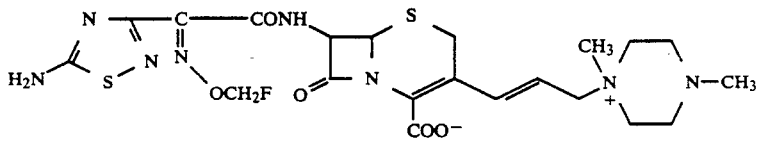

The compound (500 mg) obtained in Experiment 4 was reacted with 1,4-dimethylpiperazine (94 μl), followed by removing the protective group, to obtain the desired product (35 mg).

EXAMPLE 133

7β-[2-(5-Amino-1,2,4-thiadiazol-3-yl)-(Z)-2-fluoromethoxyiminoacetamido]-3-[(E)-3-[(2-aminoethyl)dimethylammonio]-1-propen-1-yl]-3-cephem-4-carboxylate

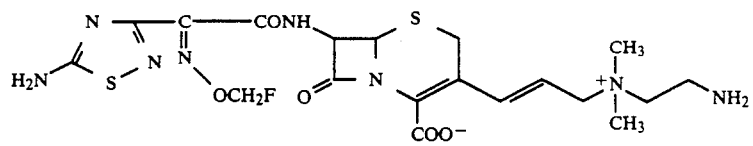

The compound (750 mg) obtained in Experiment 4 was reacted with N,N-dimethylethylenediamine (115 μl), followed by removing the protective group, to obtain the desired product (15 mg).

EXAMPLE 134

7β-[2-(5-Amino-1,2,4-thiadiazol-3-yl)-(Z)-2-fluoromethoxyiminoacetamido]-3-[(E)-3-[(tetrazol-5-yl)methyldimethylammonio]-1-propen-1-yl]-3-cephem-4-carboxylate

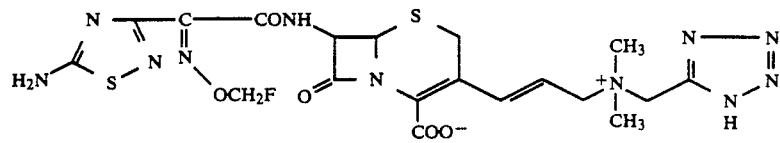

The compound (500 mg) obtained in Experiment 4 was reacted with 5-dimethylaminomethyltetrazole (150 mg), followed by removing the protective group, to obtain the desired product (37 mg).

EXAMPLE 135

7β-[2-(5-Amino-1,2,4-thiadiazol-3-yl)-(Z)-2-fluoromethoxyiminoacetamido]-3-[(E)-3-(3-sulfopyridinio)-1-propen-1-yl]-3-cephem-4-carboxylate

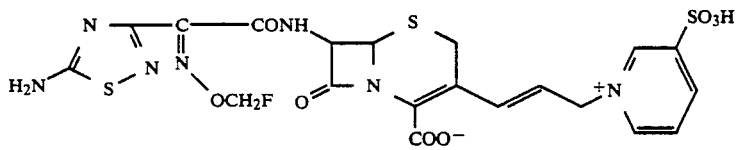

The compound (750 mg) obtained in Experiment 4 was reacted with 3-pyridinesulfonic acid (384 mg), followed by removing the protective group, to obtain the desired product (68 mg).

EXAMPLE 136

7β-[2-(5-Amino-1,2,4-thiadiazol-3-yl)-(Z)-2-fluoromethoxyiminoacetamido]-3-[(E)-3-[(2-dimethylaminoethyl)dimethylammonio]-1-propen-1-yl]-3-cephem-4-carboxylate

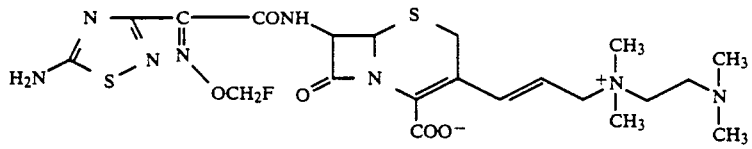

The compound (500 mg) obtained in Experiment 4 was reacted with N,N,N',N'-tetramethylethylenediamine (105 μl), followed by removing the protective group to obtain the desired product (22 mg).

EXAMPLE 137

7β-[2-(5-Amino-1,2,4-thiadiazol-3-yl)-(Z)-2-fluoromethoxyiminoacetamido]-3-[(E)-3-[(2-oxopropyl)dimethylammonio]-1-propen-1-yl]-3-cephem-4-carboxylate

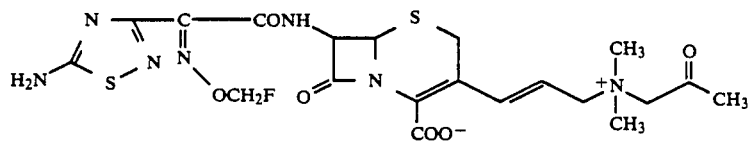

The compound (500 mg) obtained in Experiment 4 was reacted with (dimethylamino)acetone (80 μl), followed by removing the protective group, to obtain the desired product (60 mg).

EXAMPLE 138

7β-[2-(5-Amino-1,2,4-thiadiazol-3-yl)-(Z)-2-fluoromethoxyiminoacetamido]-3-[(E)-3-(4-carbamoylquinuclidinio)-1-propen-1-yl]-3-cephem-4-carboxylate

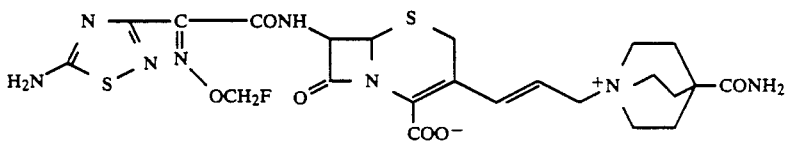

The compound (500 mg) obtained in Experiment 4 was reacted with 4-carbamoylquinuclidine (107.6 mg), followed by removing the protective group, to obtain the desired product (77 mg).

EXAMPLE 139

7β-[2-(5-Amino-1,2,4-thiadiazol-3-yl)-(Z)-2-fluoromethoxyiminoacetamido]-3-[(E)-3-[1-methyl-2-(2-hydroxyethyl)pyrrolidinio]-1-propen-1-yl]-3-cephem-4-carboxylate (Isomers: A and B)

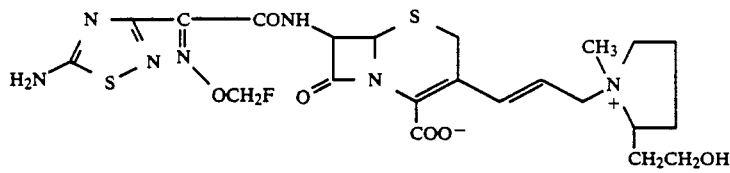

The compound (500 mg) obtained in Experiment 4 was reacted with 1-methyl-2-(2-hydroxyethyl)pyrrolidine (83.3 mg), followed by removing the protective group, to obtain the desired isomer A (24 mg) and isomer B (26 mg).

EXAMPLE 140

7β-[2-(5-Amino-1,2,4-thiadiazol-3-yl)-(Z)-2-fluoromethoxyiminoacetamido]-3-[(E)-3-(4-carboxymethylpyridinio)-1-propen-1-yl]-3-cephem-4-carboxylate

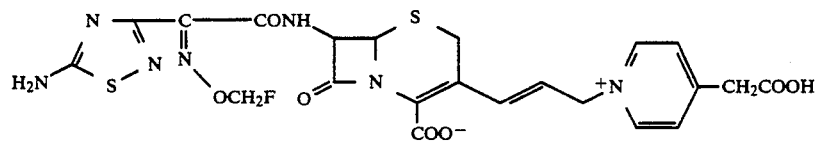

The compound (500 mg) obtained in Experiment 4 was reacted with 4-pyridyl acetic acid hydrochloride (280 mg), followed by removing the protective group, to obtain the desired product (5 mg).

EXAMPLE 141

7β-[2-(5-Amino-1,2,4-thiadiazol-3-yl)-(Z)-2-fluoromethoxyiminoacetamido]-3-[(E)-3-(1,4,4-trimethyl-1-piperazinio)-1-propen-1-yl]-3-cephem-4-carboxylate iodide

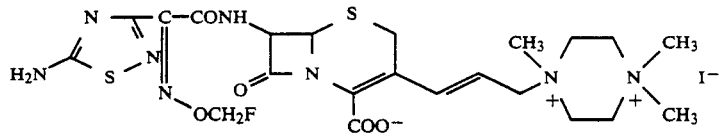

The compound (1.0 g) obtained in Experiment 4 was suspended in ethyl ether (100 ml), and the ethyl acetate solution (40 ml) of 1,4-dimethylpiperazine (189 μl) was dropwise added thereto and stirred overnight. The precipitate formed was collected by filtration, and this was further re-precipitated in tetrahydrofuran/ethyl acetate and then washed with ethyl acetate to obtain an yellow powder (492 mg). This was dissolved in dichloromethane (2 ml), and methyl iodide (4 ml) was added thereto with ice-cooling and then stirred overnight at the same temperature. The reaction solution was put into ethyl acetate, and the precipitate formed was collected by filtration to obtain an yellowish brown powder (190 mg).

This powder was added to a mixture solution comprising trifluoroacetic acid (1.35 ml) and anisole (1.16 ml) and stirred for 2 hours with ice-stirring. The reaction solution was added to a mixture solution comprising ethyl ether (25 ml) and isopropyl ether (25 ml), and the precipitate formed was collected by filtration and washed with ethyl ether. The resulting precipitate was suspended in water (4.5 ml), and the insoluble substances was removed by filtration. The filtrate was purified by reversed phase-silica gel column chromatography to obtain the desired product (23 mg).

EXAMPLE 142

7β-[2-(5-Amino-1,2,4-thiadiazol-3-yl)-(Z)-2-(2,2,2-trifluoroethyl)oxyiminoacetamido]-3-[(E)-3-(carbamoylmethyldimethylammonio)-1-propen-1-yl]-3-cephem-4-carboxylate

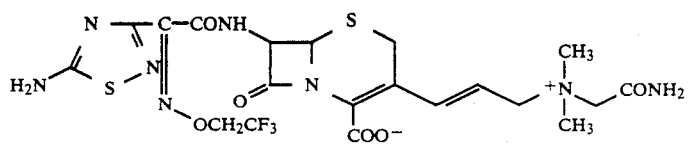

The compound (1.43 g) obtained in Experiment 7 was dissolved in acetone (20 ml), and sodium iodide (0.927 g) was added thereto with ice-cooling and stirred for 10 minutes at the same temperature and successively for 1 hour and 30 minutes at room temperature. The solvent was evaporated out, and after ethyl acetate was added to the resulting residue, this was washed with a diluted sodium thiosulfate solution and saturated brine and then dried with sodium sulfate as added. The brine was evaporated out, and the residue was dissolved in ethyl acetate (40 ml). Afterwards, dimethylglycinamide (237 mg) was added to the resulting solution and stirred for one hour at room temperature. To the resulting solution was added isopropyl ether, and the precipitate formed was collected by filtration, to obtain an yellowish brown powder (1.07 g).

The powder was added to a mixture solution comprising trifluoroacetic acid (8 ml) and anisole (6 ml) and stirred for one hour with ice-cooling. Ethyl ether was added to the resulting reaction solution, and the precipitate formed was collected by filtration. This precipitate was suspended in water (10 ml), followed by adjusting the pH of the resulting suspension to the range of from 5.5 to 6.5 with sodium acetate, and the insoluble substances were removed by filtration. The filtrate was purified by reversed phase-silica gel column chromatography to obtain the desired product (268 mg).

List of physical data

| Experiment No. | Infrared absorption spectrum (cm⁻¹, Nujol) | NMR Spectrum (δ) |
|---|---|---|

-continued

List of physical data

| Example No. | Infrared absorption spectrum (cm$^{-1}$, Nujol) | NMR Spectrum ($\delta$) |
|---|---|---|
| 7 | — | (CDCl$_3$)3.22(1H, d, J=17.0Hz), 3.50(1H, d, J=17.0Hz), 3.55~3.95(2H, m), 3.74(3H, s), 4.62(2H, q, J=8.3Hz), 5.01(1H, d, J=4.7Hz), 5.08(2H, s), 5.66(1H, dt, J=11.0Hz, 7.8Hz), 5.85(1H, dd, J=8.5Hz, 4.7Hz), 6.18(1H, d, J=11.0Hz), 6.61(1H, d, J=8.5Hz), 6.78(2H, d, J=8.5Hz), 7.0~7.4(17H, m), 7.48(1H, brs) |
| 118 | 1760, 1670, 1590 | (DMSO-d$_6$)3.14(3H, s), 3.15(3H, s), 3.47(1H, d, J=17Hz), 3.65(1H, d, J=17Hz), 4.02(2H, s), 4.16(2H, d, J=8Hz), 5.06(1H, d, J=5Hz), 5.65(1H, dd, J=5Hz, 8Hz), 5.70(1H, m), 5.80(2H, d, J=55Hz), 7.16(1H, d, J=15Hz), 7.64(1H, s), 8.19(1H, s), 8.22(2H, s), 9.70(1H, d, J=8Hz) |
| 119 | 1765, 1670, 1600 | (DMSO-d$_6$)3.01(3H, s), 3.2~3.6(9H, m), 3.65(1H, d, J=17Hz), 4.12(2H, d, J=7Hz), 5.06(1H, d, J=5Hz), 5.65(1H, dd, J=5Hz, 8Hz), 5.7(1H, m), 5.78(2H, d, J=55Hz), 7.14(2H, s), 7.21(1H, d, J=16Hz), 8.22(2H, s), 9.70(1H, d, J=8Hz) |
| 120 | 1760, 1665, 1595 | (DMSO-d$_6$)3.09(6H, s), 3.48(1H, d, J=17Hz), 3.67(1H, d, J=17Hz), 4.15(2H, d, J=8Hz), 4.97(2H, s), 5.07(1H, d, J=5Hz), 5.65(1H, dd, J=5Hz, 8Hz), 5.70(1H, m), 5.78(2H, d, J=55Hz), 7.22(1H, d, J=16Hz), 8.22(2H, s), 9.47(1H, s), 9.71(1H, d, J=8Hz) |
| 121 | 1765, 1650, 1590 | (DMSO-d$_6$)3.01(3H, s), 3.15~3.4(4H, m), 3.4~3.55(3H, m), 3.67(1H, d, J=18Hz) 3.7~3.8(2H, m), 4.11(2H, m), 5.07(1H, d, J=5Hz), 5.66(1H, dd, J=5Hz, 8Hz), 5.70(1H, m), 5.78(2H, d, J=55Hz), 6.27(2H, s), 7.19(1H, d, J=16Hz), 8.20(2H, s), 9.70(1H, d, J=8Hz) |
| 122-A | 1765, 1660, 1595 | (DMSO-d$_6$)2.15(2H, m), 2.66(3H, s), 3.0(2H, m), 3.02(2H, m), 3.45(1H, d, J=17Hz), 3.58(1H, d, J=17Hz), 3.55~3.75(2H, m), 4.03(1H, dd, J=8Hz, 13Hz), 4.19(1H, dd, J=8Hz, 13Hz), 5.06(1H, d, J=5Hz), 5.64(1H, dd, J=5Hz, 8Hz), 5.65(1H, m), 5.78(2H, d, J=55Hz), 7.19(1H, d, J=16Hz), 8.21(2H, s), 9.70(1H, d, J=8Hz) |
| 122-B | 1760, 1665, 1590 | (DMSO-d$_6$)2.16(2H, m), 2.66(3H, s), 3.0(2H, m), 3.01(3H, s), 3.45(1H, d, J=17Hz), 3.58(1H, d, J=17Hz), 3.6~3.8(2H, m), 4.01(1H, dd, J=7Hz, 13Hz), 4.21(1H, dd, J=7Hz, 13Hz), 5.06(1H, d, J=5Hz), 5.64(1H, dd, J=5Hz, 8Hz), 5.65(1H, m), 5.78(2H, d, J=55Hz), 7.19(1H, d, J=16Hz), 8.21(2H, s), 9.69(1H, d, J=8Hz) |
| 123 | 1760, 1660, 1590 | (DMSO-d$_6$)3.12(3H, s), 3.50(1H, d, J=18Hz), 3.55(4H, m), 3.72(1H, d, J=18Hz), 3.85~4.15(4H, m), 4.20(2H, d, J=8Hz), 5.11(1H, d, J=5Hz), 5.71(1H, dd, J=5Hz, 8Hz), 5.79(2H, d, J=55Hz), 5.80(1H, m), 7.19(1H, d, J=15Hz), 8.08(1H, s), 8.22(2H, s), 9.71(1H, d, J=8Hz), 9.70(1H, br) |
| 124 | 1765, 1670, 1625 | (DMSO-d$_6$)3.05(3H, s), 3.17(4H, m), 3.35(4H, m), 3.60(1H, d, J=18Hz), 3.95(1H, d, J=18Hz), 4.14(1H, dd, J=7Hz, 13Hz), 4.21(1H, dd, J=7Hz, 13Hz), 5.21(1H, d, J=5Hz), 5.79(2H, d, J=55Hz), 5.85(1H, dd, J=5Hz, 8Hz), 6.12(1H, m), 7.07(1H, d, J=15Hz), 8.21(2H, s), 9.78(1H, d, J=8Hz) |
| 125 | 1765, 1660, 1605 | (DMSO-d$_6$)3.49(1H, d, J=17Hz), 3.63(1H, d, J=17Hz), 5.12(1H, d, J=5Hz), 5.31(2H, d, J=7Hz), 5.74(1H, dd, J=5Hz, 8Hz), 5.78(2H, d, J=55Hz), 6.07(1H, dd, J=8Hz, 16Hz), 7.07(1H, d, J=16Hz), 7.20(1H, br), 8.19(2H, d, J=7Hz), 8.20(2H, s), 8.89(2H, d, J=7Hz), 9.75(1H, d, J=8Hz) |
| 126 | 1755, 1650, 1590 | (DMSO-d$_6$)2.07(4H, br), 2.95(3H, s), 3.3~3.4(4H, m), 3.45(1H, d, J=17Hz), 3.61(1H, d, J=17Hz), 3.99(2H, d, J=7Hz), 5.06(1H, d, J=5Hz), 5.63(1H, dd, J=5Hz, 8Hz), 5.7(1H, m), 5.78(2H, d, J=55Hz), 7.18(1H, d, J=16Hz), 8.22(2H, s), 9.69(1H, d, J=8Hz) |
| 127 | 1760, 1665, 1595 | (DMSO-d$_6$)3.41(1H, d, J=17.2Hz), 3.48(1H, d, J=17.2Hz), 5.04(1H, d, J=4.8Hz), 5.35(2H, d, J=7.0Hz), 5.64(1H, dd, J=4.8Hz, 8.5Hz), 5.78(2H, d, J=55.3Hz), 5.88(1H, dd, J=15.8Hz, 7.0Hz), 7.25(1H, d, J=15.8Hz), 8.22(2H, s), 8.24(1H, s), 8.43(2H, d, J=6.8Hz), 8.79(1H, s), 9.19(2H, d, J=6.8Hz), 9.71(1H, d, J=8.5Hz) |
| 128 | 1765, 1595 | (DMSO-d$_6$)2.99(9H, s), 3.46(1H, d, J=17.0Hz), 3.63(1H, d, J=17.0Hz), 3.98(2H, d, J=7.3Hz), 5.05(1H, d, J=5.0Hz), 5.60~5.70(2H, m), 5.78(2H, d, J=55.3Hz), 7.18(1H, d, J=15.8Hz), 8.25(2H, s), 9.84(1H, d, J=8.4Hz) |
| 129 | 1760, 1595 | (DMSO-d$_6$)2.90~3.10(6H, m), 3.15~3.35(6H, m), 3.46(1H, d, J=16.9Hz), 3.60(1H, d, J=16.9Hz), 3.92(2H, d, J=7.3Hz), 5.05(1H, d, J=5.1Hz), 5.50~5.70(2H, m), 5.79(2H, d, J=55.3Hz), 7.17(1H, d, J=15.8Hz), 8.25(2H, s), 9.70(1H, d, J=8.0Hz) |
| 130 | 1760, 1595 | (DMSO-d$_6$)2.15~2.37(4H, m), 3.00~3.15(2H, m), 3.20~3.35(2H, m), 3.44(1H, d, J=16.9Hz), 3.54(1H, d, J=16.9Hz), 3.60~3.82(4H, m), 4.08(2H, d, J=6.6Hz), 5.05(1H, d, J=5.1Hz), 5.60~5.70(2H, m), 5.79(2H, d, J=55.3Hz), 7.19(1H, d, J=15.8Hz), 8.24(2H, s), 9.70(1H, d, J=8.5Hz) |
| 131 | 1765, 1670, 1600 | (DMSO-d$_6$)3.16(3H, s), 3.47(1H, d, J=17Hz), 3.65~3.75(5H, m), 3.80~3.90(4H, m), 4.27(1H, dd, J=7Hz, 13Hz), 4.33(1H, dd, J=7Hz, 13Hz), 5.09(1H, d, J=5Hz), 5.67(1H, dd, J=5Hz, 8Hz), 5.7~5.8(1H, m), 5.79(2H, d, J=55Hz), 7.26(1H, d, J=15Hz), 8.21(1H, d, J=8Hz) |
| 132 | 1765, 1670, 1595 | (DMSO-d$_6$)2.27(3H, s), 2.60(2H, m), 2.75(2H, m), 2.97(3H, s), 3.3(4H, m), 3.45(1H, d, J=17Hz), 3.63(1H, d, J=17Hz), 4.07(2H, d, J=8Hz), 5.05(1H, d, J=5Hz), 5.64(1H, dd, J=5Hz, 8Hz), 5.69(1H, m), 5.78(2H, d, J=55Hz), 7.20(1H, d, J=16Hz), 8.22(2H, s), 9.70(1H, d, J=8Hz) |
| 133 | 1765, 1670, 1600 | (DMSO-d$_6$)3.27(6H, s), 3.65(2H, m), 3.72(2H, m), 3.78(1H, d, J=17Hz), 3.84(1H, d, J=17Hz), 4.22(2H, d, J=8Hz), 5.40(1H, d, J=5Hz), 5.97(2H, d, J=55Hz), 5.98(1H, d, J=5Hz), 6.09(1H, dt, J=8Hz, 16Hz), 7.07(1H, d, J=16Hz) |
| 134 | 1760, 1665, 1595 | (DMSO-d$_6$)2.89(3H, s), 2.90(3H, s), 3.50(1H, d, J=17Hz), 3.67(1H, d, J=17Hz), 3.96(1H, d, J=7Hz), 4.61(2H, s), 5.08(1H, d, J=5Hz), 5.66(1H, dd, J=5Hz, 8Hz), 5.79(2H, d, J=56Hz), 5.82(1H, dt, J=7Hz, 15Hz), 7.20(1H, d, J=15Hz), 8.21(2H, s), 9.72(1H, d, J=8Hz) |
| 135 | 1765, 1670, 1620, 1590, 1530, 1240, 1215 | (DMSO-d$_6$)3.46(1H, d, J=17.2Hz), 3.55(1H, d, J=17.2Hz), 5.09(1H, d, J=4.8Hz), 5.39(2H, brs), 5.70(1H, brs), 5.78(2H, d, J=55.3Hz), 5.98(1H, dt, J=15.8Hz, 6.5Hz), 7.20(1H, d, J=15.8Hz), 8.13(1H, dd, J=8.0Hz, 6.0Hz), 8.20(2H, s), 8.69(1H, d, J=8.0Hz), 8.98(1H, d, J=6.0Hz), 9.24(1H, s), 9.73(1H, d, J=8.5Hz) |
| 136 | 1765, 1670, | (DMSO-d$_6$)2.26(6H, s), 2.74(2H, m), 3.04(6H, s), 3.42(2H, m), |

-continued

List of physical data

| | Infrared absorption spectrum (cm$^{-1}$, Nujol) | NMR Spectrum ($\delta$) |
|---|---|---|
| | 1600 | 3.62(1H, d, J=18Hz), 3.98(1H, d, J=18Hz), 4.11(2H, d, J=8Hz), 5.23(1H, d, J=5Hz), 5.79(2H, d, J=55Hz), 5.86(1H, m), 6.13(1H, dt, J=8Hz, 15Hz), 7.02(1H, d, J=15Hz), 8.21(2H, s), 9.79(1H, d, J=8Hz) |
| 137 | 1760, 1665, 1595 | (DMSO-d$_6$)2.17(3H, s), 3.09(3H, s), 3.10(3H,s), 3.45(1H, d, J=17Hz), 3.63(1H, d, J=17Hz), 4.10(2H, d, J=8Hz), 4.48(2H, s), 5.06(1H, d, J=5Hz), 5.64(1H, dd, J=5Hz, 8Hz), 5.68(1H, dt, J=8Hz, 16Hz), 5.79(2H, d, J=55Hz), 7.12(1H, d, J=16Hz), 8.22(2H, s), 9.70(1H, d, J=8Hz) |
| 138 | 1760, 1655, 1590 | (DMSO-d$_6$)3.25~3.45(12H, m), 3.45(1H, d, J=17Hz), 3.61(1H, d, J=17Hz), 3.88(2H, d, J=7Hz), 5.06(1H, d, J=5Hz), 5.62(1H, m), 5.63(1H, dd, J=5Hz, 8Hz), 5.78(2H, d, J=55Hz), 7.11(1H, s), 7.15(1H, d, J=16Hz), 7.34(1H, s), 8.23(2H, s), 9.70(1H, d, J=8Hz) |
| 139-A | 1760, 1650, 1590 | (DMSO-d$_6$)1.6~2.4(6H, m), 3.00(3H, s), 3.2~3.7(5H, m), 3.44(1H, d, J=17Hz), 3.66(1H, d, J=17Hz), 3.69(2H, d, J=8Hz), 5.06(1H, d, J=5Hz), 5.64(1H, dd, J=5Hz, 8Hz), 5.67(1H, m), 5.78(2H, d, J=55Hz), 7.18(1H, d, J=15Hz), 8.24(2H, s), 9.69(1H, d, J=8Hz) |
| 139-B | 1760, 1650, 1590 | (DMSO-d$_6$)1.6~2.4(6H, m), 3.00(3H, s), 3.2~3.7(5H, m), 3.46(1H, d, J=17Hz), 3.63(1H, d, J=17Hz), 3.75(2H, d, J=7Hz), 5.06(1H, d, J=5Hz), 5.64(1H, dd, J=5Hz, 8Hz), 5.67(1H, m), 5.79(2H, d, J=55Hz), 7.16(1H, d, J=16Hz), 8.21(2H, s), 9.70(1H, d, J=8Hz) |
| 140 | — | (DMSO-d$_6$)5.02(1H, d, J=4.8Hz), 5.22(2H, d, J=6.6Hz), 5.61(1H, dd, J=4.8Hz, 8.4Hz), 5.77(2H, d, J=55Hz), 5.8~5.9(1H, m), 7.31(1H, d, J=15.0Hz), 7.97(2H, d, J=6.2Hz), 8.20(2H, s), 8.86(2H, d, J=6.2Hz), 9.70(1H, d, J=8.4Hz) |
| 141 | 1760, 1670, 1595 | (DMSO-d$_6$)3.09(6H, s), 3.18(3H, s), 3.51(1H, d, J=17Hz), 3.74(1H, d, J=17Hz), 3.83(8H, br), 4.34(2H, m), 5.12(1H, d, J=5Hz), 5.73(1H, m), 5.78(2H, d, J=55Hz), 5.83(1H, m), 7.24(1H, d, J=15Hz), 8.21(2H, s), 9.92(1H, d, J=8Hz) |
| 142 | 1762, 1680, 1590 | (DMSO-d$_6$)3.10(6H, s), 3.3~3.7(2H, m), 3.9~4.3(4H, m), 4.71(2H, q, J=9.0Hz), 4.98(1H, d, J=5.0Hz), 5.4~5.8(2H, m), 7.13(1H, d, J=15.5Hz), 7.55(1H, brs), 8.17(2H, brs), 8.40(1H, brs), 9.57(1H, d, J=8.0Hz) |

EXAMPLE 143

7$\beta$-[2-(5-Amino-1,2,4-thiadiazol-3-yl)-(Z)-2-fluoromethoxyiminoacetamido]-3-[(E)-3-[tris(2-hydroxyethyl)ammonio]-1-propen-1-yl]-3-cephem-4-carboxylate

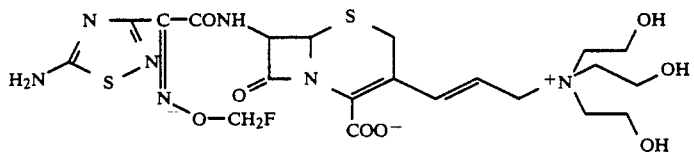

400 Mg of the compound prepared in the Experiment 4 was dissolved in 4 ml of ethyl acetate, and 96 mg of triethanolamine solution in 4 ml of ethyl acetate was added thereto. The resulting solution was stirred for 6 hours at the room temperature. To the reaction solution was added 24 ml of diisopropyl ether, and the resulting precipitates were collected by filtration. This precipitates were added to 4.5 ml of a mixed solution containing trifluoro acetic acid and anisole (1:1) under ice-cooling. The mixture was stirred for one hour and 30 minutes at the room temperature. To the reaction solution was added 18 ml of diisopropyl ether. The resulting precipitates were collected by filtration, and washed with diisopropyl ether. This precipitates were suspended, in 3 ml of water, and sodium acetate was added thereto to adjust the resulting solution to pH 6. Insolubles were removed by filtration, and the filtrate was purified by a reversed-phase silica gel column chromatography to obtain 17 mg of the objective product.

EXAMPLE 144

7$\beta$-[2-(5-Amino-1,2,4-thiadiazol-3-yl)-(Z)-2-fluoromethoxyiminoacetamido]-3-[(E)-3-[bis(2-hydroxyethyl)methylammonio]-1-propen-1-yl]-3-cephem-4-carboxylate

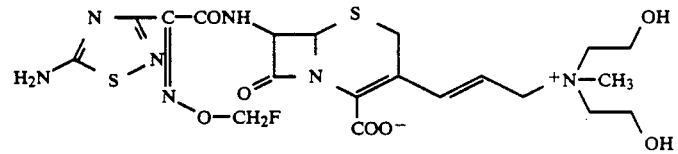

In the same manner as the Example 143, 500 mg of the compound prepared in the Experiment 4 was reacted with 150 mg of N-methyldiethanolamine, and the protecting group was eliminated to obtain 15 mg of the objective product.

| Example No. | Infrared absorption spectrum (cm$^{-1}$, Nujol) | NMR Spectrum ($\delta$) |
|---|---|---|
| 143 | — | (DMSO-d$_6$)3.43(6H, brs), 3.47(1H, d, J=17Hz), 3.69(1H, d, J=17Hz), |

| Example No. | Infrared absorption spectrum (cm$^{-1}$, Nujol) | NMR Spectrum (δ) |
|---|---|---|
| | | 3.84(6H, brs), 4.16(2H, d, J=7Hz), 5.07(1H, d, J=5Hz), 5.67(1H, dd, J=8Hz, 5Hz), 5.7~5.8(1H, m), 5.78(2H, brd, J=56Hz), 7.15(1H, d, J=16Hz), 8.21(2H, s), 9.70(1H, d, J=8Hz) |
| 144 | 1760, 1670, 1600 | (D$_2$O)3.23(3H, s), 3.60~3.70(4H, m), 3.77(1H, d, J=17.6Hz), 3.83(1H, d, J=17.6Hz), 4.1~4.2(4H, m), 4.27(2H, d, J=7.4Hz), 5.39(1H, d, J=4.8Hz), 5.96(2H, d, J=54.6Hz), 5.98(1H, d, J=4.8Hz), 6.0~6.1(1H, m), 7.03(1H, d, J=15.7Hz) |

EXPERIMENT 8

Synthesis of the raw material compound 2-(5-Tritylamino-1,2,4-thiadiazol-3-yl)-(Z)-2-cyanomethoxyiminoacetic acid

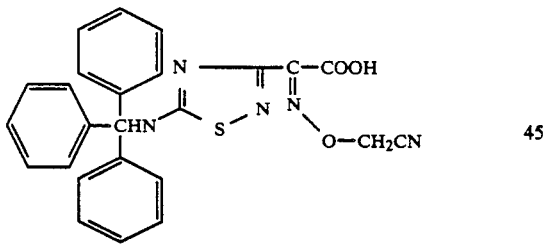

8.00 g of N-cyanomethoxyphthalimide was suspended in 50 ml of ethanol and 1.93 ml of hydrazine monohydride was added thereto at room temperature. The resulting mixture was stirred for 1 hour and 45 minutes. Then a saturated brine and ethyl ether were added thereto. The mixture was made basic with conc. aqueous ammonia and then extracted with ethyl ether. The ethyl ether layer was washed with a saturated brine solution and dried over anhydrous sodium sulfate. Subsequently the solvent was distilled off.

To the residue, 350 ml of methanol and 650 g of 2-(5-tritylamino-1,2,4-thidiazol-3-yl)glyoxylic acid were added and the resulting mixture was stirred at room temperature for one hour. After distilling off the solvent, the residue was dissolved in ethyl acetate and then washed with 0.1N hydrochloric acid, followed by with a saturated brine solution. After drying the organic layer over anhydrous sodium sulfate, the solvent was distilled off. Thus 7.64 g of the objective compound was obtained.

EXPERIMENT 9

Synthesis of the raw material compound p-Methoxybenzyl 7β-[2-(5-tritylamino-1,2,4-thiadiazol-3-yl)-(Z)-2-cyanomethoxyiminoacetamido]-3-[(Z)-3-chloro-1-propen-1-yl]-3-cephem-4-carboxylate

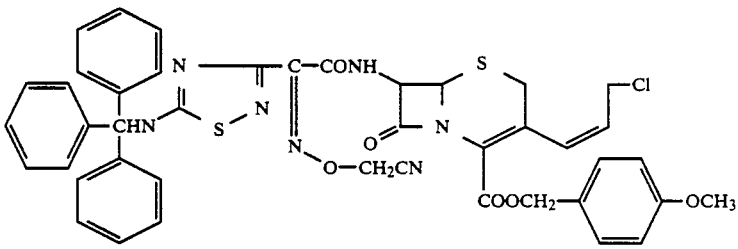

1.51 ml of dimethylformamide and 18 ml of tetrahydrofuran were cooled to −10° C. and 1.82 ml of phosphoryl chloride was added thereto. The resulting mixture was stirred for 40 minutes under ice-cooling. Then a solution of 7.64 g of the compound of Experiment 8 in 24 ml of tetrahydrofuran was added thereto and the resulting mixture was stirred at the same temperature for additional one hour.

A solution comprising 6.00 g of p-methoxybenzyl 7β-amino-3-[(Z)-3-chloro-1-propen-1-yl]-3-cephem-4-carboxylate hydrochloride, 12.8 g of N-trimethylsilylacetamide and 60 ml of ethyl acetate was cooled to −25° C. Then the above-mentioned reaction mixture was added thereto and the resulting mixture was stirred for 40 minutes while raising the temperature to 0° C. This reaction mixture was extracted with ethyl acetate and the organic layer was washed with a saturated brine solution and dried over anhydrous sodium sulfate. After distilling off the solvent, the residue was purified with silica gel column chromatography. Thus 7.80 g of the objective compound was obtained.

EXPERIMENT 10

Synthesis of the raw material compound p-Methoxybenzyl 7β-[2-(5-tritylamino-1,2,4-thiadiazol-3-yl)-(Z)-2-cyanomethoxyiminoacetamido]-3-[(E)-3-iodo-1-propen-1-yl]-3-cephem-4-carboxylate

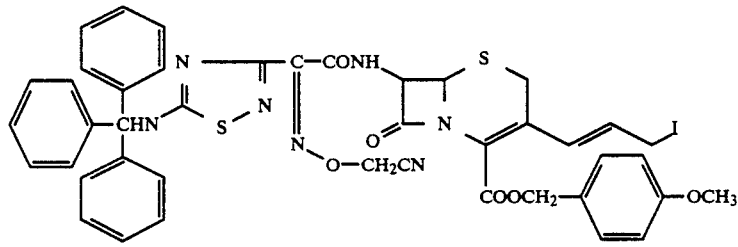

To a solution of 7.80 g of the compound of Experiment 9 in 120 ml of acetone, 6.9 g of sodium iodide was added under ice-cooling. The resulting mixture was stirred for 10 minutes and then for additional 1 hour and 30 minutes at room temperature. The solvent was distilled off and the residue was extracted with ethyl acetate. The extract was washed with a dilute aqueous solution of sodium thiosulfate followed by with a saturated brine solution and then dried over anhydrous sodium sulfate. The solution was concentrated and added dropwise to a mixture of isopropyl ether and ethyl ether. The precipitate thus formed was filtered out to thereby give 6.50 g of the objective compound.

EXAMPLE 145

7β-[2-(5-Amino-1,2,4-thiadiazol-3-yl)-(Z)-2-cyanomethoxyiminoacetamido]-3-[(E)-3-[(1S-carbamoyl-2-hydroxyethyl)dimethylammonio]-1-propen-1-yl]-3-cephem-4-carboxylate

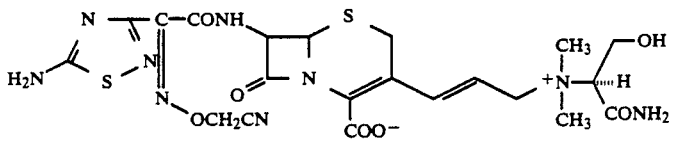

1.0 g of the compound of Experiment 10 was dissolved in 2 ml of dimethylformamide and 210 mg of (1S-carbamoyl-2-hydroxyethyl)dimethylamine was added thereto at room temperature. The resulting mixture was stirred for one hour and then diluted by adding 10 ml of ethyl acetate thereto. The resulting solution was added dropwise to 100 ml of ethyl ether to thereby give 710 mg of a brown precipitate.

This precipitate was stirred in a mixture of 6 ml of anisole and 6.5 ml of trifluoroacetic acid under ice-cooling for one hour. Then ethyl ether was added to the reaction mixture to thereby give 430 mg of a brown precipitate. This precipitate was suspended in 10 ml of water and the pH value of the obtained suspension was adjusted to 7.0 with sodium acetate. After filtering off the insoluble matters, the filtrate was purified with reverse phase silica gel column chromatography to thereby give 50 mg of the objective compound.

EXAMPLE 146

7β-[2-(5-Amino-1,2,4-thiadiazol-3-yl)-(Z)-2-cyanomethoxyiminoacetamido]-3-[(E)-3-(1-methyl-2R-hydroxymethyl-4R-hydroxy-1-pyrrolidinio)-1-propen-1-yl]-3-cephem-4-carboxylate

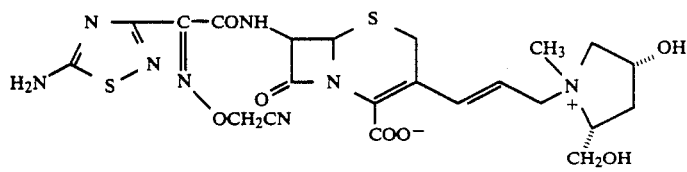

1.0 g of the compound of Experiment 10 was dissolved in a mixture of 10 ml of ethyl acetate and 8 ml of ethyl ether. Then 167 mg of N-methyl-4R-hydroxy-D-prolinol was added thereto and the resulting mixture was stirred overnight. The reaction mixture was added to 100 ml of ethyl ether and the precipitate thus formed was filtered out to thereby give 840 mg of a yellow powder.

To this powder, 6 ml of anisole was added and 8 ml of trifluoroacetic acid was added dropwise to the resulting mixture under ice-cooling for 30 minutes. Then the mixture was stirred for additional 1 hour and 30 minutes. 100 ml of ethyl ether was added to the reaction mixture and the precipitate thus formed was filtered out and suspended in 4 ml of water. The pH value of the resulting suspension was adjusted to 7.0 with sodium acetate. After filtering off the insoluble matters, the filtrate was purified with reverse phase silica gel column chromatography to thereby give 24 mg of the objective compound.

The following compounds of Examples 147-154 were obtained in the same manner as those described in Examples 145 and 146,

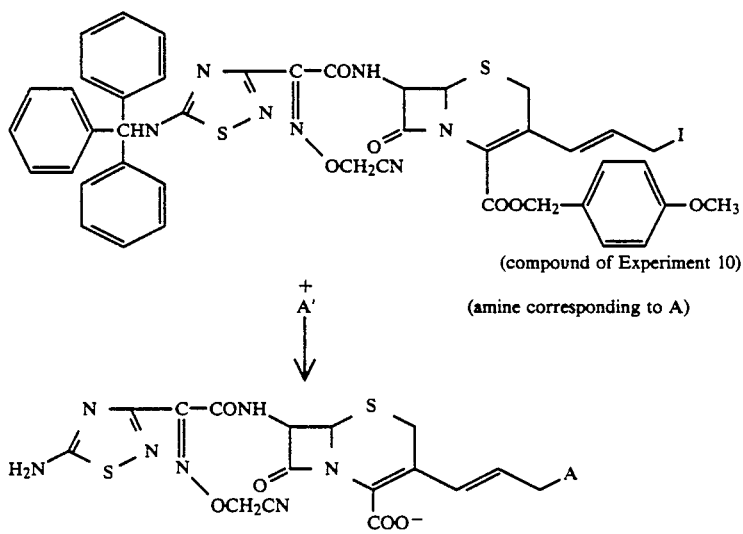

(compound of Experiment 10)

+ A′ (amine corresponding to A)

↓

In a case where plural isomers were formed depending on the ammonio group of A, the yield of each isomer, if isolated, was given.

| Example No. | A | A′ (amine) | Compound of Experiment 10 | Yield of the objective product |
|---|---|---|---|---|
| 147 | —⁺N(CH₂CH₂OH)₃ | 960 mg | 3.0 g | 37 mg |
| 148 | —⁺N(CH₃)₂—C(CH₃)(H)—CH₂OH | 500 mg | 1.0 g | 50 mg |
| 149 | —⁺N(CH₃)₂—CH₂—CH(OH)CH₃ | 0.19 ml (racemate) | 1.0 g | 113 mg (1:1 Mixture) |
| 150 | —⁺N(CH₃)₂—C(CH₃)(H)—CONH₂ | 250 mg; (H₃C)₂N—CH(CH₃)—CONH₂ (racemate) | 1.0 g | 43 mg |
| 151 | —⁺N(CH₃)₂—C(CH₃)(H)—CONH₂ | | | 24 mg |
| 152 | pyrrolidinium with OH and CH₂OH | 120 mg | 800 mg | 120 mg |

-continued

| Example No. | A | Use amount of the starting compound A' (amine) | Compound of Experiment 10 | Yield of the objective product |
|---|---|---|---|---|
| 153 | CH₃ group with —⁺N(CH₃)₂—CH(CONH₂)—CH(OH)(H)—CH₃ | 470 mg | 2.0 g | 31 mg |
| 154 | —⁺N(CH₃)₂—CH₂—C(=O)—CH₃ | 0.32 ml | 2.0 g | 120 mg |

List of Physical Data

| | Infrared absorption spectrum (cm⁻¹, Nujol) | NMR Spectrum (δ) |
|---|---|---|
| Experiment No. | | |
| 8 | — | (CDCl₃)4.86(2H, s), 7.29(15H, s), 8.10(1H, brs) |
| 9 | — | (CDCl₃)3.25–3.6(2H, m), 3.6–4.1(2H, m), 3.75(3H, s), 4.90(2H, s), 5.02(1H, d, J=5.0Hz), 5.08(2H, s), 5.66(1H, dt, J=11.3Hz, 7.7Hz), 5.82(1H, dd, J=9.0Hz, 5.5Hz), 6.18(1H, d, J=11.3Hz), 6.79(2H, d, J=8.6Hz), 6.95(1H, d, J=9.0Hz), 7.0–7.35(17H, brs), 7.59(1H, brs) |
| 10 | 1770, 1715, 1675, 1605 | (CDCl₃)3.35–3.65(2H, m), 3.74(3H, s), 3.8–4.10(2H, m), 4.86(2H, s), 4.95(1H, d, J=5.0Hz), 5.13(2H, s), 5.7–6.35(3H, m), 6.5–7.4(20H, m), 7.66(1H, brs) |
| Example No. | | |
| 145 | 1770, 1685, 1600, 1530 | (DMSO-d₆)3.08(3H, s), 3.15(3H, s), 3.48(1H, d, J=17.0Hz), 3.67(1H, d, J=17.0Hz), 3.87(1H, dd, J=8.1Hz, 14.3Hz), 4.05~4.15(2H, m), 4.15~4.25(2H, m), 5.07(1H, d, J=4.8Hz), 5.10(2H, s), 5.66(1H, dd, J=4.8Hz, 8.1Hz), 5.75~5.85(1H, m), 7.14(1H, d, J=15.8Hz), 7.75(1H, s), 8.24(2H, s), 8.38(1H, d, J=8.1Hz), 9.73(1H, d, J=8.1Hz) |
| 146 | 1765, 1660, 1595, 1530 | (DMSO-d₆)1.78(1H, m), 2.55(1H, m), 3.04(3H, s), 3.47(1H, d, J=16.9Hz), 3.6~4.0(5H, m), 3.66(1H, d, J=16.9Hz), 4.18(2H, m), 4.45(1H, brs), 5.05(1H, d, J=5.1Hz), 5.10(2H, s), 5.6~5.8(1H, m), 5.63(1H, dd, J=5.1Hz, 8.1Hz), 7.13 and 7.17(total 1H, d, J=15.9Hz), 8.24(2H, s), 9.71(1H, d, J=8.1Hz) |
| 147 | 1765, 1670, 1600 | (DMSO-d₆)3.40~3.50(7H, m), 3.67(1H, d, J=17.2Hz), 3.85(6H, brs), 4.10~4.25(2H, m), 5.06(1H, d, J=5.0Hz), 5.10(1H, s), 5.65(1H, dd, J=5.0Hz, 8.3Hz), 5.75(1H, dt, J=7.0Hz, 15.8Hz), 7.14(1H, d, J=15.8Hz), 8.24(2H, s), 9.71(1H, d, J=8.3Hz) |
| 148 | 1760, 1660, 1590, 1520 | (DMSO-d₆)1.32(3H, d, J=6.6Hz), 2.94(3H, s), 2.98(3H, s), 3.40~3.50(1H, m), 3.47(1H, d, J=16.9Hz), 3.65(1H, d, J=16.9Hz), 3.65~3.75(1H, m), 3.80~3.90(1H, m), 4.04(2H, brd, J=7.7Hz), 5.05(1H, d, J=4.8Hz), 5.10(2H, s), 5.63(1H, dd, J=4.8Hz, 8.4Hz), 5.65~5.75(1H, m), 7.18(1H, d, J=15.8Hz), 8.26(2H, s), 9.71(1H, d, J=8.4Hz) |
| 149 | 1765, 1670, 1600, 1530 | (DMSO-d₆)1.11(3H, d, J=6.2Hz), 3.01(3H, s), 3.04(3H, s), 3.22(2H, brs), 3.47(1H, d, J=17.2Hz), 3.63 and 3.66(total 1H, d, J=17.2Hz), 4.05(2H, brs), 4.26(1H, brs), 5.05(1H, d, J=4.8Hz), 5.10(2H, s), 5.63(1H, dd, J=4.8Hz, 8.4Hz), 5.65~5.75(1H, m), 7.16(1H, d, J=15.4Hz), 8.27(2H, s), 9.71(1H, d, J=8.4Hz) |
| 150 | 1765, 1675, 1595, 1530 | (DMSO-d₆)1.47(3H, d, J=6.6Hz), 3.06(3H, s), 3.08(3H, s), 3.49(1H, d, J=17.0Hz), 3.64(1H, d, J=17.0Hz), 4.0~4.2(3H, m), 5.06(1H, d, J=4.8Hz), 5.10(2H, s), 5.65(1H, dd, J=4.8Hz, 8.4Hz), 5.65~5.80(1H, m), 7.16(1H, d, J=15.8Hz), 7.68(1H, s), 8.25(2H, s), 8.41(1H, s), 9.73(1H, d, J=8.4Hz) |
| 151 | 1765, 1680, 1595, 1530 | (DMSO-d₆)1.45(3H, d, J=6.6Hz), 3.02(3H, s), 3.51(1H, d, J=16.9Hz), 3.65(1H, d, J=16.9Hz), 4.0~4.1(1H, m), 4.35~4.45(2H, m), 5.08(1H, d, J=4.8Hz), 5.10(2H, s), 5.66(1H, dd, J=4.8Hz, 8.1Hz), 5.70~5.85(1H, m), 7.26(1H, d, J=15.4Hz), 7.64(1H, s), 8.24(2H, s), 8.95(1H, s), 9.72(1H, d, J=8.1Hz) |
| 152 | 1765, 1660, 1630, 1600, 1590, 1540 | (DMSO-d₆)1.95~2.10(1H, m), 2.15~2.40(1H, m), 2.93(2H, s), 3.14(1H, s), 3.40~3.65(3H, s), 3.48(1H, d, J=16.9Hz), 3.64(1H, d, J=16.9Hz), 3.65~3.90(2H, m), 3.95~4.10(1H, m), 4.10~4.25(1H, m), 4.40(1H, brs), 5.06(1H, d, J=4.8Hz), 5.10(2H, s), 5.64(1H, dd, J=4.8Hz, 8.4Hz), 5.70~5.85(1H, m), 7.13 and 7.16(total 1H, d, J=15.4Hz), 8.24(2H, s), 9.72(1H, d, J=8.4Hz) |
| 153 | 1760, 1665, 1590, 1520 | (DMSO-d₆)1.20(3H, d, J=6.2Hz), 3.06(3H, s), 3.22(3H, s), 3.49(1H, d, J=17.2Hz), 3.62(1H, d, J=17.2Hz), 3.96(1H, d, J=9.2Hz), 4.15~4.45(3H, s), 5.07(1H, d, J=5.2Hz), 5.10(2H, s), 5.66(1H, dd, J=5.2Hz, 8.4Hz), 5.8~5.9(1H, m), 7.02(1H, d, J=15.8Hz), 7.83(1H, s), 8.24(2H, s), 8.71(1H, s), 9.72(1H, d, J=8.4Hz) |
| 154 | 1760, 1660, 1590, 1520 | (DMSO-d₆)2.16(3H, s), 3.09(3H, s), 3.10(3H, s), 3.46(1H, d, J=17.0Hz), 3.63(1H, d, J=17.0Hz), 4.12(2H, d, J=7.3Hz), 4.51(2H, s), 5.05(1H, d, J=5.1Hz), 5.10(2H, s), 5.63(1H, dd, J=5.1Hz, 8.1Hz), 5.65~5.75(1H, m), 7.13(1H, d, J=15.4Hz), 8.26(2H, s), 9.71(1H, d, J=8.1Hz) |

EXAMPLE 155

7β-[2-(5-Amino-1,2,4-thiadiazol-3-yl)-(Z)-2-cyanomethoxyiminoacetoamido]-3-[(E)-3-carbamoylmethyldimethylammonio)-1-propen-1-yl]-3-cephem-4-carboxylate

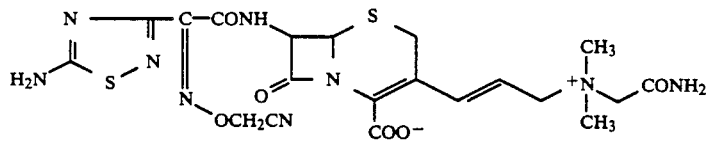

Dimethylglycinamide (64 mg) was added to a solution of the compound (390 mg) of Experiment 10 in ethyl acetate (15 ml), and this mixture was stirred at a room temperature for 1 hour. Ethyl ether was added to the reaction solution and the produced precipitate was filtered and dried, thus providing a yellowish brown powder (260 mg).

A mixture of trifuloroacetic acid (2 ml) and anisole (1.5 ml) was added to this powder and stirred for 1 hour under an ice-cooling condition. Ethyl ether was added to the resulting solution, and the produced precipitate was filtered and washed with ethyl ether. This precipitate was suspended into water (5 ml) and pH of the suspension was adjusted to 5.5 to 6.5, following which the insoluble material was filtered off. The filtrate was refined in a reversed phase chromatography, thus providing the desired material (37 mg).

EXAMPLE 156

7β-[2-(5-Amino-1,2,4-thiadiazol-3-yl)-(Z)-2-cyanomethoxyiminoacetoamido]-3-[(E)-3-(1-methyl-4-sulfamoyl-1-piperazinio)-1-propen-1-yl]-3-cephem-4-carboxylate

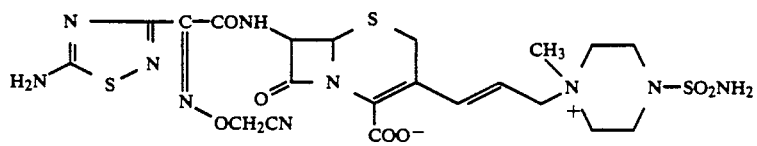

The compound (500 mg) of Experiment 10 was dissolved into a mixture of dichloromethane (5 ml) and methanol (1 ml), and N-sulfamoyl-N'-methylpiperazine (145 mg) was added thereto, and the whole was stirred at a room temperature for 4 hours. The resulting solution was concentrated, and ethyl ether was added thereto. The produced precipitate was filtered and dried; thus providing a yellowish brown powder (450 mg).

A mixture of trifluoroacetic acid (3.5 ml) and anisole (3 ml) was added to this powder, and the whole was stirred for 1 hour. Ethyl ether was added to the resulting solution, and the produced precipitate was filtered and washed with ethyl ether. The precipitate was suspended into water (5 ml) and the pH of the suspension was adjusted to 5.5 to 6.5, following which the insoluble material was filtered off. The filtrate was refined in a reversed phase chromatography, thus providing the desired material (39 mg).

EXAMPLE 157

7β-[2-(5-Amino-1,2,4-thiadiazol-3-yl)-(Z)-2-cyanomethoxyiminoacetoamido]-3-[(E)-3-(1,4-diazabicyclo[2,2,2]octane-1-io)-1-propen-1-yl]-3-cephem-4-carboxylate

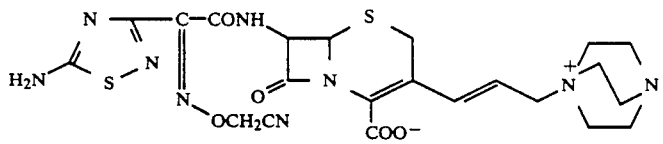

The compound (500 mg) of Experiment 10 was dissolved into a mixture of ethylacetate (6 ml) and methanol (0.5 ml), and 1,4-diazabicyclo[2,2,2]octane (90 mg) was added thereto and stirred at a room temperature for 20 minutes. Ethyl ether was added to the resulting solution, and the produced precipitate was filtered and dried, thus providing a yellowish brown powder (330 mg).

A mixture of trifluoroacetic acid (3 ml) and anisole (2.5 ml) was added to this powder, and the whole was stirred for 1 hour under a ice-cooling condition. Ethyl ether was added to the resulting solution, and the produced precipitate was filtered and washed with ethyl ether. The precipitate was suspended into water (5 ml) and the pH of the suspension was adjusted to 5.5 to 6.5, following which the insoluble material was filttered off.

The filtrate was refined in a reversed phase chromatography, thus providing the desired material (48 mg).

Compounds of the following Examples 158 to 161 were provided in the same manner as in Examples 155 to 157.

EXAMPLE 158

7β-[2-(5-Amino-1,2,4-thiadiazol-3-yl)-(Z)-2-cyanomethoxyiminoacetoamido]-3-[(E)-3-(4-carbamoylpyridinio)-1-propen-1-yl]-3-cephem-4-carboxylate

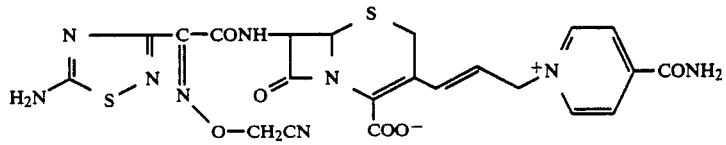

The compound (600 mg) of Experiment 10 was reacted with 4-carbamoylpyridine (235 mg), and the protective group was removed to provide the desired material (37 mg).

EXAMPLE 159

7β-[2-(5-Amino-1,2,4-thiadiazol-3-yl)-(Z)-2-cyanomethoxyiminoacetoamido]-3-[(E)-3-(1,3,4-oxadiazol-2-yl)methyldimethylammonio]-1-propen-1-yl]-3-cephem-4-carboxylate

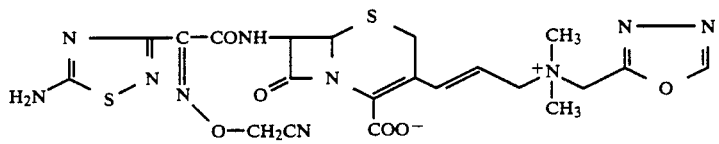

The compound (600 mg) of Experiment 10 was reacted with 2-dimethylaminomethyl-1,3,4-oxadiazol (163 mg), and the protective group was removed to provide the desired material (54 mg).

EXAMPLE 160

7β-[2-(5-Amino-1,2,4-thiadiazol-3-yl)-(Z)-2-cyanomethoxyiminoacetoamido]-3-[(E)-3-(1,2-dimethyl-1-piperazinio)-1-propen-1-yl]-3-cephem-4-carboxylate (isomers: A and B)

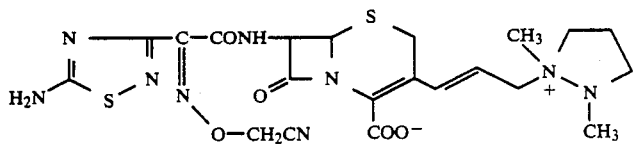

The compound (510 mg) of Experiment 10 was reacted with 1,2-dimethylpyrazolidine (0.4 ml), and the protective group was removed to provide the desired isomer A (20 mg) and the desired isomer B (20 mg).

EXAMPLE 161

7β-[2-(5-Amino-1,2,4-thiadiazol-3-yl)-(Z)-2-cyanomethoxyiminoacetoamido]-3-[(E)-3-(1,5-diazabicyclo[3.3.0]octane-1-io)-1-propen-1-yl]-3-cephem-4-carboxylate

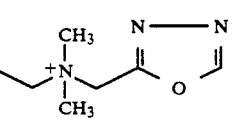

The compound (600 mg) of Experiment 10 was reacted with 1,5-diazabicyclo[3,3,0]octane (220 mg), and the protective group was removed to provide the desired material (39 mg).

| Example No. | Infrared absorption spectrum (cm$^{-1}$, Nujol) | NMR Spectrum (δ) |
|---|---|---|
| 155 | 1760, 1670, 1590 | (DMSO-d$_6$)3.10(6H, s), 3.4–3.7(2H, m), 3.9–4.3(4H, m), 5.00(1H, d, J=5.0Hz), 5.05(2H, s), 5.5–5.9(2H, m), 7.18(1H, d, J=15.3Hz), 7.56(1H, brs), 8.18(2H, brs), 8.27(1H, brs), 9.61(1H, d, J=8.3Hz) |
| 156 | 1765, 1598 | (DMSO-d$_6$)3.00(3H, s), 3.2–3.7(10H, m), 3.95–4.25(2H, m), 5.00(2H, d, J=4.7Hz), 5.05(2H, s), 5.45–5.8(2H, m), 7.09(2H, brs), 7.15(1H, d, J=15.0Hz), 8.18(2H, brs), 9.60(1H, d, J=8.2Hz) |
| 157 | 1765, 1598 | (DMSO-d$_6$)2.75–3.3(12H, m), 2.35–3.75(3H, m), 3.75–4.1(2H, m), 4.99(1H, d, J=4.8Hz), 5.05(2H, s), 5.35–5.8(2H, m), 7.10(1H, d, J=15.5Hz), 8.20(2H, brs), 9.62(1H, d, J=8.3Hz) |
| 158 | 1760, 1670, 1595 | (DMSO-d$_6$)3.2–3.4(2H, m), 4.99(1H, d, J=5.0Hz), 5.10(2H, s), 5.15–5.45(2H, m), 5.5–6.05(2H, m), 7.20(1H, d, J=15.5Hz), 8.19(3H, brs), 8.37(2H, d, J=6.0Hz), 8.80(1H, brs), 9.11(2H, d, J=6.0Hz), 9.63(1H, d, J=8.0Hz) |
| 159 | 1760, 1665, 1595 | (DMSO-d$_6$)3.06(6H, s), 3.35–3.65(2H, m), 4.15(2H, brs), 4.99(1H, d, J=5.2Hz), 5.05(2H, s), 5.4–5.85(2H, m), 7.15(1H, d, J=15.7Hz), |

| Example No. | Infrared absorption spectrum (cm$^{-1}$, Nujol) | NMR Spectrum (δ) |
|---|---|---|
| 160-A | 1765, 1595 | 8.18(2H, brs), 9.36(1H, s), 9.61(1H, d, J=8.0Hz) (DMSO-d$_6$)1.95-2.35(2H, m), 2.63(3H, s), 3.00(3H, s), 2.85-3.75(6H, m), 3.85-4.35(2H, m), 4.98(1H, d, J=5.1Hz), 5.04(2H, s), 5.25-5.75(2H, m), 7.13(1H, d, J=15.5Hz), 8.18(2H, brs), 9.60(1H, d, J=8.0Hz) |
| 160-B | 1760, 1590 | (DMSO-d$_6$)1.95-2.35(2H, m), 2.63(3H, s), 2.9-3.75(6H, m), 3.85-4.35(2H, m), 4.98(1H, d, J=5.0Hz), 5.04(2H, s), 5.3-5.75(2H, m), 7.13(1H, d, J=15.5Hz), 8.19(2H, brs), 9.60(1H, d, J=8.0Hz) |
| 161 | 1765, 1600 | (DMSO-d$_6$)2.1-2.45(4H, m), 2.9-3.9(10H, m), 3.95-4.2(2H, m), 5.04(1H, d, J=5.0Hz), 5.10(2H, s), 5.5-5.8(2H, m), 7.21(1H, d, J=16.0Hz), 8.30(2H, brs), 9.70(1H, d, J=8.0Hz) |

EXPERIMENT 11

Synthesis of the raw material compound 2-(5-Tritylamino-1,2,4-thiadiazol-3-yl)-(Z)-2-fluoromethoxyiminoacetyl chloride hydrochloride

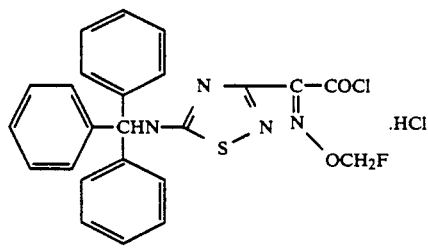

Phosphorous pentachloride (395 mg) was dissolved in dichloromethane (2.9 ml) and cooled to −5° C. To the solution was added the compound (627 mg) of Experiment 2, and agitated for 2 and half hours at the same temperature as described above. The reaction solution was added to a mixture of n-hexane (9.4 ml) and n-octane (9.4 ml). The resulting crystalline substance was collected by filtration, and washed with n-octane to obtain the objective product (325 mg).

Melting point: 139°-140° C. (decomposition);

Mass spectrum (m/e): M$^+$ . . . 480 ($^{35}$Cl), 482 ($^{37}$Cl)

Infrared absorption spectrum (cm$^{-1}$, Nujol): 1795, 1780, 1740, 1630;

NMR spectrum (δ, DMSO-d$_6$): 5.79(2H, d, J=54 Hz), 7.31(15H, s), 10.09(1H, s).

EXPERIMENT 12

Synthesis of the raw material compound 2-(5-Amino-1,2,4-thiadiazol-3-yl)-(Z)-2-fluoromethoxyiminoacetic acid ethyl ester

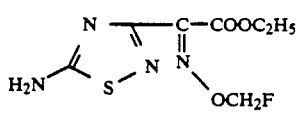

The compound (2.00 g) of Experiment 1 was agitated in trifluoroacetic acid at room temperature for 30 minutes. The solvent was distilled off, and the residue was purified by silica gel column chromatography to obtain the objective product (405 mg).

Melting point: 172°-173° C.

Infrared absorption spectrum (cm$^{-1}$, Nujol): 1730, 1615.

NMR spectrum (δ, DMSO-d$_6$): 1.28(3H, t, J=7.0 Hz), 4.34(2H, q, J=7.0 Hz), 5.83(2H, d, J=54.5 Hz), 8.27(2H, brs).

EXPERIMENT 13

Synthesis of the raw material compound 2-(5-Amino-1,2,4-thiadiazol-3-yl)-(Z)-2-fluoromethoxyiminoacetic acid The compound (200 mg) of Experiment 12 was suspended in a mixture of ethanol (6 ml) and water (2 ml), 1N aqueous sodium hydroxide solution (1.75 ml) was added thereto, and stirred at 60° C. for 1 hour. Ethanol was distilled off from the reaction solution, and the solution was adjusted to pH 2 with the use of 1N hydrochloric acid. The resulting solution was purified by means of "Dia-Ion SP207" (trade mark for nonionic adsorption resin manufactured by Mitsubishi Chemical Industries, Ltd.) to obtain the objective product (30 mg).

Infrared absorption spectrum (cm$^{-1}$, Nujol): 1720, 1620.

NMR spectrum (δ, DMSO-d$_6$): 5.74(2H, d, J=55 Hz), 8.24(2H, br).

EXPERIMENT 14

Synthesis of the raw material compound p-Methoxybenzyl 7β-[2-(5-tritylamino-1,2,4-thiadiazol-3-yl)-(Z)-2-fluoromethoxyiminoacetamido]-3-[(Z)-3-chloro-1-propen-1-yl]-3-cephem-4-carboxylate

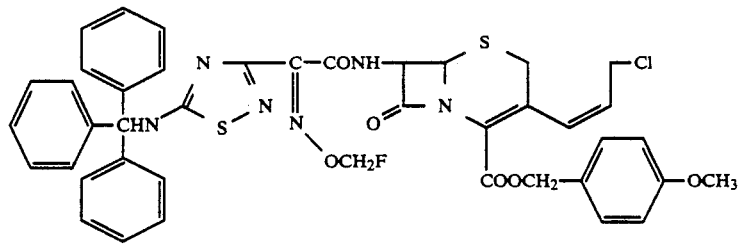

To a mixture of ethyl acetate (37 ml), tetrahydrofuran (5 ml), and dichloromethane (15.7 ml) were added N-(trimethylsilyl)acetamide (8.17 g) and p-methoxybenzyl 7β-amino-3-[(Z)-3-chloro-1-propen-1-yl]-3-cephem-4-carboxylate hydrochloride (3.33 g) to dissolve the latter materials. The solution was cooled to −20° C., then the compound of Experiment 11(3.80 g) was added thereto, and agitated at 10° C. for 1 hour. After the addition of ethyl acetate (500 ml) to the reaction solution, the mixture was washed successively with water, a saturated aqueous sodium bicarbonate solution, 1N hydrochloric acid, and a saturated brine solution, and then anhydrous magnesium sulfate was added thereto to dry the same. The solvent was distilled off, and the residue was purified by silica gel column chromatography to obtain the objective product (4.33 g).

The infrared absorption spectrum and the NMR spectrum of the resultant product coincided with those of Experiment 3.

EXPERIMENT 15

Synthesis of the raw material compound

2-Cyano-2-fluoromethoxyiminoacetamide

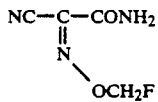

2-Cyano-2-hydroxyiminoacetamide (22.6 g) was dissolved in dimethyl sulfoxide (100 ml), and then potassium carbonate (55.2 g) was added thereto with stirring at room temperature, and the solution was further stirred for additional 20 minutes. Fluorobromomethane (27 g) dissolved in dimethylformamide (20 ml) was then added to the solution, and the solution was stirred for 20 hours at room temperature and then allowed to cool. The reaction solution was added to iced water (1 liter), and extracted twice with ethyl acetate (150 ml). The organic layer was washed twice with a saturated brine, and dried with addition of anhydrous magnesium sulfate, followed by distilling off the solvent. The residue was washed with ethyl ether, and dried to obtain the objective product (14.4 g).

Melting point: 124°–125° C.

Infrared absorption spectrum (cm$^{-1}$, Nujol): 3410, 3290, 3150, 1690, 1590.

NMR spectrum (δ, DMSO-d$_6$): 5.94 (2H, d, J=54.0 Hz), 7.85–9.40 (2H, b).

EXPERIMENT 16

Synthesis of the raw material compound

2-Fluoromethoxyiminopropanedinitrile

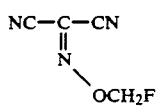

A mixture containing the compound (14.0 g) prepared in Experiment 15, acetonitrile (15 ml), sodium chloride (15 g) and phosphoryl chloride (14 ml) was reacted under reflux for 2 hours. To the mixture was added phosphoryl chloride (5 ml), and the whole was reacted for 2 hours. The reaction solution was, after cooling, added to iced water (200 ml) and stirred at room temperature for one hour. The solution was extracted twice with methylene chloride (50 ml). The extract was washed with 5% aqueous solution of sodium bicarbonate, and with a saturated brine, and then dried with addition of anhydrous magnesium sulfate. The solvent was distilled off. The resulting oily product was subjected to distillation under reduced pressure to obtain a colorless oily objective product (9.1 g).

Boiling point: 69°–70° C./25 mmHg.

NMR spectrum (δ, CDCl$_3$): 5.85 (2H, d, J=52.0 Hz).

EXPERIMENT 17

Synthesis of the raw material compound

2-Cyano-2-fluoromethoxyiminoacetamidine

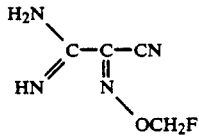

A mixed solution containing 28% aqueous ammonia (50 ml), ammonium chloride (8 g) and ethanol (50 ml) was cooled to −5° C. and the compound (9.1 g) prepared in Experiment 16 was added thereto with stirring, and then further stirred at the same temperature for additional 3 hours. Water (100 ml) was added to the reaction solution. The solution was extracted thrice with methylene chloride (50 ml). After drying the extract with addition of anhydrous magnesium sulfate, the solvent was distilled off. The residue was washed with ethyl ether and dried to obtain the objective product (3.4 g).

A portion of the product was dissolved in ethanol, and glacial acetic acid was dropped thereto with stirring. The resultant precipitates were recovered by filtration and washed with ethanol, followed by drying to obtain an acetate of the subject compound. The following data of physical properties are those of the acetate.

Melting point: 125°–127° C.

Infrared absorption spectrum (cm$^{-1}$, Nujol): 3200, 1670, 1570.

NMR spectrum (δ, DMSO-d$_6$): 1.90 (3H, s), 5.95 (2H, d, J=54.0 Hz), 7.40 (3H, b).

EXPERIMENT 18

Synthesis of the raw material compound 2-(5-Amino-1,2,4-thiadiazol-3-yl)-(E)-2-fluorometoxyiminoacetonitrile

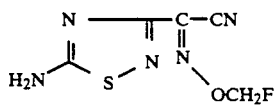

The compound (3.0 g) prepared in Experiment 17 was dissolved in methanol (50 ml), and triethylamine (4.2 g) was added thereto. After cooling the solution to −5° C., bromine (3.5 g) was dropped to the solution. A solution of potassium thiocyanate (2.1 g) in methanol was then dropped thereto at a temperature from −3° C. to −5° C., and the solution was stirred at the same temperature for 2 hours. The resulting precipitates were recovered by filtration and washed with water and with methanol. The precipitates were then recrystallized from acetone to obtain the objective product (3.4 g).

Melting point: 236°–238° C.

Infrared absorption spectrum (cm$^{-1}$, Nujol) 3450, 3250, 3075, 1610, 1520.

NMR spectrum (δ, DMSO-d$_6$): 6.02 (2H, d, J=54.0 Hz), 8.32 (2H, b).

EXPERIMENT 19

Synthesis of the raw material compound 2-(5-Amino-1,2,4-thiadiazol-3-yl)-(Z)-2-fluoromethoxyiminoacetamide

To a solution of sodium hydroxide (0.23 g) in water (18 ml) was added 35% aqueous hydrogen peroxide (7.4 ml). And, the compound (2.0 g) prepared in Experiment 18 was added thereto with stirring at room temperature. The solution was further stirred at a temperature from 25° C. to 30° C. for additional 8 hours. The precipitates deposited were recovered by filtration, and washed with water and with acetone, followed by drying to obtain the objective product (1.3 g).

Melting point: 210°–211° C.

Infrared absorption spectrum (cm$^{-1}$, Nujol): 3450, 3260, 3180, 1690, 1610.

NMR spectrum (δ, DMSO-d$_6$): 5.73 (2H, d, J=55.0 Hz), 7.69 (2H, br), 7.98 (1H, br), 8.10 (1H, br).

EXPERIMENT 20

2-(5-Amino-1,2,4-thiadiazol-3-yl)-(Z)-2-fluoromethoxyiminoacetic acid

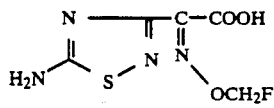

A mixture containing the compound (1.1 g) prepared in Experiment 19 and 2N aqueous sodium hydroxide solution (10 ml) was stirred at 50° C. for 5 hours. The reaction mixture was cooled, and adjusted to pH 1.0 with concentrated hydrochloric acid, followed by extraction thrice with ethyl acetate (20 ml). After addition of anhydrous magnesium sulfate to the extract, followed by drying, the solvent was ditilled off. The residue was washed with isopropyl ether to obtain a crude product (0.8 g). The crude product was purified by reversed phase silica gel column chromatography to obtain the objective product (0.4 g).

The infrared absorption spectrum and NMR spectrum were identical with those of Experiment 13.

EXAMPLE 162

Preparation of an injection

The compound (10 g) prepared in Example 1 was dissolved in distilled water (50 ml). The solution was divided and infused, so that the respective vial may contain 5 ml of the solution. This solution was lyophilized to give an injection.

EXAMPLE 163

Preparation of an injection

The compound (10 g) prepared in Example 151 was dissolved in distilled water (50 ml). The solution was divided and infused, so as to contain 5 ml per one vial. This solution was lyophilized to give an injection.

The acute toxicity and the anti-bacterial activity of the compounds according to this invention were determined as follows:

(1) Acute toxicity in mouse:

The compounds according to this invention dissolved in a physiological saline solution were intravenously dosed to five ICR male 6 weeks-old mouse. As the result, the values of acute toxicity of the compounds prepared in the following Examples were all in excess of 2 g/kg.

Example Numbers: 1, 2-1, 2-2, 3-1, 3-2, 5, 6-1, 6-2, 7-1, 7-2, 9-1, 9-2, 9-3, 10, 11, 12, 13-1, 13-2, 96, 121, 137, 145, 146, 150, 151, 154 and 155

(2) Anti-bacterial activity (MIC):

MIC (μg/ml) were determined by an agar dilution method [Chemotherapy (Japan), 29, 76–79, 1981]. Overnight cultures of the bacterial strains in Mueller-Hinton broth were diluted to final concentration of about 10$^6$ CFU/ml, and 5 μl of each bacterial suspension was spotted onto Mueller-Hinton agar plates that contained twofold serial dilutions of antibiotics. MICs were measured after incubation for 18 hours at 37° C.

As the controls, CAZ (Cefatazidime) and CTM (Cefotiam) were selected.

List of anti-bacterial activity

MIC (μg/ml)

Test bacterium

| Test compound | Staph. aureus 209-P | Escher. coli NIHJ | Kleb. pneumoniae EK-6 | Ser. marcescens ES-75 | Morganella morganii EP-14 | Pseud. aeruginosa EP-01 |
|---|---|---|---|---|---|---|
| Example | | | | | | |
| 1 | 0.2 | ≦0.025 | ≦0.025 | 0.1 | ≦0.025 | 0.8 |
| 2-1 | 0.4 | 0.05 | 0.05 | 0.05 | 0.05 | 1.56 |
| 2-2 | 0.4 | ≦0.025 | ≦0.025 | ≦0.025 | ≦0.025 | 1.56 |
| 3-1 | 0.2 | ≦0.025 | ≦0.025 | 0.05 | ≦0.025 | 0.8 |
| 3-2 | 0.2 | ≦0.025 | ≦0.025 | 0.1 | ≦0.025 | 1.56 |
| 4 | 0.4 | 0.05 | ≦0.025 | 0.1 | 0.05 | 0.8 |
| 5 | 0.2 | ≦0.025 | ≦0.025 | ≦0.025 | ≦0.025 | 0.8 |
| 6-1 | 0.2 | 0.05 | ≦0.025 | ≦0.025 | ≦0.025 | 0.8 |
| 6-2 | 0.1 | ≦0.025 | ≦0.025 | ≦0.025 | ≦0.025 | 0.8 |
| 7-1 | 0.2 | ≦0.025 | ≦0.025 | ≦0.025 | ≦0.025 | 0.8 |
| 7-2 | 0.2 | ≦0.025 | ≦0.025 | ≦0.025 | ≦0.025 | 0.8 |
| 8 | 0.2 | ≦0.025 | ≦0.025 | ≦0.025 | ≦0.025 | 0.8 |
| 9-1 | 0.4 | ≦0.025 | ≦0.025 | ≦0.025 | ≦0.025 | 0.8 |
| 9-2 | 0.4 | ≦0.025 | ≦0.025 | ≦0.025 | ≦0.025 | 0.8 |
| 9-3 | 0.4 | ≦0.025 | ≦0.025 | ≦0.025 | ≦0.025 | 0.8 |
| 10 | 0.8 | ≦0.025 | ≦0.025 | ≦0.025 | ≦0.025 | 1.56 |
| 11 | 0.4 | ≦0.025 | ≦0.025 | ≦0.025 | ≦0.025 | 0.8 |
| 12 | 0.4 | 0.05 | ≦0.025 | 0.1 | 0.05 | 1.56 |
| 13-1 | 0.2 | ≦0.025 | ≦0.025 | ≦0.025 | ≦0.025 | 0.8 |
| 13-2 | 0.2 | ≦0.025 | ≦0.025 | 0.05 | 0.05 | 1.56 |
| 14 | 0.2 | ≦0.025 | ≦0.025 | 0.05 | ≦0.025 | 0.8 |
| 15-1 | 0.4 | 0.05 | ≦0.025 | ≦0.025 | ≦0.025 | 1.56 |
| 15-2 | 0.4 | ≦0.025 | ≦0.025 | ≦0.025 | ≦0.025 | 1.56 |
| 16 | 0.2 | ≦0.025 | ≦0.025 | ≦0.025 | ≦0.025 | 0.8 |
| 17 | 0.4 | ≦0.025 | ≦0.025 | ≦0.025 | ≦0.025 | 0.8 |
| 19 | 0.2 | ≦0.025 | ≦0.025 | 0.05 | ≦0.025 | 0.8 |
| 20 | 0.2 | ≦0.025 | ≦0.025 | 0.05 | ≦0.025 | 1.56 |
| 21 | 0.2 | ≦0.025 | ≦0.025 | 0.1 | ≦0.025 | 1.56 |
| 22 | 0.2 | 0.05 | 0.05 | 0.2 | 0.05 | 3.13 |
| 23-1 | 0.2 | ≦0.025 | ≦0.025 | ≦0.025 | ≦0.025 | 1.56 |
| 23-2 | 0.2 | 0.05 | ≦0.025 | ≦0.025 | 0.05 | 1.56 |
| 24 | 0.2 | ≦0.025 | ≦0.025 | ≦0.025 | ≦0.025 | 1.56 |
| 26 | 0.2 | 0.1 | 0.1 | 0.4 | 0.1 | 0.8 |
| 27 | 0.4 | 0.05 | ≦0.025 | 0.1 | 0.05 | 1.56 |
| 28 | 0.4 | 0.05 | 0.05 | 0.2 | 0.05 | 1.56 |
| 29 | 0.4 | ≦0.025 | ≦0.025 | 0.1 | ≦0.025 | 0.8 |
| 30 | 0.4 | 0.05 | 0.05 | 0.2 | 0.05 | 1.56 |
| 31 | 0.4 | 0.05 | ≦0.025 | 0.1 | ≦0.025 | 1.56 |
| 32 | 0.2 | ≦0.025 | ≦0.025 | 0.05 | ≦0.025 | 1.56 |
| 35 | 0.4 | 0.05 | ≦0.025 | 0.1 | 0.05 | 0.8 |
| 36 | 0.2 | 0.05 | ≦0.025 | 0.1 | 0.05 | 1.56 |
| 37 | 0.2 | 0.05 | ≦0.025 | 0.1 | 0.05 | 1.56 |
| 38 | 0.4 | 0.1 | 0.05 | 0.2 | 0.1 | 1.56 |
| 39 | 0.2 | 0.05 | ≦0.025 | 0.1 | 0.05 | 1.56 |
| 40 | 0.4 | ≦0.025 | ≦0.025 | ≦0.025 | ≦0.025 | 0.8 |
| 42 | 0.2 | ≦0.025 | 0.05 | ≦0.025 | ≦0.025 | 1.56 |
| 43 | 0.2 | ≦0.025 | ≦0.025 | ≦0.025 | ≦0.025 | 0.8 |
| 44 | 0.4 | 0.05 | ≦0.025 | 0.1 | 0.05 | 1.56 |
| 45 | 0.4 | ≦0.025 | ≦0.025 | 0.1 | ≦0.025 | 0.8 |
| 50 | 0.4 | 0.05 | 0.05 | 0.2 | 0.05 | 1.56 |
| 51 | 0.4 | 0.05 | 0.05 | 0.05 | 0.05 | 1.56 |
| 53 | 0.8 | 0.05 | 0.05 | 0.1 | 0.05 | 0.8 |
| 55 | 0.2 | ≦0.025 | ≦0.025 | ≦0.025 | ≦0.025 | 0.4 |
| 56 | 0.4 | 0.05 | 0.05 | 0.1 | 0.05 | 1.56 |
| 57 | 0.2 | 0.05 | 0.05 | 0.2 | ≦0.025 | 0.8 |
| 58 | 0.2 | ≦0.025 | 0.05 | 0.05 | 0.05 | 1.56 |
| 59 | 0.4 | ≦0.025 | ≦0.025 | ≦0.025 | ≦0.025 | 1.56 |
| 60 | 0.2 | ≦0.025 | 0.05 | ≦0.025 | ≦0.025 | 1.56 |
| 61 | 0.4 | 0.1 | 0.05 | 0.05 | 0.1 | 1.56 |
| 62 | 0.2 | ≦0.025 | ≦0.025 | ≦0.025 | ≦0.025 | 0.4 |
| 63 | 0.4 | ≦0.025 | 0.05 | ≦0.025 | ≦0.025 | 0.8 |
| 64 | 0.2 | ≦0.025 | ≦0.025 | 0.1 | ≦0.025 | 0.8 |
| 65 | 0.4 | ≦0.025 | ≦0.025 | 0.05 | ≦0.025 | 0.8 |
| 66 | 0.4 | ≦0.025 | ≦0.025 | ≦0.025 | ≦0.025 | 0.8 |
| 67 | 0.1 | ≦0.025 | ≦0.025 | ≦0.025 | ≦0.025 | 0.8 |
| 68 | 0.2 | ≦0.025 | ≦0.025 | ≦0.025 | ≦0.025 | 0.8 |
| 69 | 0.2 | ≦0.025 | ≦0.025 | 0.05 | ≦0.025 | 0.8 |
| 70 | 0.1 | ≦0.025 | ≦0.025 | 0.1 | ≦0.025 | 0.8 |
| 72 | 0.4 | ≦0.025 | ≦0.025 | ≦0.025 | ≦0.025 | 0.8 |
| 73 | 0.4 | 0.05 | 0.05 | 0.05 | 0.1 | 1.56 |
| 74 | 0.8 | 0.1 | 0.05 | 0.4 | 0.1 | 1.56 |
| 75 | 0.4 | 0.05 | 0.05 | 0.2 | 0.05 | 1.56 |
| 77 | 0.4 | 0.2 | 0.2 | 0.2 | 0.4 | 3.13 |
| 78 | 0.4 | 0.2 | 0.2 | 0.2 | 0.2 | 3.13 |

-continued
List of anti-bacterial activity
MIC (μg/ml)
Test bacterium

| Test compound | Staph. aureus 209-P | Escher. coli NIHJ | Kleb. pneumoniae EK-6 | Ser. marcescens ES-75 | Morganella morganii EP-14 | Pseud. aeruginosa EP-01 |
|---|---|---|---|---|---|---|
| 81 | 0.2 | ≦0.025 | ≦0.025 | ≦0.025 | ≦0.025 | 1.56 |
| 82 | 0.4 | ≦0.025 | ≦0.025 | 0.05 | ≦0.025 | 1.56 |
| 83 | 0.8 | 0.05 | ≦0.025 | 0.1 | ≦0.025 | 3.13 |
| 84 | 0.4 | 0.05 | ≦0.025 | 0.1 | 0.05 | 1.56 |
| 85 | 0.2 | ≦0.025 | ≦0.025 | ≦0.025 | ≦0.025 | 1.56 |
| 88 | 0.2 | ≦0.025 | ≦0.025 | ≦0.025 | ≦0.025 | 0.8 |
| 89-1 | 0.2 | ≦0.025 | ≦0.025 | ≦0.025 | ≦0.025 | 0.8 |
| 89-2 | 0.2 | ≦0.025 | ≦0.025 | ≦0.025 | ≦0.025 | 0.8 |
| 90 | 0.2 | 0.05 | ≦0.025 | ≦0.025 | 0.05 | 0.8 |
| 91 | 0.2 | 0.05 | ≦0.025 | ≦0.025 | ≦0.025 | 1.56 |
| 92 | 0.2 | ≦0.025 | ≦0.025 | ≦0.025 | ≦0.025 | 0.8 |
| 93 | 0.2 | ≦0.025 | ≦0.025 | ≦0.025 | ≦0.025 | 0.8 |
| 94 | 0.2 | ≦0.025 | ≦0.025 | ≦0.025 | ≦0.025 | 0.8 |
| 95 | 0.2 | 0.05 | ≦0.025 | ≦0.025 | ≦0.025 | 0.8 |
| 96 | 0.2 | ≦0.025 | ≦0.025 | ≦0.025 | ≦0.025 | 0.8 |
| 97 | 0.2 | ≦0.025 | ≦0.025 | ≦0.025 | ≦0.025 | 0.8 |
| 98 | 0.4 | 0.05 | 0.05 | 0.05 | ≦0.025 | 3.13 |
| 99 | 0.2 | ≦0.025 | ≦0.025 | ≦0.025 | ≦0.025 | 1.56 |
| 100 | 0.2 | ≦0.025 | ≦0.025 | 0.05 | ≦0.025 | 1.56 |
| 101 | 0.2 | 0.05 | ≦0.025 | ≦0.025 | ≦0.025 | 1.56 |
| 102 | 0.2 | ≦0.025 | ≦0.025 | 0.05 | ≦0.025 | 1.56 |
| 103 | 0.1 | ≦0.025 | ≦0.025 | ≦0.025 | ≦0.025 | 3.13 |
| 106 | 0.4 | ≦0.025 | 0.05 | 0.1 | 0.05 | 3.13 |
| 107 | 0.2 | 0.05 | ≦0.025 | 0.05 | ≦0.025 | 1.56 |
| 108 | 0.4 | 0.05 | ≦0.025 | 0.1 | 0.05 | 3.13 |
| 114 | 0.2 | 0.05 | ≦0.025 | 0.05 | ≦0.025 | 0.8 |
| 115 | 0.8 | ≦0.025 | ≦0.025 | 0.05 | ≦0.025 | 3.13 |
| 116 | 0.2 | ≦0.025 | ≦0.025 | ≦0.025 | ≦0.025 | 1.56 |
| 117 | 0.4 | 0.05 | 0.05 | 0.2 | ≦0.025 | 1.56 |
| 118 | 0.2 | ≦0.025 | ≦0.025 | 0.1 | ≦0.025 | 0.4 |
| 119 | 0.2 | ≦0.025 | ≦0.025 | 0.05 | ≦0.025 | 0.8 |
| 120 | 0.2 | ≦0.025 | ≦0.025 | 0.05 | ≦0.025 | 0.8 |
| 121 | 0.2 | ≦0.025 | ≦0.025 | 0.1 | ≦0.025 | 0.8 |
| 122-A | 0.2 | ≦0.025 | ≦0.025 | ≦0.025 | ≦0.025 | 0.8 |
| 122-B | 0.1 | ≦0.025 | ≦0.025 | 0.05 | ≦0.025 | 0.8 |
| 123 | 0.4 | 0.05 | 0.05 | 0.2 | 0.05 | 1.56 |
| 124 | 0.2 | 0.05 | ≦0.025 | 0.1 | 0.05 | 0.8 |
| 125 | 0.4 | ≦0.025 | ≦0.025 | ≦0.025 | ≦0.025 | 1.56 |
| 126 | 0.1 | ≦0.025 | ≦0.025 | 0.05 | ≦0.025 | 0.8 |
| 127 | 0.1 | ≦0.025 | ≦0.025 | 0.05 | ≦0.025 | 0.8 |
| 128 | 0.2 | 0.05 | 0.05 | 0.1 | 0.05 | 0.8 |
| 129 | 0.2 | ≦0.025 | ≦0.025 | 0.05 | ≦0.025 | 0.8 |
| 143 | 0.2 | 0.05 | ≦0.025 | 0.1 | ≦0.025 | 0.8 |
| 144 | 0.2 | ≦0.025 | 0.05 | 0.1 | ≦0.025 | 0.8 |
| 145 | 0.4 | 0.2 | 0.1 | 0.1 | 0.1 | 1.56 |
| 146 | 0.4 | 0.1 | 0.05 | 0.05 | 0.05 | 1.56 |
| 147 | 0.2 | 0.1 | 0.05 | 0.2 | 0.05 | 1.56 |
| 148 | 0.4 | 0.1 | 0.05 | 0.05 | 0.1 | 1.56 |
| 149 | 0.2 | 0.1 | 0.05 | 0.05 | 0.05 | 1.56 |
| 150 | 0.4 | 0.2 | 0.1 | 0.1 | 0.1 | 1.56 |
| 151 | 0.4 | 0.1 | 0.05 | 0.05 | 0.05 | 1.56 |
| 152 | 0.2 | 0.1 | 0.05 | 0.05 | 0.05 | 1.56 |
| 153 | 0.4 | 0.2 | 0.1 | 0.1 | 0.1 | 1.56 |
| 154 | 0.4 | 0.1 | 0.1 | 0.1 | 0.1 | 0.8 |
| 155 | 0.4 | 0.1 | 0.05 | 0.2 | 0.1 | 1.56 |
| 156 | 0.4 | 0.1 | 0.1 | 0.1 | 0.1 | 0.8 |
| 157 | 0.4 | 0.1 | 0.1 | 0.2 | 0.1 | 1.56 |
| 158 | 0.2 | ≦0.025 | ≦0.025 | 0.1 | 0.1 | 1.56 |
| 159 | 0.4 | 0.05 | 0.05 | 0.1 | 0.1 | 1.56 |
| 160-A | 0.1 | ≦0.025 | ≦0.025 | 0.1 | 0.05 | 0.8 |
| 160-B | 0.1 | 0.05 | 0.05 | 0.2 | 0.05 | 0.8 |
| 161 | 0.2 | 0.05 | 0.05 | 0.2 | 0.1 | 1.56 |
| Control | | | | | | |
| CAZ | 6.25 | 0.2 | 0.1 | 0.2 | 0.1 | 1.56 |
| CTM | 0.2 | 0.1 | 0.1 | 6.25 | 0.2 | >100 |

3. Anti-bacterial activity (MIC):

Comparison tests of the anti-bacterial activities were conducted between the compounds of the following formula according to the present invention and the corresponding control compounds wherein $R_1$ represents methyl group. Measurements of MIC are the same as described in the above item 2. The results are shown in the following table.

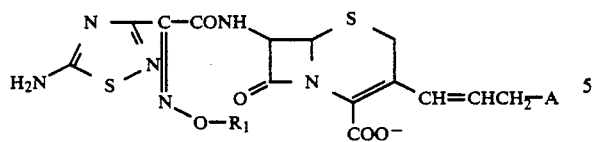

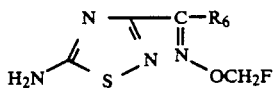

wherein $R_6$ represents carboxyl, a halogenocarbonyl, carbamoyl or cyano group, a compound wherein said amino and/or carboxyl group is protected with a protective group, or a salt thereof.

| A | $R_1$ | MIC (µg/ml) Test bacteria | | | |
|---|---|---|---|---|---|
| | | Staph. aureus E 31106 | Enterobacter cloacae E-74 | Proteus vulgaris E 08042 | Xantomonas maltophilia E 04004 |
| ![A1] | —$CH_2F$ (Example 126) —$CH_3$ (Control) | 1.56 6.25 | 0.05 0.1 | 0.05 1.56 | 12.5 100 |
| ![A2] | —$CH_2F$ (Example 127) —$CH_3$ (Control) | 3.13 6.25 | ≦0.025 0.4 | ≦0.025 3.13 | 6.25 50 |
| ![A3] | —$CH_2F$ (Example 125) —$CH_3$ (Control) | 6.25 12.5 | 0.4 3.13 | 0.2 12.5 | 25 50 |
| ![A4] | —$CH_2F$ (Example 128) —$CH_3$ (Control) | 3.13 6.25 | 0.1 0.2 | 0.1 6.25 | 25 >100 |

What is claimed is:

1. A compound of the formula:

2. 2-(5-Amino-1,2,4-thiadiazol-3-yl)-(Z)-2-fluoromethoxyimino acetic acid.

3. 2-(5-Amino-1,2,4-thiadiazol-3-yl)-(E)-2-fluoromethoxyimino acetonitrile.

4. 2-(5-Amino-1,2,4-thiadiazol-3-yl)-(Z)-2-fluoromethoxyimino acetamide.

5. 2-(5-Amino-1,2,4-thiadiazol-3yl)-(Z)-2-fluoromethoxyiminoacetyl chloride.

* * * * *